(12) United States Patent
Maruyama et al.

(10) Patent No.: US 6,586,468 B1
(45) Date of Patent: Jul. 1, 2003

(54) ω-SUBSTITUTED PHENYL-PROSTAGLANDIN E DERIVATIVES AND DRUGS CONTAINING THE SAME AS THE ACTIVE INGREDIENT

(75) Inventors: Toru Maruyama, Osaka (JP); Shuichi Ohuchida, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/787,087

(22) PCT Filed: Sep. 10, 1999

(86) PCT No.: PCT/JP99/04934

§ 371 (c)(1),
(2), (4) Date: Jun. 11, 2001

(87) PCT Pub. No.: WO00/15608

PCT Pub. Date: Mar. 23, 2000

(30) Foreign Application Priority Data

Sep. 14, 1998 (JP) .............................. 10-279347

(51) Int. Cl.[7] ...................... A61K 31/215; A61K 31/19; C07C 69/76; C07C 59/90; C07C 59/48
(52) U.S. Cl. .................... 514/530; 514/570; 560/53; 560/60; 562/463; 562/470
(58) Field of Search ................. 514/530, 570; 562/463, 470; 560/53, 60

(56) References Cited

U.S. PATENT DOCUMENTS 4,154,949 A * 5/1979 Johnson
6,107,338 A * 8/2000 Wos et al.

FOREIGN PATENT DOCUMENTS

| GB | 1508168 | 4/1978 |
|----|---------|--------|
| GB | 1535373 | 12/1978 |
| JP | 51125257 | 4/1978 |
| JP | 51113847 | 12/1978 |
| JP | 8059607 | 3/1996 |

* cited by examiner

Primary Examiner—Samuel Barts
Assistant Examiner—Paul A. Zucker
(74) Attorney, Agent, or Firm—Stevens, Davis, Miller & Mosher, L.L.P.

(57) ABSTRACT

A ω-substituted phenyl-prostaglandin of formula (I), a process for the preparation thereof, a mediciament comprising it as active ingredient (all symbols have the same meaning as described in the specification).

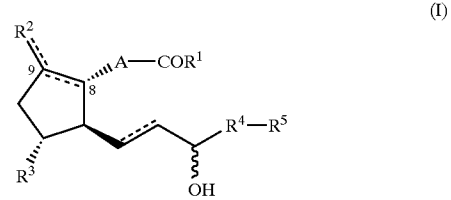

The compounds of the formula (I) bind strongly in $PGE_2$ receptor (especially subtype $EP_4$) and therefore are useful for the prophylaxis and/or treatment of immune diseases (autoimmune diseases (amyotrophic lateral sclerosis (ALS) etc.), post-transplantation graft rejection, etc.), asthma, abnormal bone formation, neurocyte death, pulmopathy, hepatopathy, etc. They are also related to sleeping disorders and platelet coagulations, and therefore they are also applicable to these diseases.

24 Claims, No Drawings

ω-SUBSTITUTED PHENYL-PROSTAGLANDIN E DERIVATIVES AND DRUGS CONTAINING THE SAME AS THE ACTIVE INGREDIENT

This application was filed under 35 USC §371, of PCT Application No. PCT/JP99/04934, having an International Filing Date of Sep. 10, 1999, claiming benefit of Japanese application no. 10-279347, filed on Sep. 14, 1998.

TECHNICAL FIELD

The present invention relates to ω-substituted phenyl-prostaglandin E derivatives. More particularly, the present invention relates to (1) ω-substituted phenyl-prostaglandin E derivatives of formula (I)

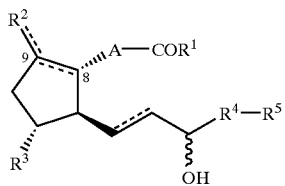

(wherein all symbols have the same meaning as described hereafter.), (2) a process for the preparation thereof and (3) a medicament comprising them as active ingredient.

BACKGROUND

Prostaglandin $E_2$ (abbreviated as $PGE_2$ hereafter.) has been known as a metabolite in the arachidonic acid cascade. It has been known that $PGE_2$ has cyto-protective activity, uterine contractile activity, a pain-inducing effect, a promoting effect on digestive peristalsis, an awakening effect, a suppressive effect on gastric acid secretion, hypotensive activity and diuretic activity, etc.

In the recent studies, it was found that $PGE_2$ receptor was divided into some subtypes which possess different physiological roles from each other. At present, four main receptor subtypes are known and they are called $EP_1$, $EP_2$, $EP_3$ and $EP_4$ (Negishi M. et al., J. Lipid Mediators Cell Signaling, 12, 379–391 (1995)).

The present inventors investigated to find new compounds which bind on each receptor specifically, so that we found that the compounds of the present invention could bind selectively on $EP_4$ subtype receptor and achieved the present invention.

The compounds of the present invention of formula (I) bind strongly on subtype $EP_4$ and therefore are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burn, systemic granuloma, ulcerative colititis, Crohn's diseases, hypercytokinemia at dialysis, multiple organ failure, shock, etc. They are also related with sleeping disorders and platelet coagulations, and therefore they are thought to be applicable to these diseases.

The compounds of the present invention of formula (I) bind weakly on other PG receptors including other subtypes and do not express other effects, and therefore it is probable that those compounds will be medical agents having less side-effects.

On the other hand, a lot of PG compounds wherein phenyl group is introduced in the ω-chain are known, e.g. the following patent applications. The comments in the parenthesis show the use of the compounds.

9-oxo type: JP kokai sho 49-92053 (i.e. U.S. Pat. No. 4,036,832) (hypotensive effect etc.), 9-chloro substituted type: JP kokai sho 56-92860 (i.e. U.S. Pat. No. 4,444,788) (luteal recessive effect etc.), 9-fluoro substituted type: JP kokai sho 58-8059 (i.e. U.S. Pat. No. 4,454,339) (luteal recessive effect etc.), 11-deoxy type: JP kokai sho 53-135956 (i.e. U.S. Pat. No. 3,932,389) (intermediates for prostaglandin having hypotensive effect etc.).

JP Kokai Sho 49-92053 (i.e U.S. Pat. No. 4,036,832) discloses that the following compounds have a hypotensive effect, stimulating effect against smooth muscle, peptic ulcers, bronchodilator effect and therefore they are useful.

A compound of formula (A)

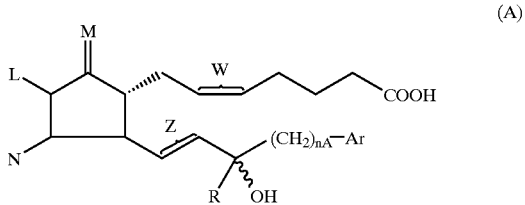

(wherein Ar is α- or β-furyl, α- or β-thienyl, α- or β-naphthyl, phenyl, 3,4-dimethoxyphenyl, 3,4-methylenedioxyphenyl, 3,4,5-trimethoxyphenyl or phenyl monosubstituted by halo, trifluoromethyl, phenyl, lower alkyl or lower alkoxy, nA is 0 or an integer of 1~5, with the proviso that when Ar is phenyl, substituted phenyl or naphthyl, then nA is 0 or 1, R is hydrogen atom or lower alkyl, W is a bond or a cis double bond, Z is a bond or a trans double bond, M is keto,

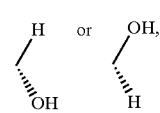

N and L are taken together to form a bond or when L is hydrogen, N is selected so as to complete A, E or F prostaglandin structure), or lower alkanoyl, formyl or benzoyl ester of free hydroxy group in C9, C11 or C15 position and a pharmaceutically acceptable salt thereof.

The specification provides specific $PGE_2$ compounds in which phenyl substituted by alkyl or alkoxy is introduced in the ω-chain; i.e. the compounds of examples 55 and 72 of the following formula.

Example 55:

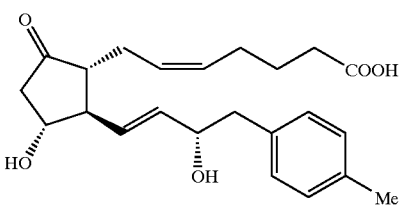
(A-1)

Example 72:

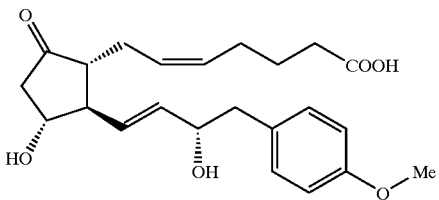
(A-2)

DISCLOSURE OF THE PRESENT INVENTION

The present invention consists in, as described hereafter, the fact that the present inventors have found that PGE compounds in which the ω-chain includes phenyl group substituted by particular substituents bind strongly on $EP_4$ and bind weakly on the other PG receptors including other subtypes than $EP_4$. In other words, the present inventors have found that adoption of particular groups maintained $EP_4$ activity and the selectivity for $EP_4$ over other receptors is improved, to complete the invention.

The present invention relates to (1) an ω-substituted phenyl prostaglandin E derivative of formula (I)

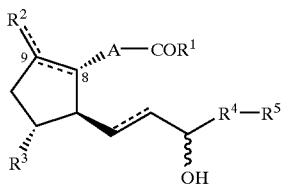
(I)

(wherein A is C2~8 alkylene, C2~8 alkenylene, C1~4 alkylene-phenylene, or
C2~4 alkenylene-phenylene,
$R^1$ is hydroxy, C1~6 alkyloxy, C1~6 alkyloxy-C1~6 alkyloxy, HO—C1~6 alkyloxy or a formula of $NR^6R^7$ (wherein $R^6$ and $R^7$ are each independently hydrogen atom or C1~4 alkyl),
$R^2$ is oxo, halogen or a group of formula $R^8$—COO- (wherein $R^8$ is hydrogen, C1~4 alkyl, phenyl or phenyl (C1~4 alkyl), C1~4 alkyloxy, HOOC—C1~4 alkyl, C1~4 alkyloxy-carbonyl-C1~4 alkyl, HOOC—C2~4 alkenyl or C1~4 alkyloxy-carbonyl-C2~4 alkenyl),
$R^3$ is hydrogen atom or hydroxy,
$R^4$ is C1~4 alkylene,
$R^5$ is phenyl substituted by the following groups:
  i) 1~3 groups selected from
    C1~4 alkyloxy-C1~4 alkyl,
    C2~4 alkenyloxy-C1~4 alkyl,
    C2~4 alkynyloxy-C1~4 alkyl,
    C3~7 cycloalkyloxy-C1~4 alkyl,
    C3~7 cycloalkyl(C1~4 alkyloxy)-C1~4 alkyl,
    phenyloxy-C1~4 alkyl,
    phenyl-C1~4 alkyloxy-C1~4 alkyl,
    C1~4 alkylthio-C1~4 alkyl,
    C2~4 alkenylthio-C1~4 alkyl,
    C2~4 alkynylthio-C1~4 alkyl,
    C3~7 cycloalkylthio-C1~4 alkyl,
    C3~7 cycloalkyl(C1~4 alkylthio)-C1~4 alkyl,
    phenylthio-C1~4 alkyl and
    phenyl-C1~4 alkylthio-C1~4 alkyl,
  ii) C1~4 alkyloxy-C1~4 alkyl and C1~4 alkyl,
    C1~4 alkyloxy-C1~4 alkyl and C1~4 alkyloxy,
    C1~4 alkyloxy-C1~4 alkyl and hydroxyl,
    C1~4 alkyloxy-C1~4 alkyl and halogen,
    C1~4 alkylthio-C1~4 alkyl and C1~4 alkyl,
    C1~4 alkylthio-C1~4 alkyl and C1~4 alkyloxy,
    C1~4 alkylthio-C1~4 alkyl and hydroxy or
    C1~4 alkylthio-C1~4 alkyl and halogen,
  iii) halo-C1~4 alkyl or hydroxy-C1~4 alkyl, or
  iv) C1~4 alkyl and hydroxy; and ══ is a bond or a double bond, and when $R^2$ is a group of formula $R^8$—COO—, $R^1$ is C1~6 alkoxy, C1~6 alkyloxy-C1~6 alkyloxy or HO—C1~6 alkyloxy and 8–9 position is a double bond), a non-toxic salt thereof or a cyclodextrin clathrate thereof, (2) a process for the preparation thereof and (3) a medicament comprising it as active ingredient.

Description

In the formula (I), C1~4 alkyl in $R^5$, $R^6$, $R^7$ and $R^9$ is methyl, ethyl, propyl, butyl and isomers thereof.

In the formula (I), C1~6 alkyl in $R^1$ is methyl, ethyl, propyl, butyl, pentyl, hexyl and isomers thereof.

In the formula (I), C1~4 alkylene in $R^4$ and A is methylene, ethylene, trimethylene, tetramethylene and isomers thereof.

In the formula (I), C2~8 alkylene represented by A is methylene, ethylene, trimethylene, tetramethylene, pentamethylene, hexamethylene, heptamethylene, octamethylene and isomers thereof.

In the formula (I), C2~8 alkenylene represented by A includes one or two double bond(s) in itself, for example, vinylene, propenylene, butenylene, pentenylene, hexenylene, heptenylene, octenylene, pentadienylene, hexadienylene, heptadienylene, octadienylene and isomers thereof.

In the formula (I), C2~4 alkenylene in A is vinylene, propenylene, butenylene and isomers thereof.

In the formula (I), C2~4 alkenyl in $R^5$ and $R^8$ is vinyl, propenyl, butenyl and isomers thereof.

In the formula (I), C2~4 alkynyl in $R^5$ is ethynyl, propynyl, butynyl and isomers thereof.

In the formula (I), C3~7 cycloalkyl in $R^8$ is cyclopropyl, cyclobutyl, cyclopentyl, cyclohexyl and cycloheptyl.

In the formula (I), halogen in $R^2$ and $R^8$ is fluorine, chlorine, bromine and iodine.

In the present invention, as may be easily understood by those skilled in the art,

----- indicates a single bond or a double bond, unless otherwise specified, the symbol:

indicates that the substituent attached thereto is in front of the sheet (β-position), indicates that the substituent attached thereto is behind the sheet (α-position), and indicates that the substituent attached thereto is in β-position or α-position or a mixture thereof.

Unless otherwise specified, all isomers are included in the present invention. For example, alkyl, alkenyl, alkynyl and alkylene include straight-chain and branched-chain ones. Isomers in the double bonds, rings, fused rings (e.g. E, Z, cis, trans isomers), isomers generated by the existence of asymmetric carbon atom(s) (e.g. R, S isomers, α, β isomers, enantiomers, diastereomers), optically active isomers having optically rotatory power (D, L, d, l isomers), polar isomers separated by chromatography (more polar, less polar isomers), equilibrium compounds, arbitrary ratios of these compounds, racemic mixtures are all included in the present invention.

In the formula (I), the group of formula is preferably, (1)
(2)
(3)
(4)
(5)
(6)
(7)

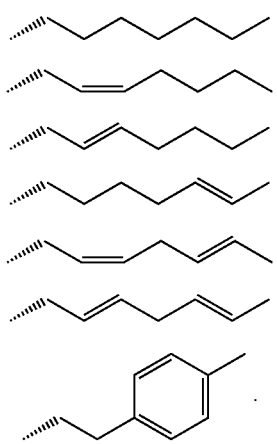

In the formula (I), hydroxy in the 15-position is preferably attached as the α-configuration.

In the formula (I), in the alkylene of $R^4$, methylene is most preferable.

In the formula (I), the position of the substituent of phenyl in $R^5$ is preferably the 3-position, the combination of 3- and 4-position and the combination of 3- and 5-position.

In the compounds of the present invention of formula (I), the compounds described in the examples, the following compounds and corresponding esters, amides and 8-acylated compounds thereof are preferable.

TABLE 1

(1)

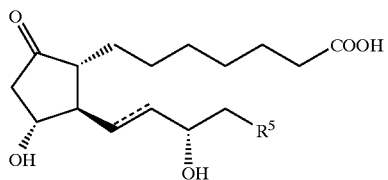

| $R^5$ |
|---|
| 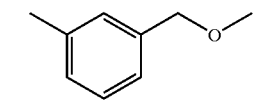 |
| 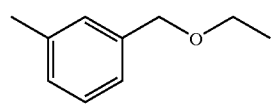 |
| 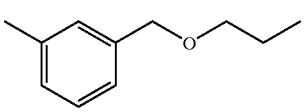 |
| 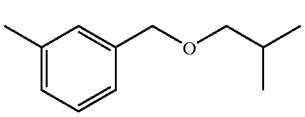 |
| 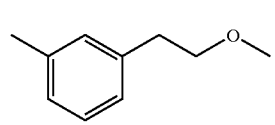 |
| 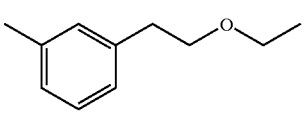 |
| 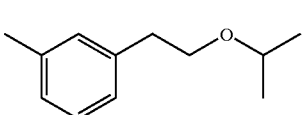 |
| 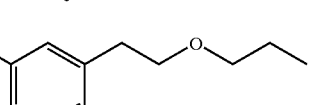 |
| 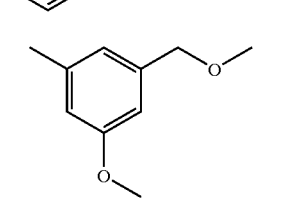 |

TABLE 1-continued
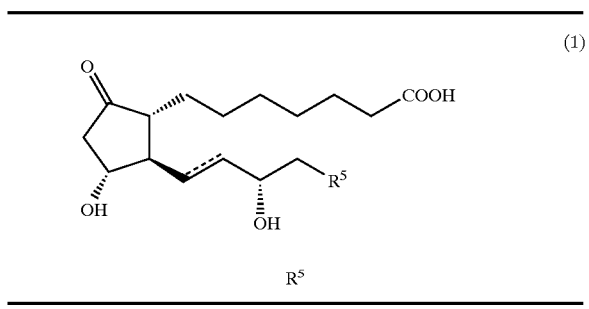
(1)
R⁵
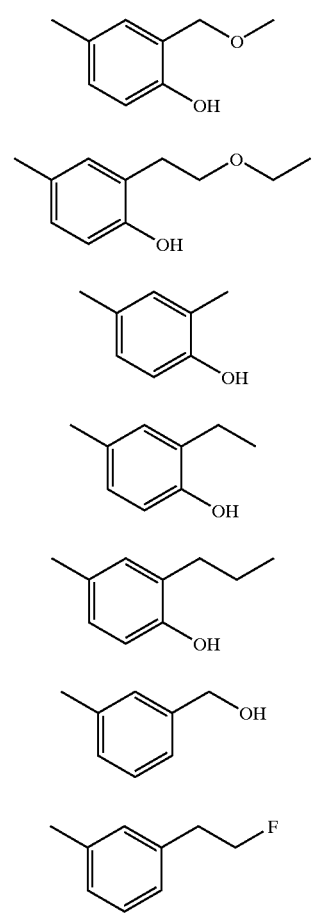
TABLE 2
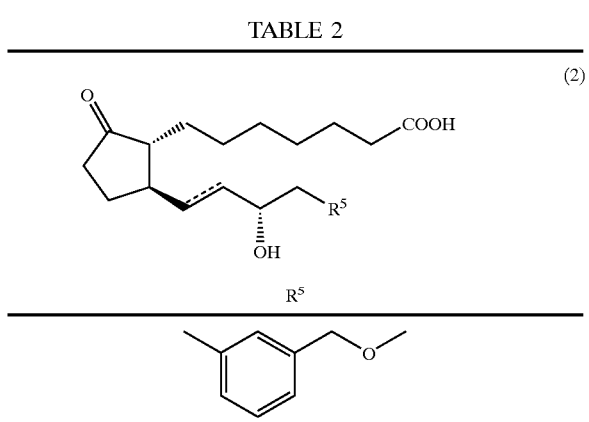
(2)
R⁵
TABLE 2-continued
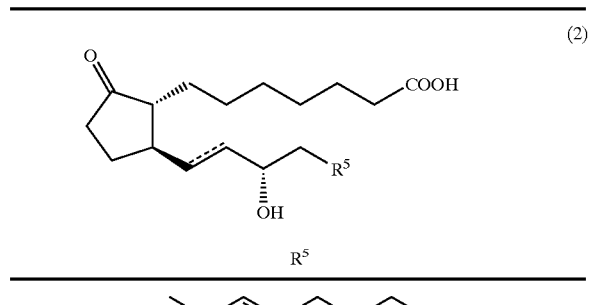
(2)
R⁵
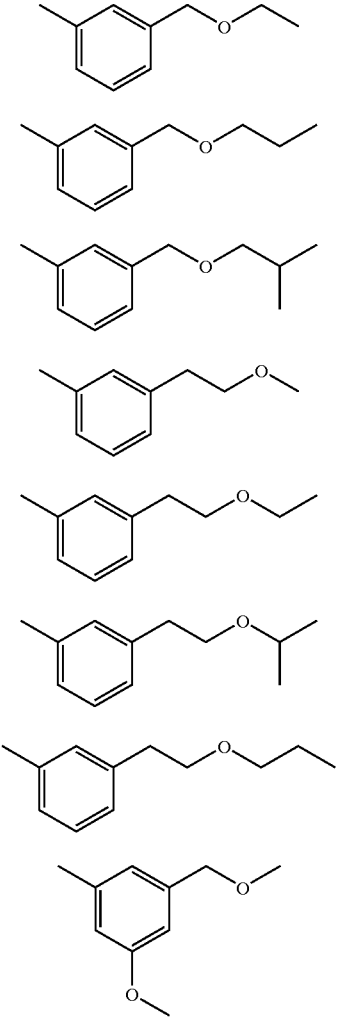
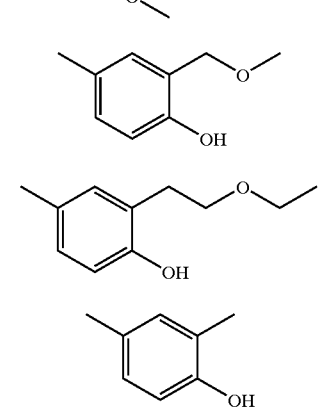

TABLE 2-continued
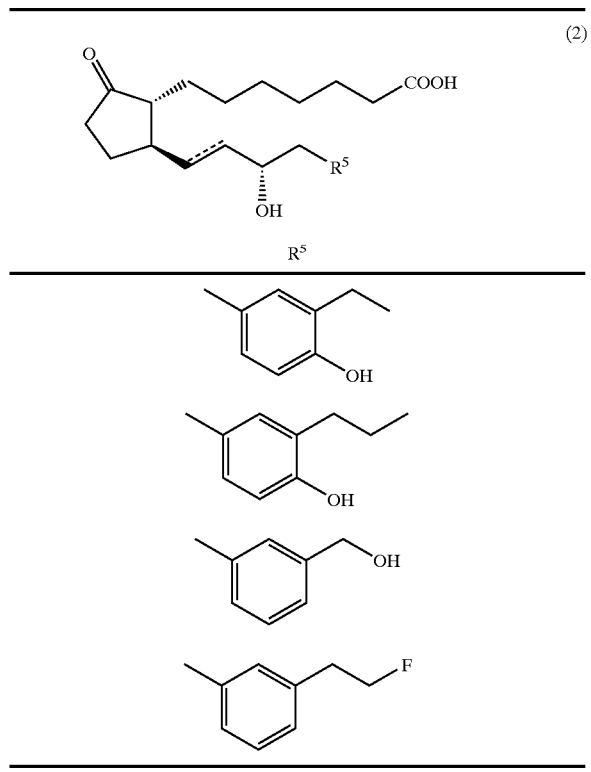
TABLE 3
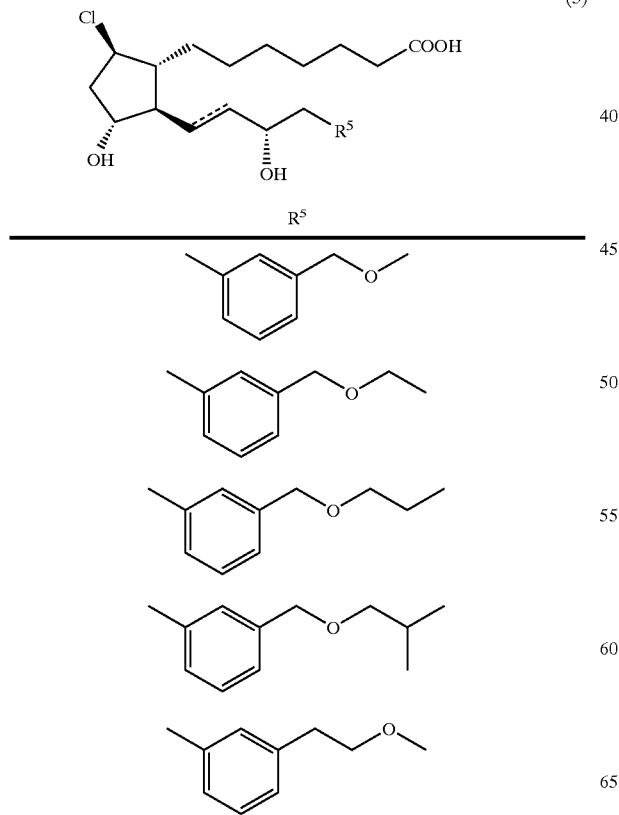
TABLE 3-continued
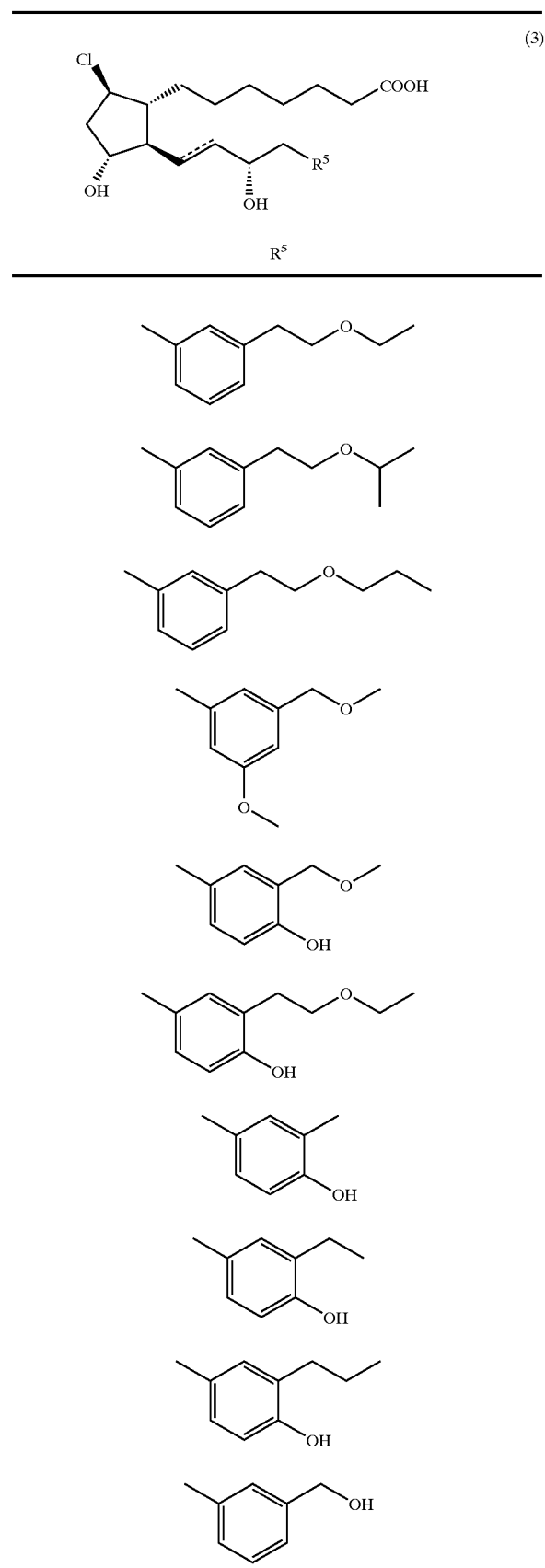

TABLE 3-continued
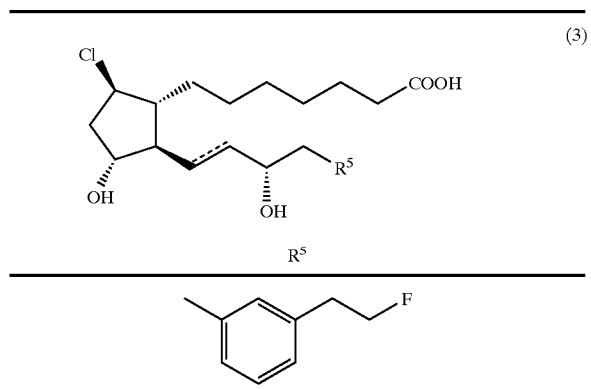
TABLE 4
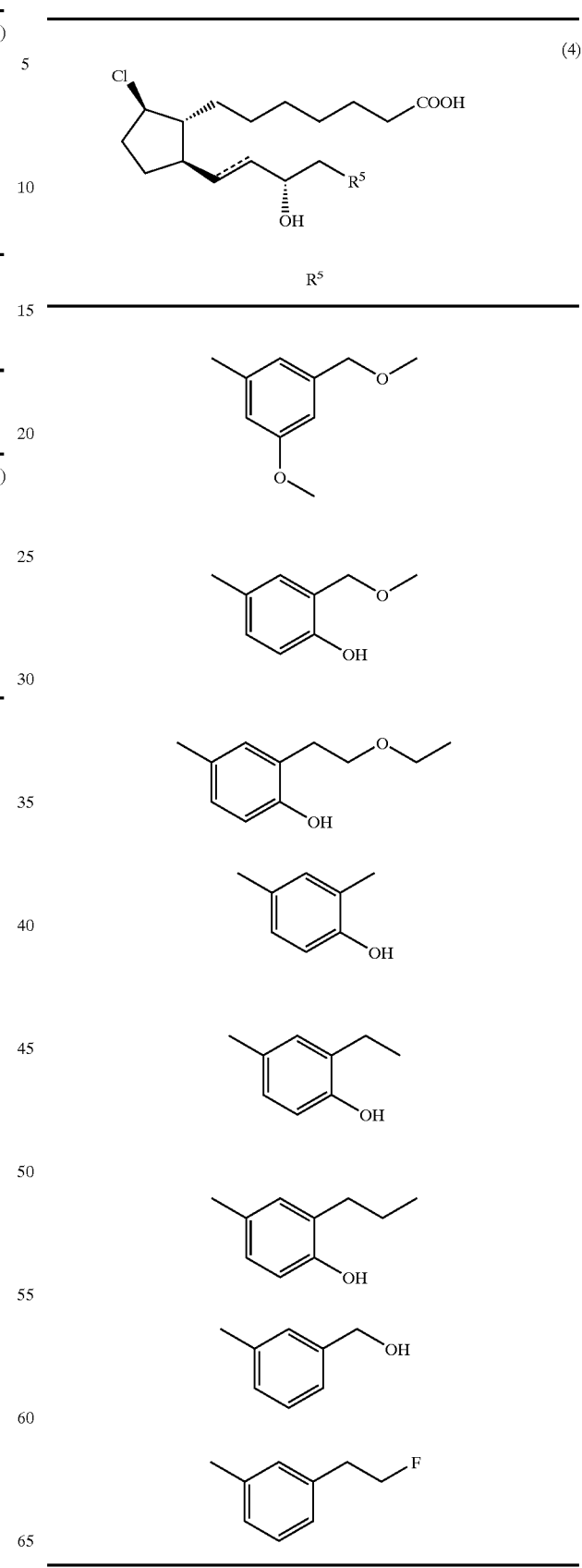

TABLE 5
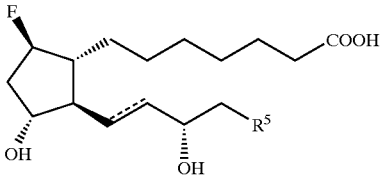
TABLE 5-continued
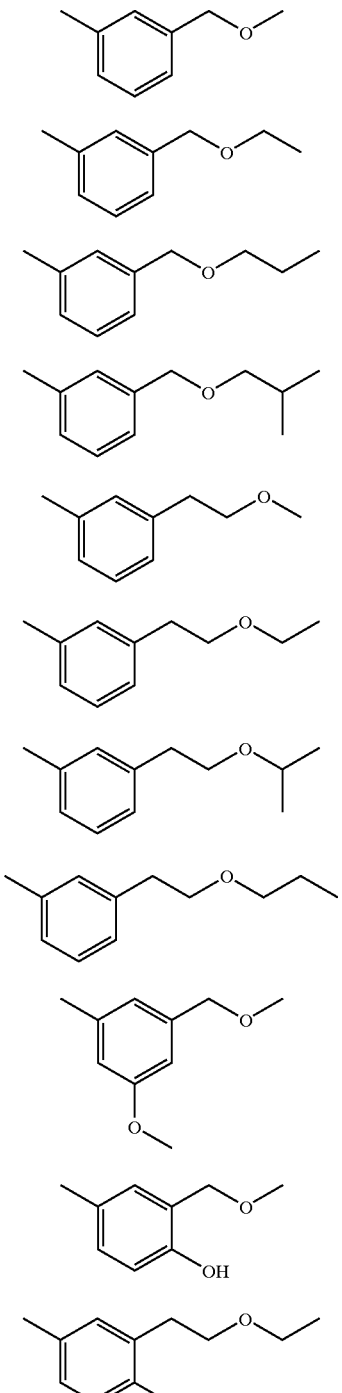
TABLE 6
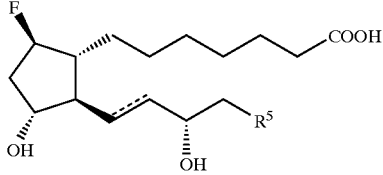

TABLE 6-continued
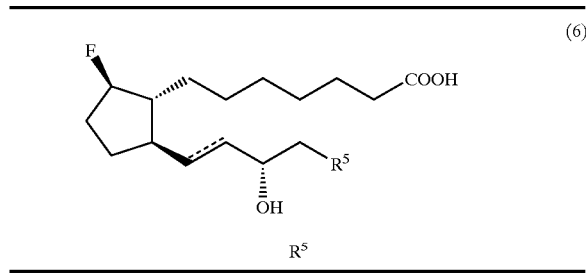
(6)
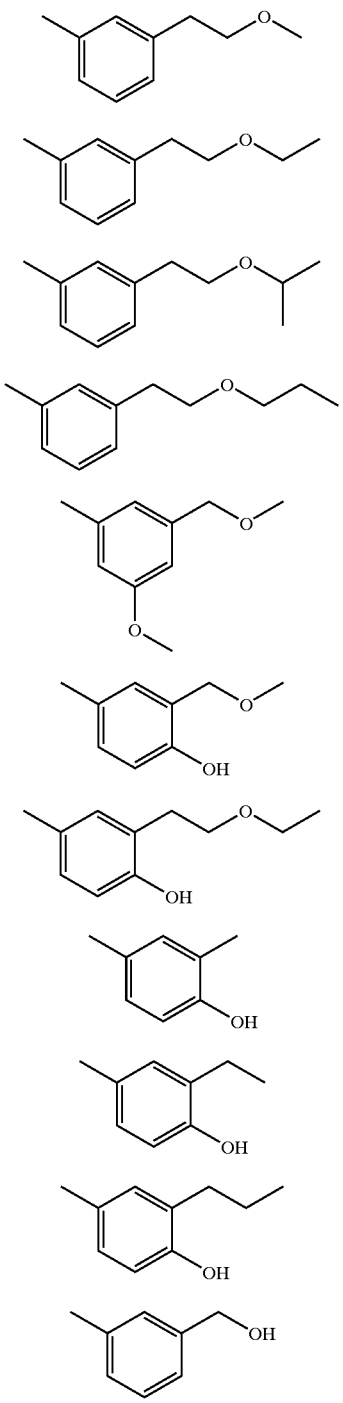
TABLE 6-continued
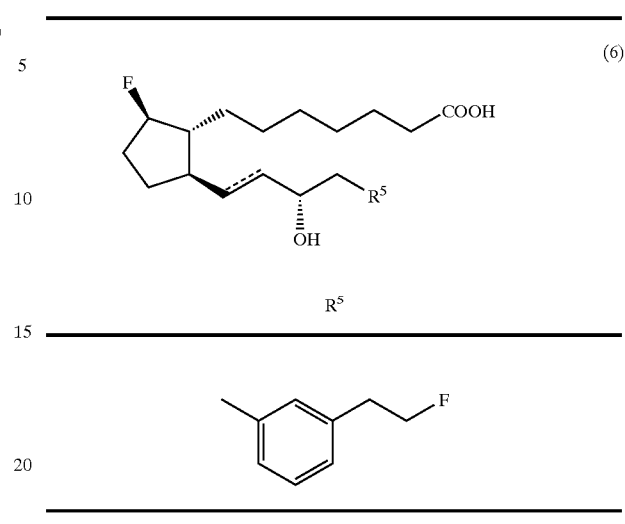
(6)
TABLE 7
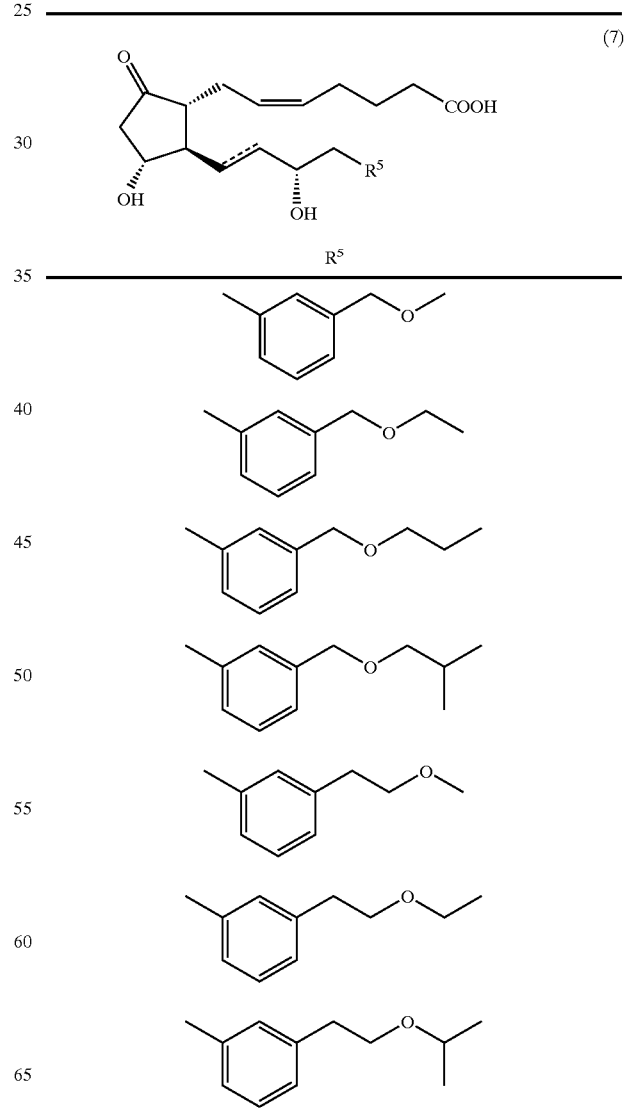
(7)

TABLE 7-continued (7)

[Structure: cyclopentanone with hydroxyl substituent, connected to CH=CH-CH(OH)-CH2-R5 chain and CH2-CH=CH-CH2-CH2-CH2-COOH chain]

R5

- 3-methylphenyl-CH2CH2-O-CH2CH2CH3
- 3,5-disubstituted phenyl with CH2-O-CH3 and OCH3
- 2-(methoxymethyl)-4-methylphenol
- 2-(2-ethoxyethyl)-4-methylphenol
- 2,4-dimethylphenol
- 2-ethyl-4-methylphenol
- 4-methyl-2-propylphenol
- 3-methylbenzyl alcohol
- 3-methylphenyl-CH2CH2-F

TABLE 8

(8)

[Structure: cyclopentanone connected to CH2-CH=CH-CH2-CH2-COOH chain and CH=CH-CH(OH)-CH2-R5 chain]

R5

- 3-methylbenzyl methyl ether
- 3-methylbenzyl ethyl ether
- 3-methylbenzyl propyl ether
- 3-methylbenzyl isobutyl ether
- 3-methylphenyl-CH2CH2-O-CH3
- 3-methylphenyl-CH2CH2-O-CH2CH3
- 3-methylphenyl-CH2CH2-O-CH(CH3)2
- 3-methylphenyl-CH2CH2-O-CH2CH2CH3
- 3,5-disubstituted phenyl with CH2-O-CH3 and OCH3
- 2-(methoxymethyl)-4-methylphenol
- 2-(2-ethoxyethyl)-4-methylphenol TABLE 8-continued (8) [Cyclopentanone structure with side chains terminating in COOH and R⁵, with OH substituent]

R⁵:
- 2,4-dimethylphenol
- 2-ethyl-4-methylphenol
- 4-methyl-2-propylphenol
- 3-methylbenzyl alcohol
- 1-(2-fluoroethyl)-3-methylbenzene

TABLE 9

(9) [Cyclopentane structure with Cl and OH substituents, side chains terminating in COOH and R⁵, with OH]

R⁵:
- 1-(methoxymethyl)-3-methylbenzene
- 1-(ethoxymethyl)-3-methylbenzene
- 1-methyl-3-(propoxymethyl)benzene
- 1-(isobutoxymethyl)-3-methylbenzene TABLE 9-continued (9) [Cyclopentane structure with Cl and OH substituents, side chains terminating in COOH and R⁵, with OH]

R⁵:
- 1-(2-methoxyethyl)-3-methylbenzene
- 1-(2-ethoxyethyl)-3-methylbenzene
- 1-(2-isopropoxyethyl)-3-methylbenzene
- 1-methyl-3-(2-propoxyethyl)benzene
- 1,3-bis(methoxymethyl)-5-methylbenzene
- 2-(methoxymethyl)-4-methylphenol
- 2-(2-ethoxyethyl)-4-methylphenol
- 2,4-dimethylphenol
- 2-ethyl-4-methylphenol
- 4-methyl-2-propylphenol
- 3-methylbenzyl alcohol TABLE 9-continued
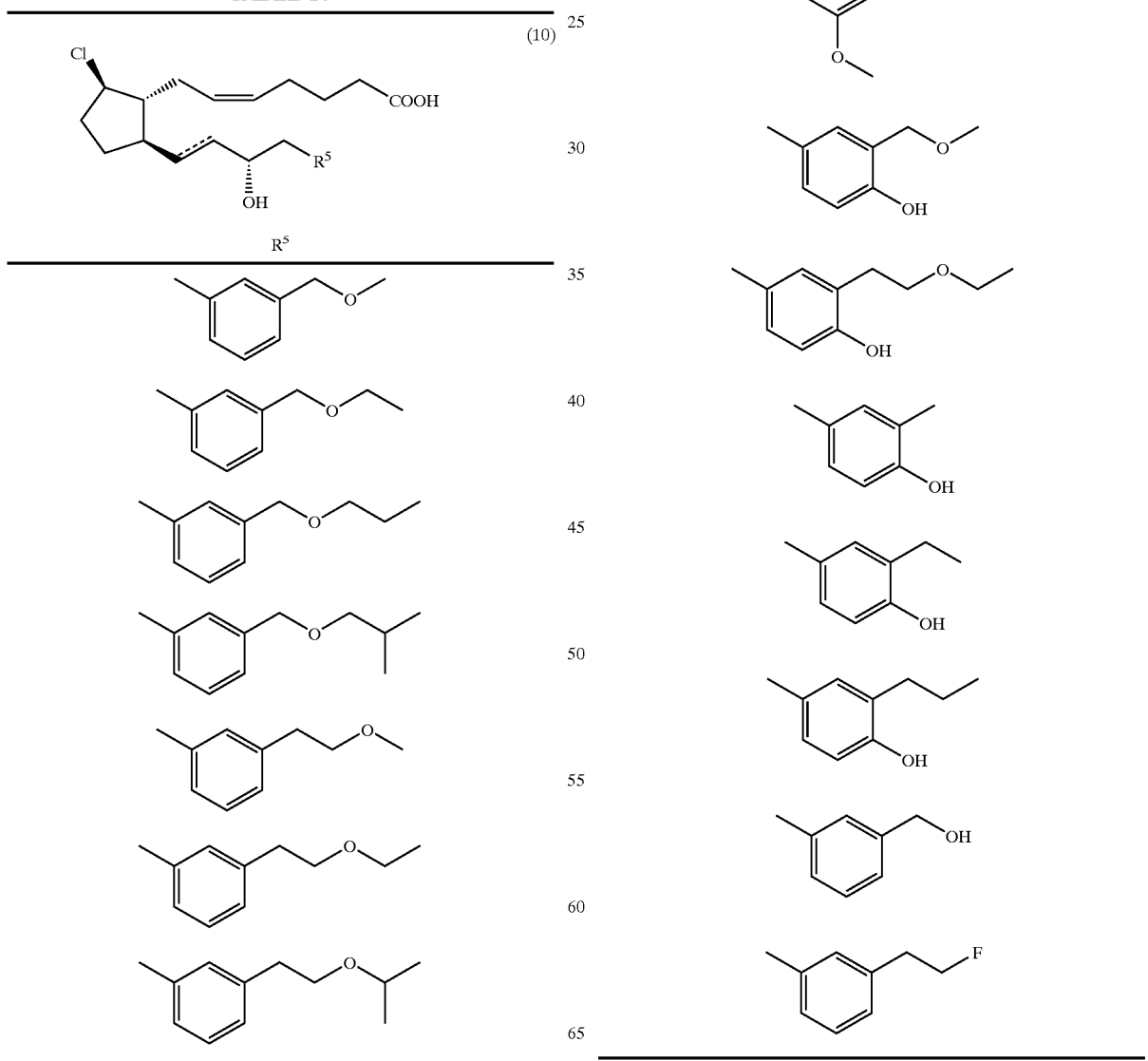
TABLE 10

TABLE 11
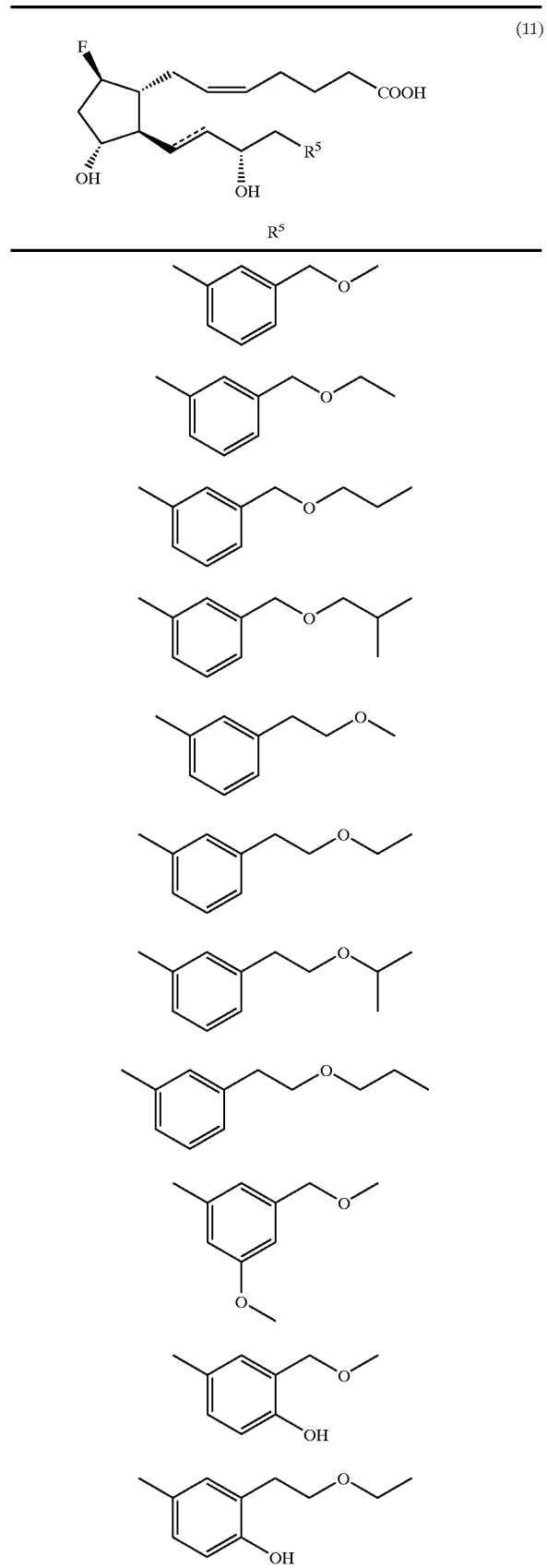
TABLE 11-continued
TABLE 12
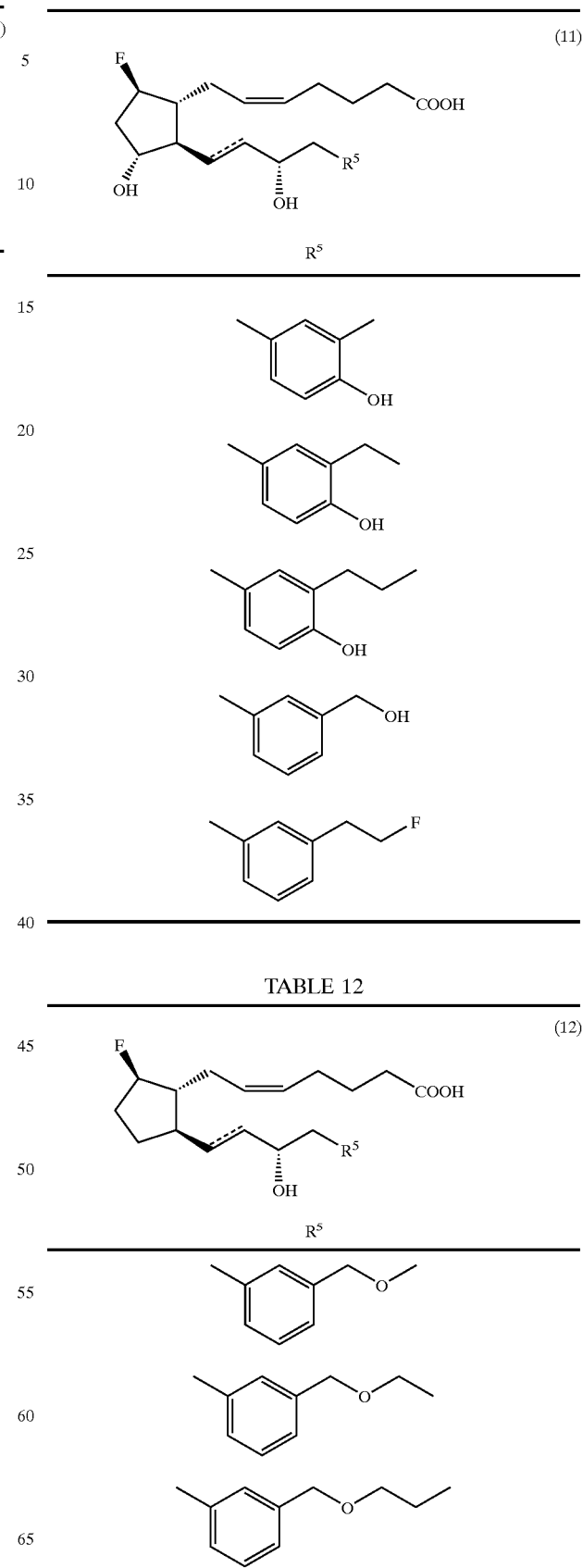

TABLE 12-continued
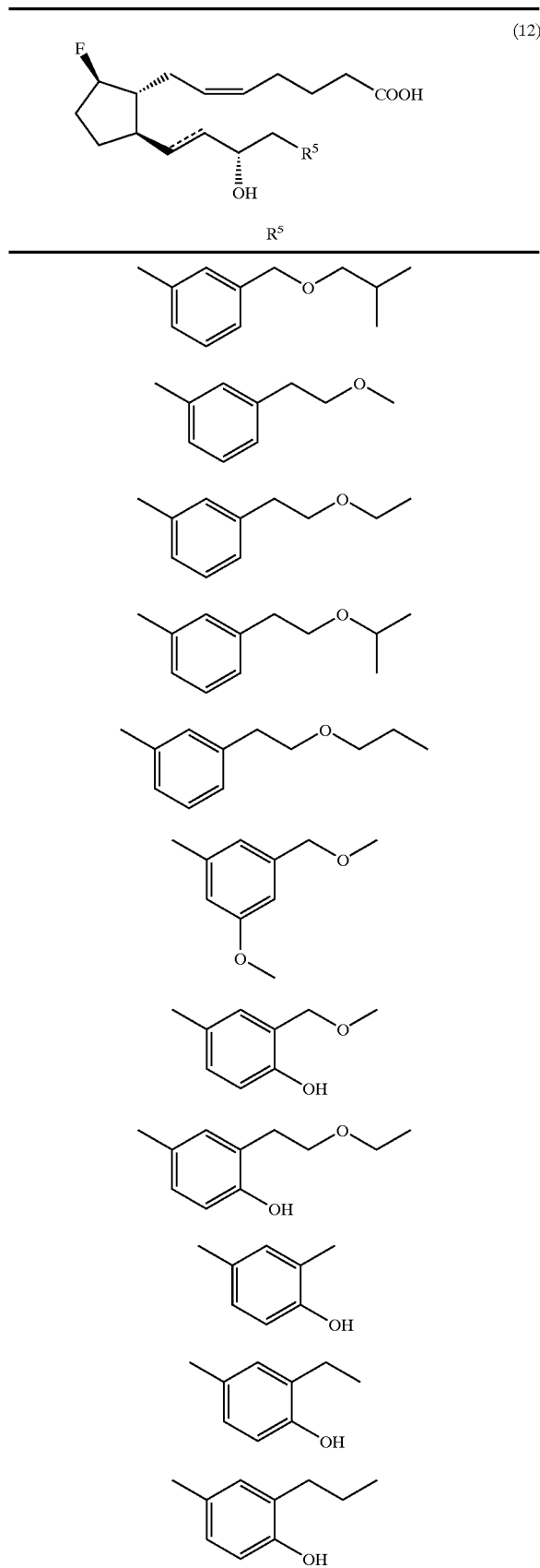
TABLE 12-continued
TABLE 13
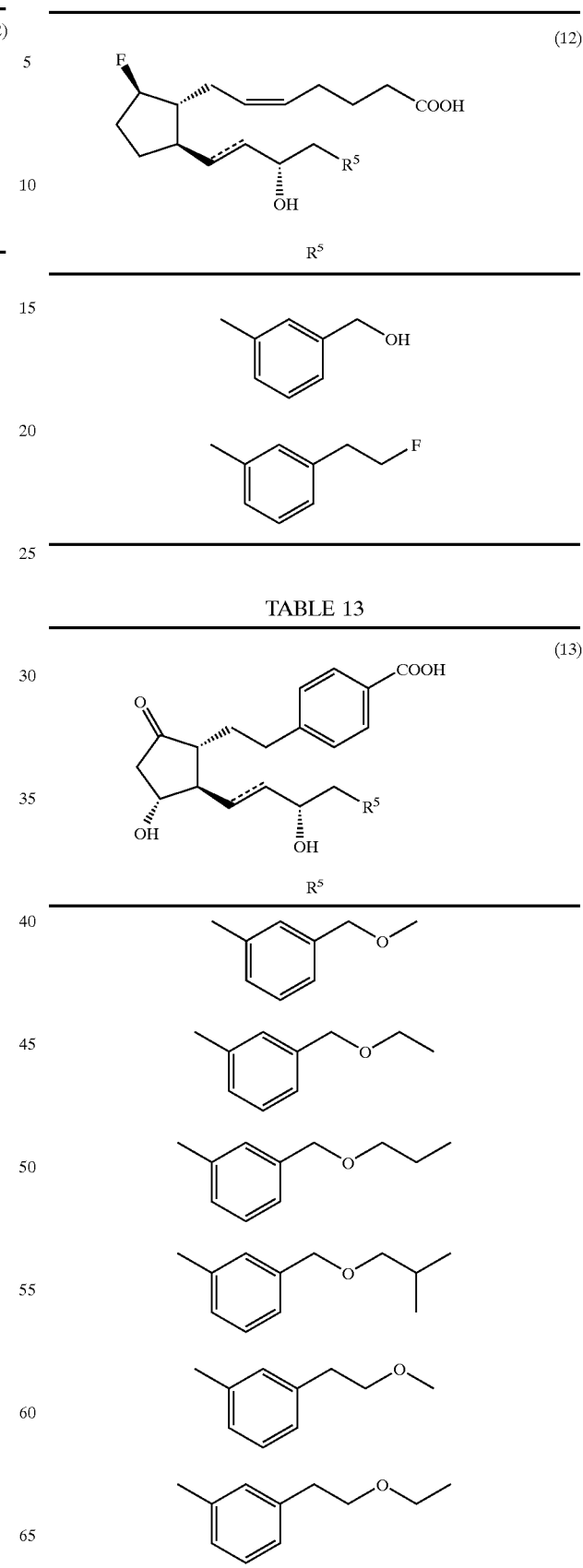

TABLE 13-continued (13)

TABLE 14

(14)

TABLE 14-continued
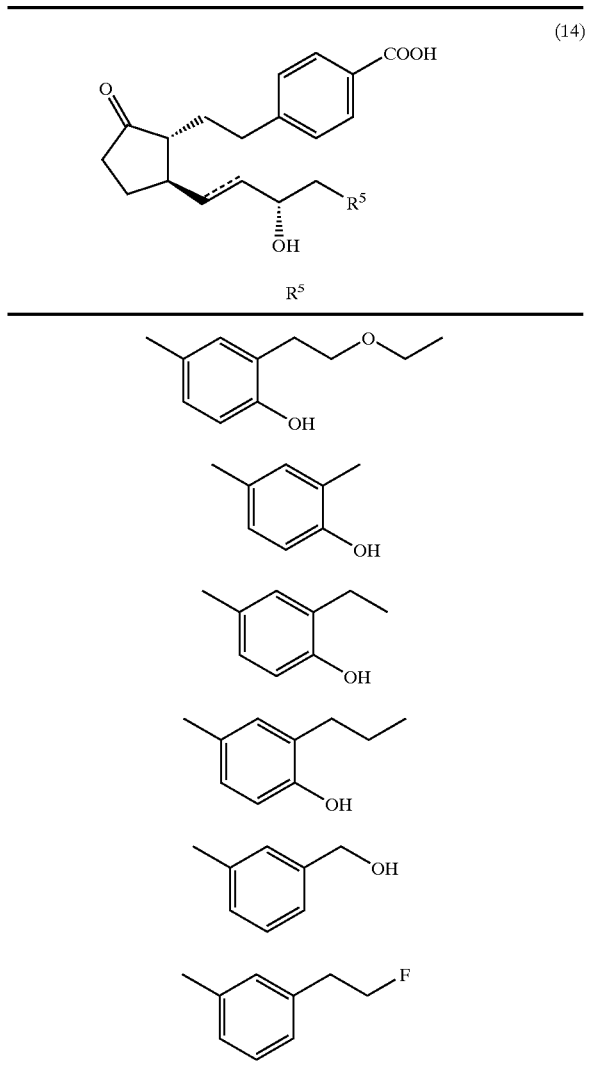
TABLE 15
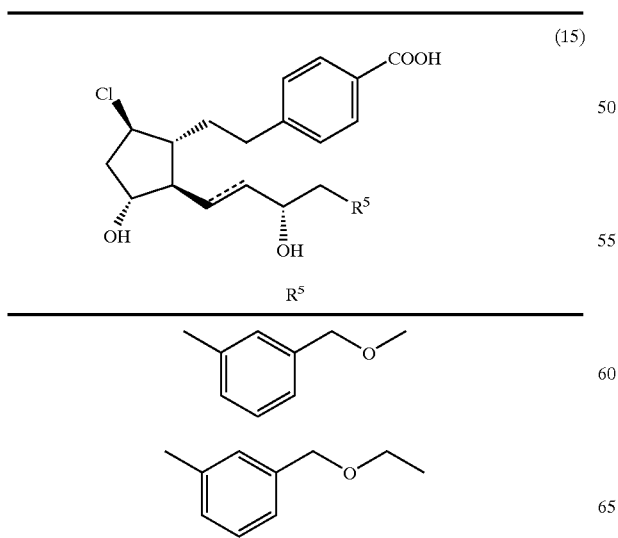
TABLE 15-continued
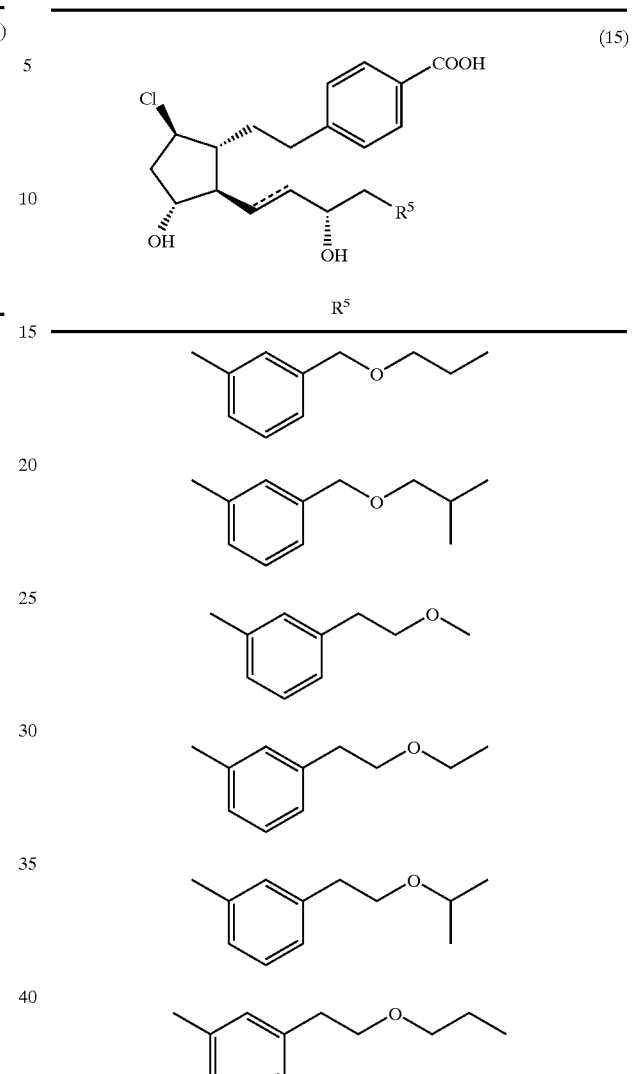
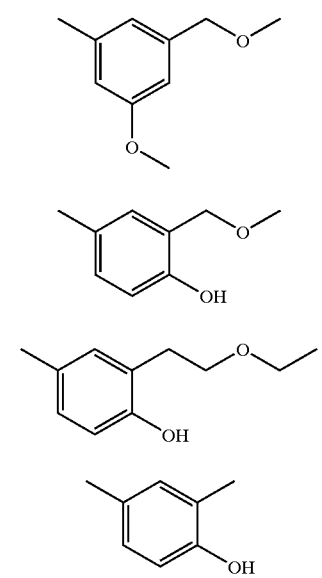

TABLE 15-continued
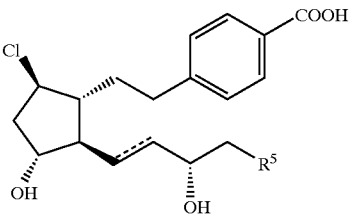
| R⁵ |
|---|
| 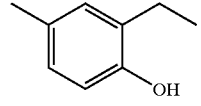 |
| 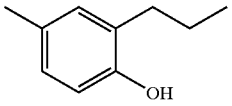 |
| 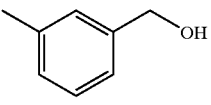 |
| 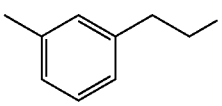 |
TABLE 16
| R⁵ |
|---|
| 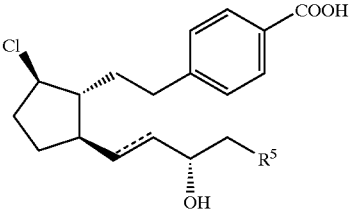 |
| 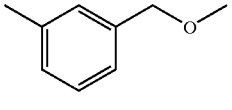 |
| 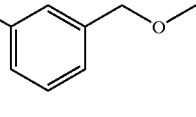 |
| 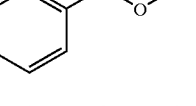 |
TABLE 16-continued
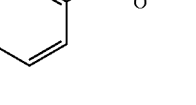
| R⁵ |
|---|
| 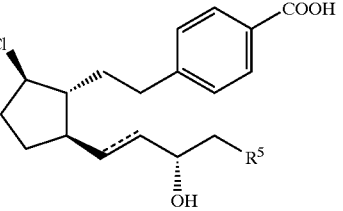 |
| 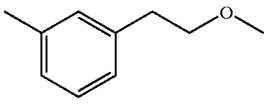 |
| 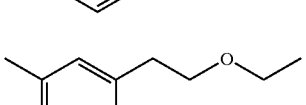 |
| 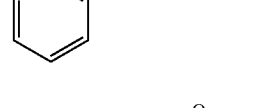 |
| 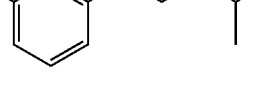 |
| 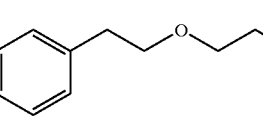 |
| 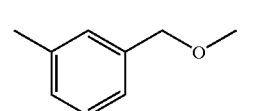 |

TABLE 16-continued (16)

| R⁵ |
|---|
| *3-(hydroxymethyl)phenyl-methyl* |
| *3-(2-fluoroethyl)phenyl-methyl* |

TABLE 17

(17)

| R⁵ |
|---|
| *3-(methoxymethyl)phenyl-methyl* |
| *3-(ethoxymethyl)phenyl-methyl* |
| *3-(propoxymethyl)phenyl-methyl* |
| *3-(isobutoxymethyl)phenyl-methyl* |
| *3-(2-methoxyethyl)phenyl-methyl* |
| *3-(2-ethoxyethyl)phenyl-methyl* |

TABLE 17-continued (17)

| R⁵ |
|---|
| *3-(2-isopropoxyethyl)phenyl-methyl* |
| *3-(2-propoxyethyl)phenyl-methyl* |
| *3,5-dimethoxy-methylphenyl* |
| *4-hydroxy-3-(methoxymethyl)-tolyl* |
| *4-hydroxy-3-(2-ethoxyethyl)-tolyl* |
| *4-hydroxy-2,3-dimethylphenyl* |
| *3-ethyl-4-hydroxy-tolyl* |
| *4-hydroxy-3-propyl-tolyl* |
| *3-(hydroxymethyl)phenyl-methyl* |
| *3-(2-fluoroethyl)phenyl-methyl* |

TABLE 18

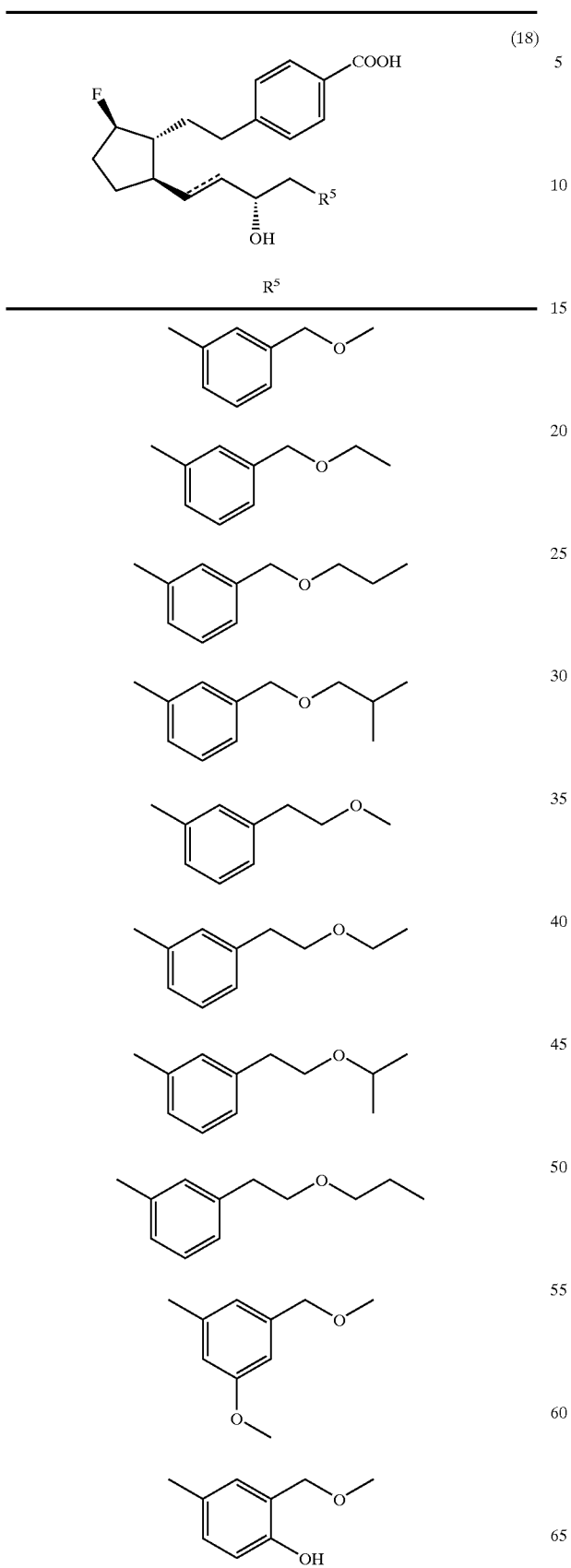

TABLE 18-continued

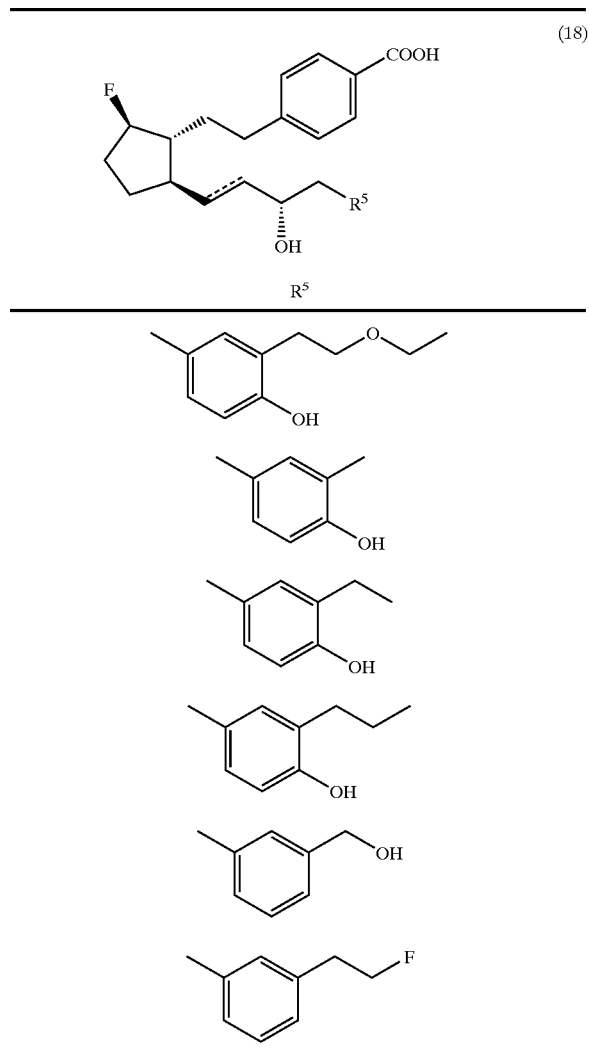

Salts

The compounds of the present invention of formula (I) may be converted into the corresponding salts by conventional methods. Non-toxic and water-soluble salts are preferable. Appropriate salts are described hereafter; salts of alkali metals (e.g. potassium, sodium), salts of alkaline-earth metals (e.g. calcium, magnesium), ammonium salts, salts of pharmaceutically acceptable organic amines (e.g. tetramethyl ammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine).

Cyclodextrin Clathrates

ω-Substituted phenyl-prostaglandin E derivatives of formula (I) may be converted into cyclodextrin clathrates using α-, β- or γ-cyclodextrin or a mixture thereof, by the methods described in the specification of Japanese Kokoku No. 50-3362, ibid. 52-31404 (i.e. GB Patent Nos. 1351238, 1419221) or Japanese Kokoku No. 61-52146. Converting them into cyclodextrin clathrates serves to increase the stability and solubility in water, and therefore it is convenient for pharmaceutical use.

Processes for the preparation of the compounds of the present invention (a) Among the compounds of formula (I), a compound wherein $R^1$ is C1~6 alkyloxy, C1~6 yloxy-C1~6 alkyloxy or HO—C1~6 alkyloxy, i.e. a compound of formula (Ia)

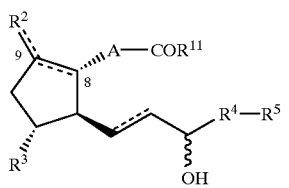
(Ia)

(wherein $R^{11}$ is C1~6 alkyloxy, C1~6 alkyloxy-C1~6 alkyloxy or HO—C1~6 alkyloxy and the other symbols have the same meanings as described hereinbefore) may be prepared by subjecting to a deprotection reaction under acidic conditions a compound of formula (II)

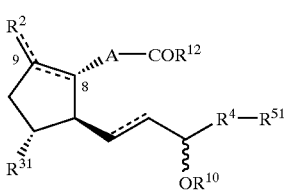
(II)

(wherein $R^{12}$ is C1~6 alkyloxy, C1~6 alkyloxy-C1~6 alkyloxy or (a protective group for hydroxy removable under acidic conditions)-O—C1~6 alkyloxy, $R^{31}$ is hydrogen or a protected form of hydroxy in which the protective group is removable under acidic conditions, $R^{10}$ is a protective group for hydroxy removable under acidic conditions, $R^{51}$ has the same meaning as $R^5$, but hydroxy in the group of $R^{51}$ is protected by a protective group removable under acidic conditions and the other symbols have the same meanings as described hereinbefore).

Protective groups for hydroxy removable under acidic conditions include, for example, t-butyldimethylsilyl, triphenylmethyl, tetrahydropyran-2-yl, etc.

Hydrolysis under acidic conditions is known, for example, it is carried out in a water-miscible organic solvent (e.g. tetrahydrofuran, methanol, ethanol, dimethoxyethane, acetonitrile or a mixture thereof, etc.), using inorganic acid (e.g. hydrochloric acid, phosphoric acid, hydrofluoric acid, hydrochloric acid-pyridine, etc.) or an organic acid (e.g. acetic acid, tosyl acid, trichloroacetic acid, etc.) at a temperature of 0~50° C.

(b) Among the compounds of formula (I), a compound wherein $R^1$ is hydroxy, i.e. a compound of formula (Ib)

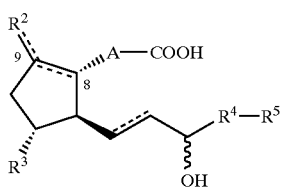
(Ib)

(wherein all symbols have the same meaning as described hereinbefore) may be prepared by subjecting to hydrolysis reaction using an enzyme or a hydrolysis reaction under alkaline conditions a compound of formula (Ia)

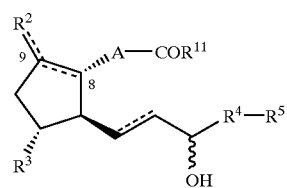
(Ia)

(wherein all symbols have the same meaning as described hereinbefore). Hydrolysis using an enzyme is known, for example, it may be carried out in a mixture of water-miscible organic solvent (e.g. ethanol, dimethylsulfoxide, etc.) and water, in the presence or absence of a buffer, using hydrolase (esterase, lipase etc.) at a temperature of 0~50° C.

Hydrolysis under alkaline conditions is known, for example, it may be carried out in a mixture of a water-miscible organic solvent (e.g. ethanol, tetrahydrofuran (THF), dioxane, etc.) using an aqueous solution of an alkali (sodium hydroxide, potassium hydroxide, potassium carbonate, etc.) at a temperature of –10~90° C.

(c) Among the compounds of formula (I), a compound wherein $R^1$ is $NR^6R^7$, i.e. a compound of formula (Ic)

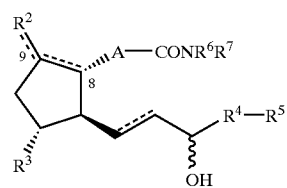
(Ic)

(wherein all symbols have the same meaning as described hereinbefore) may be prepared by subjecting to an amidation reaction a compound of formula (Ib)

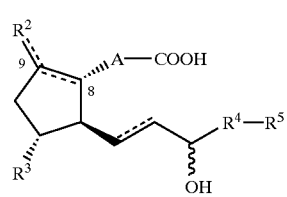
(Ib)

(wherein all symbols have the same meaning as described hereinbefore) and a compound of formula (III)

$HNR^6R^7$ (III)

(wherein all symbols have the same meaning as described hereinbefore).

Amidation reaction is known, for example, it is carried out in an inert organic solvent (e.g. THF, methylene chloride, benzene, acetone, acetonitrile or a mixture thereof, etc.) in the presence or absence of a tertiary amine (dimethylaminopyridine, pyridine, triethylamine, etc.), using a condensing reagent (1,3-dichlorohexylcarbodiimide (DCC), 1-ethyl-3-[3-(dimethylamino)propyl]carbodiimide (EDC), etc.) at a temperature of 0~50° C.

The compound of formula (III) is a known compound or may be prepared by known methods easily.

The compound of formula (II) may be prepared according to the following schemes 1, 2, 3 or 6.

Moreover, the compounds of formula (Ia), (Ia-1) and (Ib) may be synthesized by the schemes 4 or 5.

The symbols described in the schemes have the following meaning or the same meaning as described hereinbefore:

t-Bu: t-butyl,
Ms: methanesulfonyl,
n-Bu: normal butyl,
Ts: p-toluenesulfonyl,
X: halogen atom,
$R^{21}$: halogen atom,
$R^{22}$: acyl,
$A^1$: C1~7 alkylene, C2~7 alkenylene,
C1~3 alkylene-phenylene or C2~3 alkenylene-phenylene,
$A^2$: C2~8 alkylene or C1~4 alkylene-phenylene.

In each scheme, the process for the preparation of 15α isomer is illustrated, but 15β isomer and a mixture of 15α and 15β isomers may be also synthesized depending on the choice of reduction method, with or without separation, depending on the choice of starting materials Scheme 1

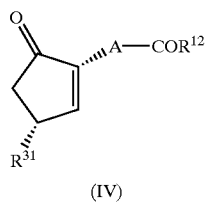

(IV)

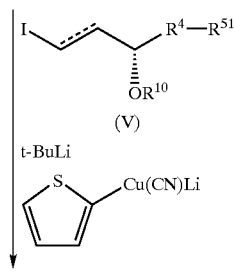

(V)

t-BuLi

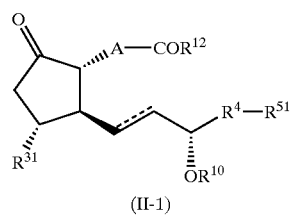

(II-1)

Scheme 2

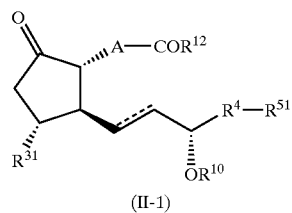

(II-1)

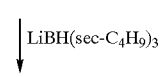
LiBH(sec-$C_4H_9$)$_3$

-continued

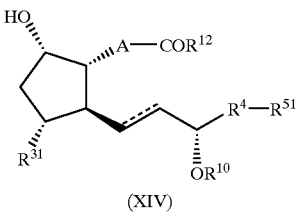

(XIV)

TsCl

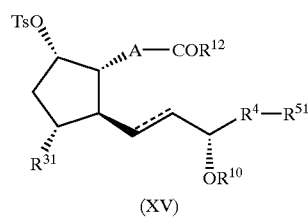

(XV)

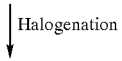
Halogenation

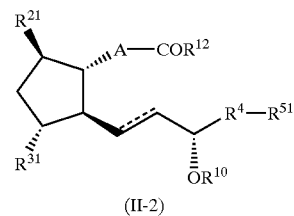

(II-2)

Scheme 3

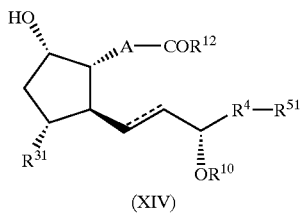

(XIV)

HCOOH

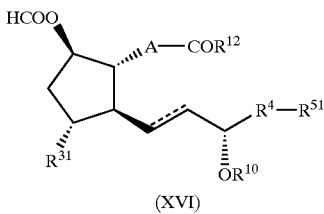

(XVI)

$NH_3$

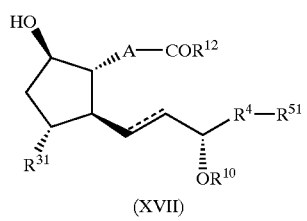
(XVII)
↓ TsCl
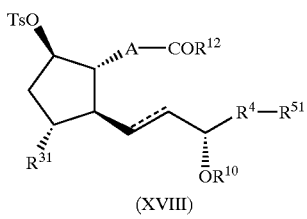
(XVIII)
↓ Halogenation
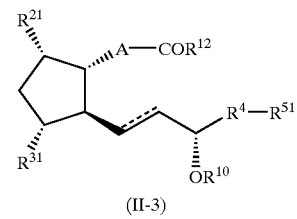
(II-3)
Scheme 4-1
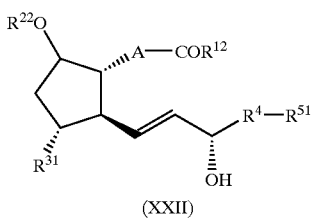
(XXII)
↓ Protection of hydxory
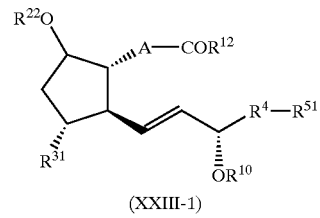
(XXIII-1) → To Scheme 4-3
Scheme 4-2
(XXI)
Ph₃SnH or Bu₃SnH  ↙    ↘  H₂/Pd
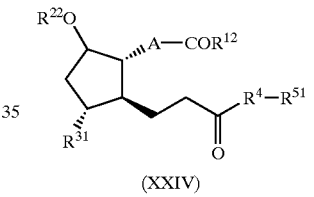 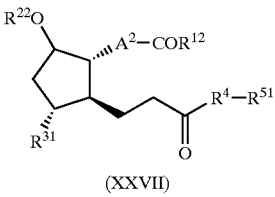
(XXIV)    (XXVII)
↓ NaBH₄ Reduction    ↓ NaBH₄ Reduction
(XXV)    (XXVIII)
↓ Separation    ↓ Separation
(XXVI)    (XXIX)
↓ Protection of hydroxy    ↓ Protection of hydroxy -continued
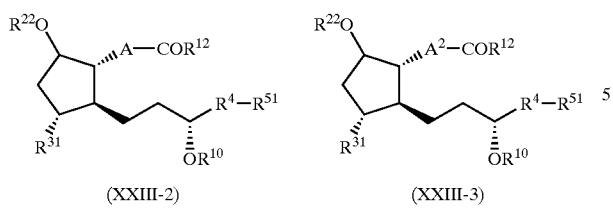
(XXIII-2)  (XXIII-3)
To Scheme 4-3    To Scheme 4-3
Scheme 4-3
(XXIII-1) (XXIII-2) (XXIII-3)
↓ OH⁻
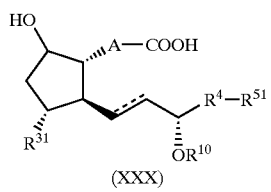
(XXX)
↓ Jones oxidation
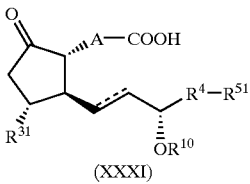
(XXXI)
↓ H⁺
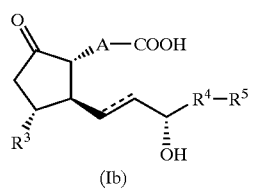
(Ib)
↓ Esterification
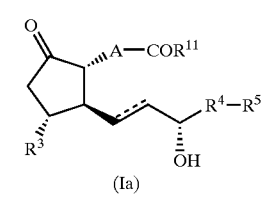
(Ia)
Scheme 5
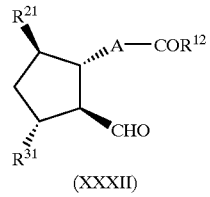
(XXXII)
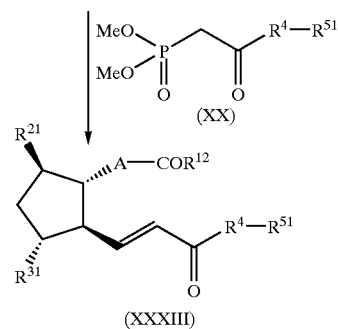
(XXXIII)
↓ Selective Reduction
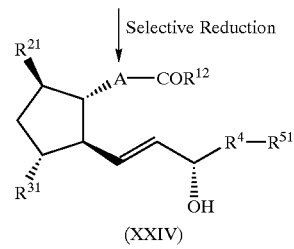
(XXIV)
↓ H⁺
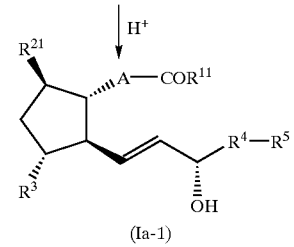
(Ia-1)
Scheme 6
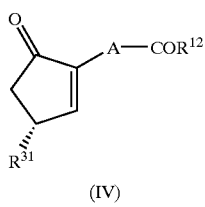
(IV)
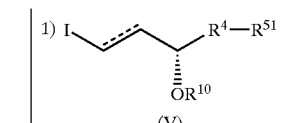
(V)
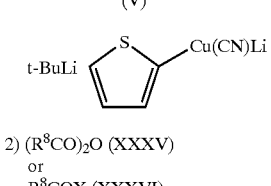
2) (R⁸CO)₂O (XXXV)
or
R⁸COX (XXXVI)
↓

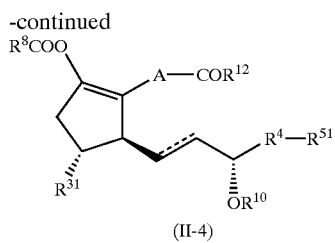

(II-4)

Scheme 7

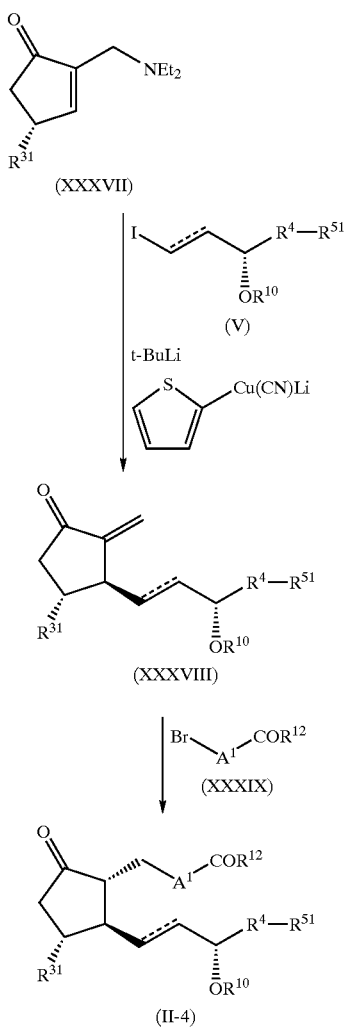

Starting Materials and Reagents

Each reaction in the above reaction schemes is carried out by known methods. In the above reaction schemes, the compounds of formulae (IV), (V), (XIX), (XIX), X(X), (XXXII) and (XXXVII) are known per se or may be prepared by known methods easily. For example, among the compounds of formula (IV), a compound wherein $R^{31}$ is tetramethylsilyloxy, A is hexenylene and $R^{12}$ is ethoxy is described in JP kokai sho 58-39660 (i.e. U.S. Pat. No. 4,363,817); among the compounds of formula (XIX), a compound wherein $R^{12}$ is methoxy, $R^{22}$ is acetyl, $R^{31}$ is 2-tetrahydropyranyloxy and A is hexenylene is described in JP kokai sho 52-27753 (i.e. U.S. Pat. No. 4,180,675). The other starting materials and reagents in the present invention are known per se or may be prepared by known methods.

In each reaction of the present specification, reaction products may be purified by conventional techniques. For example, purification may be carried out by distillation under atmospheric or reduced pressure, by high performance liquid chromatography, thin layer chromatography or column chromatography using silica gel or magnesium silicate, by washing or by recrystallization, etc. Purification may be carried out after each reaction, or after a series of reactions.

Pharmacological Activities

The compounds of the present invention of formula (I) bind strongly and act on $EP_4$ receptor which is $PGE_2$ receptor subtype.

For example, in the laboratory the effects of the compounds of the present invention were confirmed by binding assay using expression cell of prostanoids receptor subtype.

(i) Binding assay using Expression cell of prostanoids receptor subtype

The preparation of membrane fraction was carried out according to the method of Sugimoto et al. [J. Biol. Chem., 267, 6463–6466 (1992)], using expression CHO cell of the prostanoids receptor subtype (mouse $EP_1$, $EP_2$, $EP_{3\alpha}$, $EP_4$ and human IP).

The standard assay mixture containing membrane fraction (0.5 mg/ml) and [$^3$H]-$PGE_2$ in a final volume of 200 µl was incubated for 1 hour at room temperature. The reaction was terminated by addition of ice-cooled buffer (3 ml). The mixture was filtered through a GF/B glass filter under reduced pressure. The radioactivity associated with the filter was measured by liquid scintillation counting.

Kd and Bmax values were determined from Scatchard plots [Ann. N. Y. Acad. Sci., 51, 660 (1949)]. Non-specific binding was calculated as the binding in the presence of an excess (2.5 µM) of unlabeled $PGE_2$. In the measurement of $^3$H-$PGE_2$ binding inhibitory activity, [3H]-$PGE_2$ (2.5 nM) and various concentrations of the compounds of the present invention were added. The following buffer was used in all reactions.

Buffer ; 10 mM potassium phosphate (pH 6.0), 1 mM EDTA, 10 mM $MgCl_2$, 0.1 M NaCl.

The dissociation constant Ki (µM) of each compound was calculated by the following equation.

$$Ki=IC_{50}/(1+([C]/Kd));$$

The results are shown in the Tables 19 and 20.

TABLE 19

| Ex. No. | Dissociation Constant Ki (µM) EP4 |
|---|---|
| 2 | 0.006 |
| 2 (1) | 0.0016 |
| 2 (4) | 0.003 |
| 2 (11) | 0.010 |
| 2 (15) | 0.0026 |
| 4 | 0.0036 |
| 4 (12) | 0.0059 |
| 5 (12) | 0.008 |
| 8 (6) | 0.0015 |
| The compound described as example 55 in JP kokai sho 49-92053 | 0.032 |

TABLE 19-continued

| Ex. No. | Dissociation Constant Ki (μM) EP4 |
|---|---|
| The compound described as example 72 in JP kokai sho 49-92053 | 0.067 |

TABLE 20

| Ex. No. | Dissociation Constant Ki (μM) $EP_{3\alpha}$ |
|---|---|
| 2 | 0.82 |
| 2 (1) | 0.12 |
| 2 (4) | >10 |
| 2 (11) | 0.54 |
| 2 (15) | 1.40 |
| 4 | 3.20 |
| 4 (12) | 0.35 |
| 5 (12) | 6.0 |
| 8 (6) | 0.04 |
| The compound described as example 55 in JP kokai sho 49-92053 | 0.011 |
| The compound described as example 72 in JP kokai sho 49-92053 | 0.048 |

As shown above, it is clear that the compounds of the present invention bind strongly on subtype $EP_4$ and weakly on the other $PGE_2$ receptors (e.g. $EP_3$).

Toxicity

The toxicity of the compounds of the present invention is very low and therefore, it is confirmed that these compounds are safe for pharmaceutical use.

INDUSTRIAL APPLICABILITY

Application to Pharmaceuticals

The compounds of the present invention of formula (I) bind selectively and act on $PGE_2$ receptor, especially on $EP_4$ subtype receptor and therefore are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burn, systemic granuloma, ulcerative colititis, Crohn's diseases, hypercytokinemia at dialysis, multiple organ failure, shock, etc. They are also connected with sleeping disorders and platelet coagulations, and therefore they are thought to be useful for these diseases.

Among the compounds of the present invention of formula (I), the compounds which bind on other subtypes than $EP_4$ weakly do not express other effect, and therefore it is probable that they will be those agents having less adverse effects.

For the purpose described hereinbefore, the compounds of the present invention of formula (I), non-toxic salts thereof and CD clathrates thereof may normally be administered systemically or topically, by oral or parenteral administration.

The doses to be administered are determined depending upon age, body weight, symptom, the desired therapeutic effect, the route of administration, and the duration of the treatment etc. In the human adult, the doses per person per dose are generally from 1 μg to 100 mg, by oral administration, from once up to several times per day, and from 0.1 μg to 10 mg, by parenteral administration (preferably intravenously) from once up to several times per day, or by continuous administration for from 1 hour to 24 hours per day into vein.

As mentioned hereinbefore, the doses to be administered depend upon various conditions. Therefore, there are cases in which doses lower than or greater than the ranges specified hereinbefore may be used.

The compounds of the present invention may be administered in the form, for example, of solid compositions, liquid compositions or other compositions for oral administration, or injections, liniments or suppositories etc. for parenteral administration.

Solid compositions for oral administration include compressed tablets, pills, capsules, dispersible powders, and granules etc.

Capsules include hard capsules and soft capsules.

In these solid compositions, one or more of the active compound(s) are admixed with at least one inert diluent, e.g. lactose, mannitol, mannit, glucose, hydroxypropyl cellulose, microcrystalline cellulose, starch, polyvinyl pyrrolidone, magnesium metasilicate aluminate. The composition may comprise, according to the conventional manner, additives other than inert diluents, e.g. lubricating agents such as magnesium stearate, disintegrating agents such as cellulose calcium glycolate, agents to assist dissolution such as glutamic acid, aspartic acid. The tablets or pills may, if desired, be coated with film of gastric or enteric material such as sugar, gelatin, hydroxypropyl cellulose, hydroxypropyl cellulose phthalate etc. or be coated with more than one film. Coating may include containment within capsules of absorbable materials such as gelatin.

Liquid compositions for oral administration include pharmaceutically acceptable emulsions, solutions, syrups and elixirs etc. In such liquid compositions, one or more of the active compound(s) may be contained in inert diluent(s) commonly used in the art (e.g. purified water, ethanol). Besides inert diluents, such compositions may also comprise assisting agents (e.g. wetting agents, suspending agents), sweetening agents, flavoring agents, perfuming agents and preserving agents.

Other compositions for oral administration include spray compositions which comprise one or more of the active compound(s), prepared by methods known per se. Spray compositions may comprise stabilizing agents such as sodium sulfite hydride, isotonic buffers such as sodium chloride, sodium citrate or citric acid. For the preparation of such spray compositions, for example, the method described in the U.S. Pat. No. 2,868,691 or U.S. Pat. No. 3,095,355 may be used.

Injections for parenteral administration include sterile aqueous or non-aqueous solutions, suspensions and emulsions. Aqueous solutions and suspensions include, for example, distilled water for injection and physiological salt solution. Non-aqueous solution and suspensions include, for example, propylene glycol, polyethylene glycol, vegetable oil such as olive oil, alcohol such as ethanol, POLYSOR- BATE80 (registered trademark) etc. These compositions may comprise assisting agents such as preserving agents, wetting agents, emulsifying agents, dispersing agents, stabilizing agents, agents assisting dissolution (e.g. glutamic acid, aspartic acid etc.). They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile solvent(s) for injection before use.

Other compositions for parenteral administration include liquids for external use, and ointment, endermic liniments, suppositories for rectal administration and pessaries for vaginal administration etc. which comprise one or more of active compound(s) and may be prepared by conventional methods.

The Best Mode for Carrying Out the Present Invention

The following reference examples and examples are intended to illustrate, but do not limit, the present invention. The solvents in parentheses show the developing or eluting solvents and the ratios of the solvents used are by volume in chromatographic separations. The solvents in the parenthesis of NMR show the solvents used for measurement.

REFERENCE EXAMPLE 1

1-bromo-3-methoxymethylbenzene

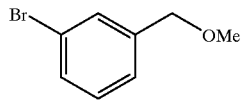

To a solution of 3-bromobenzylbromide (15.0 g) in methanol-dimethoxyethane (30 ml+10 ml) was added sodium methylate (4.9 g) under cooling with ice and the mixture was stirred for 1 hour at room temperature. The reaction mixture was poured into water. The reaction mixture was extracted with ether. The organic layer was washed with a saturated aqueous solution of sodium chloride, dried over anhydrous magnesium sulfate and the solvent was evaporated to give the title compound (12.1 g) having the following physical data.

TLC: Rf 0.74 (ethyl acetate:hexane=1:4); NMR (CDCl$_3$): δ 7.50 (s, 1H), 7.42 (dt, J=8, 2 Hz, 1H), 7.3–7.2 (m, 2H), 4.43 (s, 2H), 3.40 (s, 3H).

REFERENCE EXAMPLE 2

(2S)-3-(3-Methoxymethylphenyl)-1-triphenylmethoxypropan-2-ol

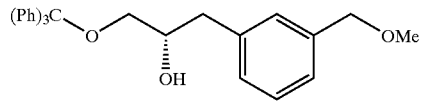

Magnesium ribbon (1.41 g) was dried by heating under reduced pressure, and thereto was added anhydrous THF (30 ml) and dibromoethane (a few drops). To the mixture was added a solution of the compound prepared in reference example 1 (9.65 g) in anhydrous THF (30 ml) over a period of 45 minutes. Thus obtained solution was added to a suspension of copper iodide (0.76 g) in anhydrous THF (30 ml) under cooling with ice, and the mixture was stirred for 30 minutes. To the mixture was added a solution of S-(−)-glycidyl trityl ether (12.7 g) in anhydrous THF (30 ml) and the mixture was stirred for 1 hour and the mixture was poured into a saturated aqueous solution of ammonium chloride. The mixture was extracted with ethyl acetate. The organic layer was washed with a saturated aqueous solution of sodium chloride, dried over anhydrous magnesium sulfate, concentrated to give the title compound (19.5 g) having the following physical data.

TLC: Rf 0.29 (ethyl acetate:hexane=1:4); NMR (CDCl$_3$): δ 7.5–7.1 (m, 19H), 4.40 (s, 2H), 4.1–3.9 (m, 1H), 3.37 (s, 3H), 3.3–3.1 (m, 2H), 2.9–2.7 (m, 2H), 2.23 (br, 1H).

REFERENCE EXAMPLE 3

(2S)-3-(3-Methoxymethylphenyl)propan-1,2-diol

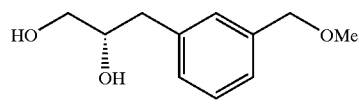

To a solution of the compound prepared in reference example 2 (19.5 g) in THF (10 ml) was added acetic acid (80 ml) and water (10 ml) and the mixture was heated to 60° C. and stirred for 6 hours. To the mixture was added water (40 ml) and the mixture was cooled to room temperature, and the precipitate was removed by filtration. The filtrate was concentrated. The precipitate was removed again and the mixture was concentrated. From the obtained oil, the solvent was separated as azeotropic mixture with toluene to give the title compound (8.9 g) having the following physical data.

TLC: Rf 0.64 (ethyl acetate:hexane=2:1).

REFERENCE EXAMPLE 4

(2S)-3-(3-Methoxymethylphenyl)-1-acetyloxypropan-2-ol

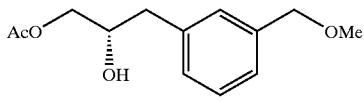

A solution of the compound prepared in reference example 3 (8.9 g) and 2,4,6-collidine (10.6 ml) in methylene chloride (120 ml) was cooled to −70° C. and thereto was added acetyl chloride (4.0 ml) dropwise. The mixture was stirred for 15 minutes and thereto was added methanol and the mixture was allowed to warm to 0° C. The mixture was washed with a 1 N hydrochloric acid and a saturated aqueous solution of sodium chloride, dried over anhydrous magnesium sulfate, concentrated to give the title compound (10.8 g) having the following physical data.

TLC: Rf 0.64 (ethyl acetate:hexane=2:1); NMR (CDCl$_3$): δ 7.4–7.1 (m, 4H), 4.43 (s, 2H), 4.25–3.95 (m, 3H), 3.41 (s, 3H), 2.9–2.8 (m, 2H), 2.12 (s, 3H).

REFERENCE EXAMPLE 5

(2S)-3-(3-Methoxymethylphenyl)-1-acetyloxy-2-(2-tetrahydropyranyloxy)propane

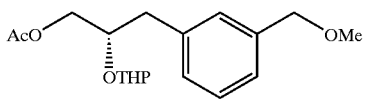

To a solution of the compound prepared in reference example 4 (10.8 g) in methylene chloride (40 ml) were added dihydropyran (5.5 ml) and pyridinium p-toluenesulfonate (0.50 g) and the mixture was stirred for 4 hours. The solution was concentrated and the residue was diluted with ethyl acetate. The mixture was washed with water and a saturated aqueous solution of sodium bicarbonate, dried over anhydrous sodium sulfate and concentrated. The residue was purified by column chromatography on silica gel to give the title compound (14.0 g) having the following physical data.

TLC: Rf 0.53 (ethyl acetate:hexane:methylene chloride= 1:2:2); NMR (CDCl$_3$): δ 7.3–7.1 (m, 4H), 4.85–4.8 and 4.45–4.0 (m, 1H), 4.43 (s, 2H), 4.25–3.85 and 3.5–3.2 (m, 5H), 3.39 (s, 3H), 3.05–2.8 (m, 2H), 2.10 and 2.08 (s, 3H), 1.9–1.4 (m, 6H).

REFERENCE EXAMPLE 6

(2S)-3-(3-Methoxymethylphenyl)-2-(2-tetrahydropyranyloxy)propan-1-ol

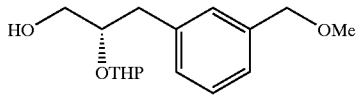

To a solution of the compound prepared in reference example 5 (14.0 g) in methanol (40 ml) was added a 2N aqueous solution of sodium hydroxide (5 ml) and the mixture was stirred for 1 hour at room temperature. The solvent was evaporated and the residue was diluted with ether, washed with water and a saturated aqueous solution of sodium chloride and dried over anhydrous magnesium sulfate. The mixture was concentrated. The resulting oil was purified by column chromatography on silica gel to give the title compound (11.0 g) having the following physical data.

TLC: Rf 0.51, 0.41 (diastereomeric mixture at the position of THP, ethyl acetate:hexane=2:1); NMR (CDCl$_3$): δ 7.3–7.1 (m, 4H), 4.85–4.8 and 4.25–4.2 (m, 1H), 4.42 (s, 2H), 4.05–3.4 (m, 5H), 3.38 (s, 3H), 3.06 (dd, J=14, 6 Hz, 1H), 2.85 (dd, J=14, 8 Hz, 1H), 2.8–2.7 and 2.15–2.05 (m, 1H), 1.9–1.4 (m, 6H).

REFERENCE EXAMPLE 7

(2S)-3-(3-Methoxymethylphenyl)-2-(2-tetrahydropyranyloxy)propan-1-al

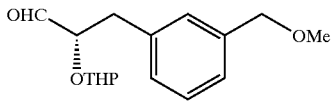

A solution of oxalyl chloride (6.8 ml) in methylene chloride (150 ml) was cooled to −78° C. and thereto was added a solution of anhydrous dimethylsulfoxide (11.1 ml) in methylene chloride (30 ml) over a period of 15 minutes. The mixture was stirred for 15 minutes and thereto was added a solution of the compound prepared in reference example 6 (11.0 g) in methylene chloride (40 ml) dropwise over a period of 35 minutes and the mixture was stirred for another 10 minutes and thereto was added triethylamine (32 ml). The mixture was warmed to −40° C. and stirred for 45 minutes. The reaction solution was poured into a 1 N hydrochloric acid and the mixture was extracted with a mixture of ether-hexane. The organic layer was washed with water, a saturated aqueous solution of sodium bicarbonate and a saturated aqueous solution of sodium chloride, dried over anhydrous magnesium sulfate and the solvent was evaporated to give the title compound (11.1 g) having the following physical data.

TLC: Rf 0.45 (ethyl acetate:hexane=1:2); NMR (CDCl$_3$): δ 9.75–9.0 (m, 1H), 7.3–7.1 (m, 4H), 4.8–4.75 and 4.35–4.3 (m, 1H), 4.43 (s, 2H), 4.45–4.3 and 4.1–4.0 (m, 1H), 3.95–3.9 and 3.5–3.4 (m, 1H), 3.40 (s, 3H), 3.3–2.8 (m, 3H), 1.9–1.3 (m, 6H).

REFERENCE EXAMPLE 8

(3S)-1,1-Dibromo-4-(3-methoxymethylphenyl)-3-(2-tetrahydropyranyloxy)-1-butene

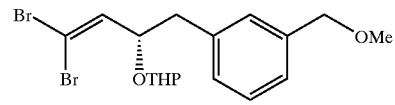

A solution of carbon tetrabromide (39.8 g) in methylene chloride (150 ml) was cooled to −20° C. and thereto was added a solution of triphenylphosphine (63 g) in methylene chloride (100 ml) over a period of 20 minutes. The obtained red sepia solution was cooled to −40° C. and thereto was added a solution of the compound prepared in reference example 7 (11.1 g) and triethylamine (5.6 ml) in methylene chloride (40 ml) dropwise. The mixture was stirred for 10 minutes and thereto was added triethylamine (11.7 ml) and methanol (9.8 ml). To a mixture of ether and hexane was added the above obtained sepia solution with stirring vigorously. The precipitate was filtered off and the filtrate was concentrated. The residue was purified by column chromatography on silica gel to give the title compound (13.6 g) having the following physical data.

TLC: Rf 0.36 (ethyl acetate:hexane=1:9).

REFERENCE EXAMPLE 9

(3S)-4-(3-Methoxymethylphenyl)-3-(2-tetrahydropyranyloxy)-1-butyne

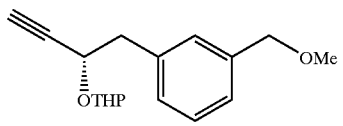

A solution of the compound prepared in reference example 8 (13.5 g) in anhydrous THF (90 ml) was cooled to −78° C. and thereto was added a solution of n-butyl lithium in hexane (1.61 M, 42.5 ml) over a period of 20 minutes. The mixture was stirred for 10 minutes and was poured into a saturated aqueous solution of ammonium chloride and was extracted with ethyl acetate. The organic layer was washed with a saturated aqueous solution of sodium chloride, dried over anhydrous sodium sulfate and the solvent was evaporated. The residue was purified by column chromatography on silica gel to give the title compound (8.9 g) having the following physical data.

TLC: Rf 0.50, 0.44 (ethyl acetate:hexane=1:4).

REFERENCE EXAMPLE 10

(3S)-4-(3-Methoxymethylphenyl)-1-butyn-3-ol

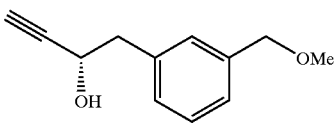

The compound prepared in reference example 9 (8.9 g) was dissolved in dioxane (10 ml) and methanol (10 ml), and to the mixture was added a 4N hydrochloric acid-dioxane (2 ml) at room temperature and the mixture was stirred for 1 hour. The reaction solution was diluted with water and the mixture was extracted with ethyl acetate. The organic layer was washed with a saturated aqueous solution of sodium bicarbonate and a saturated aqueous solution of sodium chloride, dried over anhydrous sodium sulfate and the solvent was evaporated. The residue was purified by column chromatography on silica gel to give the title compound (5.6 g) having the following physical data.

TLC: Rf 0.40 (ethyl acetate:hexane=1:2).

REFERENCE EXAMPLE 11

(3S)-4-(3-Methoxymethylphenyl)-3-t-butyldimethylsilyloxy-1-butyne

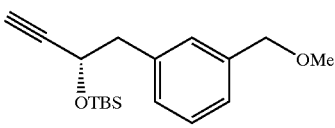

To a solution of the compound prepared in reference example 10 (5.64 g) and imidazole (3.0 g) in DMF (30 ml) was added t-butyldiethylsilyl chloride (5.3 g) and the mixture was stirred at room temperature overnight. The reaction mixture was poured into water, and the mixture was extracted with ethyl acetate. The organic layer was washed with water and a saturated aqueous solution of sodium chloride, dried over anhydrous magnesium sulfate and the solvent was evaporated. The residue was purified by column chromatography on silica gel to give the title compound (7.82 g) having the following physical data.

TLC: Rf 0.73 (ethyl acetate:hexane=1:4); NMR (CDCl$_3$): δ 7.3–7.1 (m, 4H), 4.5–4.45 (m, 1H), 4.44 (s, 2H), 3.37 (s, 3H), 3.0–2.95 (m, 2H), 2.41 (d, J=2 Hz, 1H), 0.83 (s, 9H), −0.02 (s, 3H), −0.08 (s, 3H).

REFERENCE EXAMPLE 12

(3S)-1-Iodo-4-(3-methoxymethylphenyl)-3-t-butyldimethylsilyloxy-1E-butene

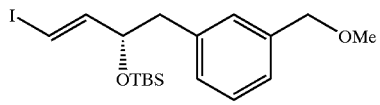

To a suspension of zirconocene chloride hydride (7.81 g) in anhydrous THF (15 ml) was added a solution of the compound prepared in reference example 11 (7.7 g) in THF (30 ml) dropwise at room temperature. The mixture was stirred for 45 minutes, cooled to 0° C. and thereto was added a solution of iodine (6.43 g) in THF dropwise. The mixture was stirred for 15 minutes at room temperature and thereto was added hexane. The obtained precipitate was filtered off and the filtrate was concentrated. The residue was purified by column chromatography on silica gel to give the title compound (9.77 g) having the following physical data.

TLC: Rf 0.61 (ethyl acetate:hexane=1:9); NMR (CDCl$_3$): δ 7.3–7.05 (m, 4H), 6.56 (dd, J=15, 5 Hz, 1H), 6.19 (dd, J=15, 1 Hz, 1H), 4.43 (s, 2H), 4.3–4.15 (m, 1H), 3.38 (s, 3H), 2.8–2.7 (m, 2H), 0.83 (s, 9H), −0.08 (s, 3H), −0.11 (s, 3H).

REFERENCE EXAMPLE 12 (1)

(3S)-1-Iodo-4-[3-(2-fluoroethyl)phenyl]3-t-butyldimethylsilyloxy-1E-butene

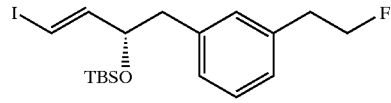

By the same procedures as described in reference example 2~12 using 3-(2-fluoroethyl)-bromobenzene, the above compound was synthesized.

REFERENCE EXAMPLE 13

(11α,15α)-9-oxo-11,15-bis(t-butyldimethylsilyloxy)-16-(3-methoxymethylphenyl)-17,18,19,20-tetranorprost-13E-enoic Acid Methyl Ester

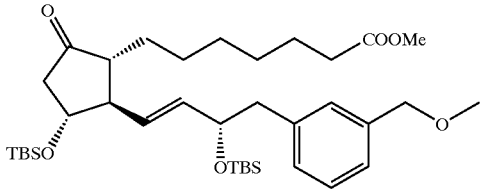

Under atmosphere of argon, to a solution of the compound synthesized in reference example 12 (1.27 g) in anhydrous diethyl ether (12 ml) was added t-butyl lithium (1.64 M solution in pentane, 3.58 ml) dropwise at −78° C. and the mixture was stirred for 40 minutes at the same condition. Thereto was added lithium 2-thienylcyanocuprate (0.25 M solution in tetrahydrofuran, 12.7 ml) dropwise over a period of 5 minutes and the obtained solution was stirred for another 20 minutes. Thereto was added a solution of 2-(6-methoxycarbonylhexyl)-4α-t-butyldimethylsilyloxy-2- cyclopenten-1-one (800 mg) in anhydrous tetrahydrofuran (4.5 ml, 0.5M) dropwise over a period of 10 minutes. The obtained solution was warmed to −40° C. over a period of 30 minutes and at the temperature the mixture was stirred for another 30 minutes. The reaction was terminated by adding a saturated aqueous solution of ammonium chloride and the mixture was warmed to 0° C. The reaction mixture was extracted with hexane and the organic layer was washed with a saturated aqueous solution of ammonium chloride—a 28% ammonia water (5:1) and a saturated aqueous solution of sodium chloride and dried over anhydrous magnesium sulfate. The solvent was evaporated under reduced pressure and the residue was purified by column chromatography on silica gel (hexane:ethyl acetate=20:1→10:1) to give the title compound (1.05 g) having the following physical data.

Description: pale yellow oil; TLC: Rf 0.57 (hexane:ethyl acetate=4:1); NMR (CDCl3): δ 7.30–7.02 (m, 4H), 5.64 (dd, J=15,4.2 Hz, 1H), 5.54 (dd, J=15, 6.9 Hz, 1H), 4.42 (s, 2H), 4.27 (m, 1H), 4.03 (m, 1H), 3.65 (s, 3H), 3.38 (s, 3H), 2.74 (m, 2H), 2.59 (ddd, J=18, 7.0,1.1 Hz, 1H), 2.44 (m, 1H), 2.28 (t, J=7.5 Hz, 2H), 2.16 (dd, J=18, 8.0 Hz, 1H), 1.90 (m, 1H), 1.68–1.12 (m, 10H), 0.88 (s, 9H), 0.83 (s, 9H), 0.07 (s, 3H), 0.05 (s, 3H), −0.13 (s, 3H), −0.29 (s, 3H).

EXAMPLE 1

(11α,15α)-9-oxo-11,15-Dihydroxy-16-(3-methoxymethylphenyl)-17,18,19,20-tetranorprost-13E-enoic Acid Methyl Ester

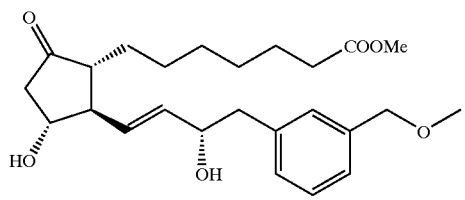

To a solution of the compound synthesized in reference example 13 (1.01 g) in acetonitrile (20 ml) were added pyridine (2 ml) and hydrofluoric acid—pyridine complex (4 ml) at 0° C. and the mixture was stirred for 3 hours at room temperature. The reaction mixture was added into cooled ethyl acetate—a saturated aqueous solution of sodium bicarbonate and the mixture was extracted with ethyl acetate. The organic layer was washed with a saturated aqueous solution of sodium bicarbonate and a saturated aqueous solution of sodium chloride, and dried over anhydrous sodium sulfate. The solvent was evaporated under reduced pressure and the residue was purified by column chromatography on silica gel (hexane:ethyl acetate=1:2→1:4→ethyl acetate) to give the title compound (535 mg) having the following physical data.

Description: pale yellow oil; TLC: Rf 0.55 (chloroform=methanol=9:1); NMR (CDCl₃): δ 7.28 (m, 1H), 7.23–7.10 (m, 3H), 5.72 (dd, J=15, 6.2 Hz, 1H), 5.51 (dd, J=15, 8.9 Hz, 1H), 4.48–4.35 (m, 3H), 3.93 (m, 1H), 3.65 (s, 3H), 3.41 (s, 3H), 2.90 (dd, J=14, 5.3 Hz, 1H), 2.82 (dd, J=14, 7.1 Hz, 1H), 2.68 (dd, J=18, 7.5 Hz, 1H), 2.32 (m, 1H), 2.29 (t, J=7.4 Hz, 2H), 2.20 (dd, J=18, 9.8 Hz, 1H), 1.96 (m, 1H), 1.66–1.16 (m, 10H).

EXAMPLE 1 (1)

(11α,15α)-9-oxo-11,15-Dihydroxy-16-(3-ethoxymethylphenyl)-17,18,19,20-tetranorprost-5Z,13E-dienoic Acid Methyl Ester

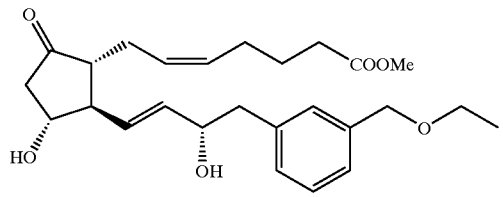

By the same procedures as described in reference examples 1~13 and example 1, the title compound having the following physical data was obtained.

TLC: Rf 0.30 (ethyl acetate); NMR (CDCl₃): δ 7.33–7.06 (4H, m), 5.67 (1H, dd, J=15.4 Hz, 6.6 Hz), 5.57–5.18 (3H, m), 4.45 (2H, s), 4.40–4.24 (1H, m), 4.02–3.83 (1H, m), 3.83–3.70 (1H, br), 3.65 (3H, s), 3.57 (2H, q, J=7.0 Hz), 2.94–2.58 (4H, m), 2.45–1.96 (9H, m), 1.75–1.54 (2H, m), 1.25 (3H, t, J=7.0 Hz).

EXAMPLE 2

(11α,15α)-9-oxo-11,15-Dihydroxy-16-(3-methoxymethylphenyl)-17,18,19,20-tetranorprost-13E-enoic Acid

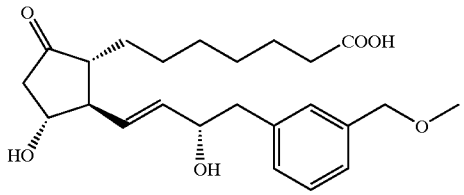

To a solution of the compound synthesized in example 1 (320 mg) in ethanol (2.5 ml) was added phosphate buffer (pH 8.0, 2.5 ml) and porcine liver esterase (200 μl+200 μl) and the mixture was stirred for 4 hours at room temperature. The reaction solution was acidified by adding a saturated aqueous solution of ammonium sulfate and a 1N hydrochloric acid and the mixture was extracted with ethyl acetate. The organic layer was washed with water and a saturated aqueous solution of sodium chloride and dried over anhydrous sodium sulfate. The solvent was evaporated under reduced pressure and the residue was purified by column chromatography on silica gel (chloroform→chloroform:methanol=30:1→15:1) to give the title compound (275 mg) having the following physical data.

Description: colorless oil; TLC: Rf 0.43 (chloroform: methanol=9:1); NMR (CDCl₃): δ 7.31–7.09 (m, 4H), 5.73 (dd, J=15, 6.2 Hz, 1H), 5.52 (dd, J=15, 8.9 Hz, 1H), 4.49–4.34 (m, 3H), 3.93 (m, 1H), 3.50 (br, 3H), 3.41 (s, 3H), 2.88 (dd, J=14, 5.4 Hz, 1H), 2.82 (dd, J=14, 7.4 Hz, 1H), 2.68 (ddd, J=18, 7.4, 0.9 Hz, 1H), 2.32 (m, 1H), 2.31 (t, J=7.4 Hz, 2H), 2.20 (dd, J=18, 9.8 Hz, 1H), 1.96 (m, 1H), 1.68–1.18 (m, 10H).

EXAMPLE 2 (1)~2 (15)

By the same procedure as described in reference examples 1~13 and examples 1 and 2, the title compounds having the following physical data were obtained.

EXAMPLE 2 (1)

(11α,15α)-9-oxo-11,15-Dihydroxy-16-[3-(2-fluoroethyl)phenyl]-17,18,19,20-tetranorprost-13E-enoic Acid

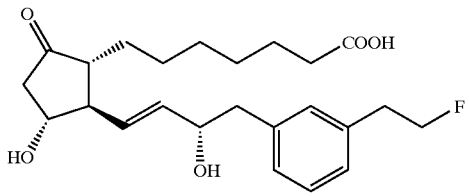

TLC: Rf 0.36 (ethyl acetate:acetic acid=50:1); NMR (CDCl$_3$): δ 7.25 (1H, m), 7.08 (3H, m), 5.72 (1H, dd, J=15, 6.7 Hz), 5.54 (1H, dd, J=15, 8.4 Hz), 4.63 (2H, dt, J=47, 6.3 Hz), 4.37 (1H, m), 4.17 (3H, br), 3.98 (1H, m), 2.98 (2H, dt, J=25, 6.3 Hz), 2.82 (2H, m), 2.70 (1H, dd, J=19, 7.4 Hz), 2.32 (3H, m), 2.19 (1H, dd, J=19, 9.9 Hz), 1.96 (1H, m), 1.72–1.13 (10H, m).

EXAMPLE 2 (2)

(11α,15α)-9-oxo-11,15-dihydroxy-16-[3-(2-ethoxyethyl)phenyl]-17,18,19,20-tetranorprost-13E-enoic Acid

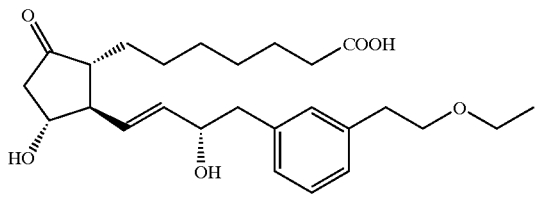

TLC: Rf 0.36 (ethyl acetate:acetic acid =50:1); NMR (CDCl$_3$): δ 7.25–7.01 (m, 4H), 5.74 (dd, J=15.4, 6.2 Hz, 1H), 5.54 (dd, J=15.4, 8.8 Hz, 1H), 4.46–4.32 (m, 1H), 4.06–3.88 (m, 1H), 3.66 (t, J=7.2 Hz, 2H), 3.52 (q, J=7.0 Hz, 2H), 3.40–3.00 (br, 3H), 2.95–2.60 (m, 5H), 2.43–2.11 (m, 4H), 2.07–1.89 (m, 1H), 1.72–1.24 (m, 10H), 1.19 (t, J=7.0 Hz, 3H).

EXAMPLE 2 (3)

(11α,15α)-9-oxo-11,15-dihydroxy-16-(3-ethoxymethylphenyl)-17,18,19,20-tetranorprost-13E-enoic Acid

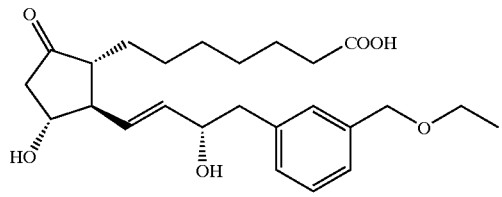

TLC: Rf 0.31 (ethyl acetate:acetic acid=50:1); NMR (CDCl$_3$): δ 7.33–7.06 (4H, m), 5.70 (1H, dd, J=15.3 Hz, 6.6 Hz), 5.48 (1H, dd, J=15.3 Hz, 8.4 Hz), 5.30–4.60 (3H, br), 4.46 (2H, s), 4.42–4.28 (1H, m), 4.00–3.82 (1H, m), 3.57 (2H, q, J=7.0 Hz), 2.94–2.58 (3H, m), 2.42–2.08 (4H, m), 2.04–1.86 (1H, m), 1.72–1.14 (13H, m).

EXAMPLE 2 (4)

(11α,15α)-9-oxo-11,15-dihydroxy-16-(3-methyl-4-hydroxyphenyl)-17,18,19,20-tetranorprost-13E-enoic Acid

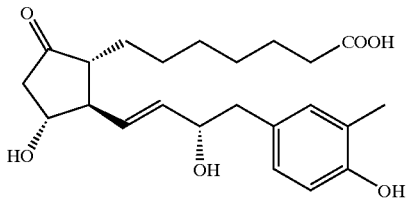

TLC: Rf 0.15 (chloroform:ethhanol:acetic acid=40:2:1); NMR (CD$_3$OD): δ 6.9–6.75 (m, 2H), 6.62 (d, J=8 Hz, 1H), 5.60 (dd, J=16, 6 Hz, 1H), 5.46 (dd, J=16, 8 Hz, 1H), 4.3–4.15 (m, 1H), 4.05–3.9 (m, 1H), 2.79 (dd, J=14, 6 Hz, 1H), 2.7–2.5 (m, 2H), 2.4–2.2 (m, 1H), 2.28 (t, J=7 Hz, 2H), 2.14 (s, 3H), 2.2–1.9 (m, 2H), 1.7–1.2 (m, 10H).

EXAMPLE 2 (5)

(11α,15α)-9-oxo-11,15-Dihydroxy-16-[3-(2-fluoroethyl)phenyl]-1,6-(1,4-phenylene)-2,3,4,5,17,18,19,20-octanorprost-13E-enoic Acid

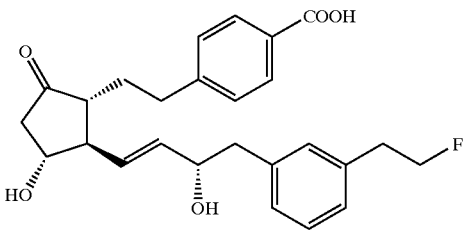

TLC: Rf 0.40 (chloroform:ethhanol=9:1); NMR (CDCl$_3$): δ 8.00 (d, J=8.4 Hz, 2H), 7.23 (m, 3H), 7.08 (m, 3H), 5.72 (dd, J=15, 6.4 Hz, 1H), 5.50 (dd, J=15, 8.4 Hz, 1H), 4.61 (dt, J=47, 6.3 Hz, 2H), 4.38 (m, 1H), 3.98 (m, 1H), 3.63 (br, 3H), 2.95 (dt, J=24, 6.3 Hz, 2H), 2.88–2.62 (m, 5H), 2.34 (m, 1H), 2.24 (dd, J=19, 9.9 Hz, 1H), 2.07–1.62 (m, 3H).

EXAMPLE 2 (6)

(11α,15α)-9-oxo-11,15-Dihydroxy-16-[3-(2-ethoxyethyl)phenyl]-1,6-(1,4-phenylene)-2,3,4,5,17,18,19,20-octanorprost-13E-enoic Acid

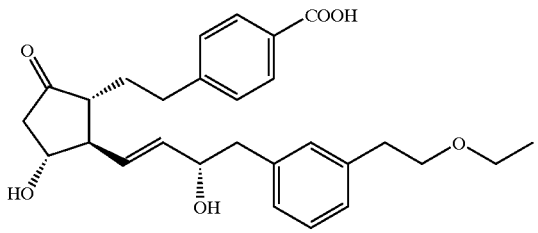

TLC: Rf 0.39 (chloroform:ethhanol=9:1); NMR (CDCl$_3$): δ 8.00 (d, J=8.4 Hz, 2H), 7.21 (m, 3H), 7.06 (m, 3H), 5.71 (dd, J=15, 6.2 Hz, 1H), 5.48 (dd, J=15, 8.6 Hz, 1H), 4.37 (m, 1H), 3.97 (m, 1H), 3.64 (t, J=7.1 Hz, 2H), 3.51 (q, J=7.2 Hz, 2H), 2.93–2.60 (m, 7H), 2.67 (br, 3H), 2.35 (m, 1H), 2.25 (dd, J=19, 9.8 Hz, 1H), 2.05–1.62 (m, 3H), 1.20 (t, J=7.2 Hz, 3H).

EXAMPLE 2 (7)

(11α,15α)-9-oxo-11,15-Dihydroxy-16-(3-methyl-4-hydroxyphenyl)-1,6-(1,4-phenylene)-2,3,4,5,17,18,19,20-octanorprost-13E-enoic Acid

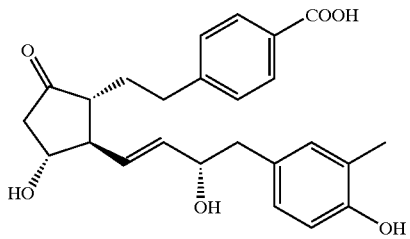

TLC: Rf 0.26 (chloroform=methanol=9:1); NMR (CDCl$_3$): δ 7.90 (d, J=8 Hz, 2H), 7.15 (d, J=8 Hz, 2H), 6.89 (s, 1H), 6.82 (d, J=8 Hz, 1H), 6.59 (d, J=8 Hz, 1H), 5.62 (dd, J=15, 7 Hz, 1H), 5.42 (dd, J=15, 9 Hz, 1H), 4.22 (q, J=8 Hz, 1H), 3.96 (q, J=8 Hz, 1H), 2.81 (dd, J=14, 6 Hz, 1H), 2.7–2.55 (m, 4H), 2.4–2.3 (m, 1H), 2.10 (dd, J=18,8 Hz, 1H), 2.08 (s, 3H), 2.0–1.9 (m, 1H), 1.9–1.7 (m, 1H), 1.8–1.6 (m, 1H).

EXAMPLE 2 (8)

(11α,15α)-9-oxo-11,15-Dihydroxy-16-(3-methoxymethylphenyl)-1,6-(1,4-phenylene)-2,3,4,5,17,18,19,20-octanorprost-13E-enoic Acid

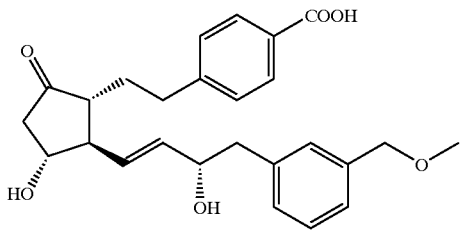

TLC: Rf 0.18 (chloroform:ethhanol:acetic acid=40:2:1); NMR (CDCl$_3$): δ 7.98 (d, J=8 Hz, 2H), 7.3–7.1 (m, 6H), 5.72 (dd, J=16, 6 Hz, 1H), 5.42 (dd, J=16, 9 Hz, 1H), 4.5–4.3 (m, 3H), 4.0–3.8 (m, 1H), 3.41 (s, 3H), 2.9–2.6 (m, 5H), 2.4–2.1 (m, 2H), 2.0–1.6 (m, 3H).

EXAMPLE 2 (9)

(11α,15α)-9-oxo-11,15-Dihydroxy-16-[3-(2-fluoroethyl)phenyl]-17,18,19,20-tetranorprost-5Z,13E-dienoic Acid

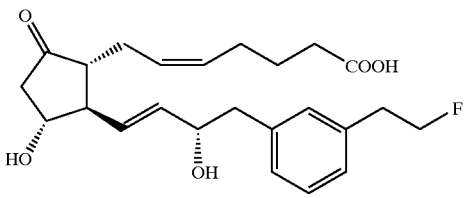

TLC: Rf 0.39 (chloroform=methanol=9:1); NMR (CDCl$_3$): δ 7.25 (1H, m), 7.10 (3H, m), 5.71 (1H, dd, J=15, 6.2 Hz), 5.56 (1H, dd, J=15, 8.2 Hz), 5.38 (2H, m), 4.63 (2H, dt, J=47, 6.3 Hz), 4.41 (1H, m), 4.08 (3H, br), 3.98 (1H, m), 2.98 (2H, dt, J=25, 6.3 Hz), 2.83 (2H, m), 2.70 (1H, dd, J=18, 7.3 Hz), 2.45–1.95 (9H, m), 1.68 (2H, m).

EXAMPLE 2 (10)

(11α,15α)-9-oxo-11,15-Dihydroxy-16-[3-(2-ethoxyethyl)phenyl]-17,18,19,20-tetranorprost-5Z,13E-dienoic Acid

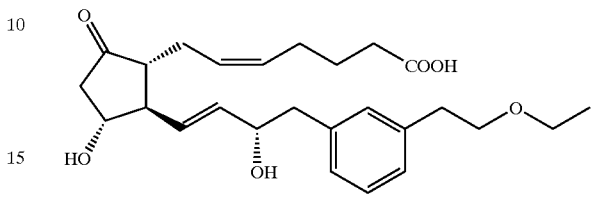

TLC: Rf 0.43 (chloroform:ethhanol=9:1); NMR (CDCl$_3$): δ 7.23 (m, 1H), 7.07 (m, 3H), 5.71 (dd, J=15, 5.9 Hz, 1H), 5.56 (dd, J=15, 7.9 Hz, 1H), 5.38 (m, 2H), 4.43 (br, 3H), 4.41 (m, 1H), 3.95 (m, 1H), 3.66 (t, J=7.2 Hz, 2H), 3.52 (q, J=7.1 Hz, 2H), 2.86 (t, J=7.2 Hz, 2H), 2.83 (m, 2H), 2.69 (dd, J=18, 7.6 Hz, 1H), 2.45–1.94 (m, 9H), 1.67 (m, 2H), 1.19 (t, J=7.1 Hz, 3H).

EXAMPLE 2 (11)

(11α,15α)-9-oxo-11,15-Dihydroxy-16-(3-ethoxymethylphenyl)-17,18,19,20-tetranorprost-5Z,13E-dienoic Acid

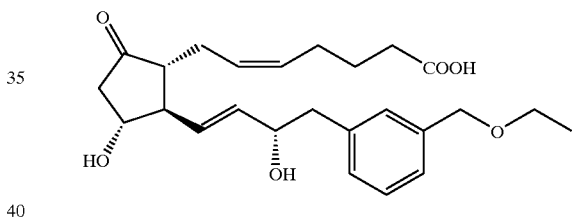

TLC: Rf 0.35 (ethyl acetate:acetic acid=50:1); NMR (CDCl$_3$): δ 7.34–7.08 (4H, m), 5.69 (1H, dd, J=15.4 Hz, 6.2 Hz), 5.50 (1H, dd, J=15.4 Hz, 8.0 Hz), 5.43–5.26 (2H, m), 5.26–4.70 (3H, br), 4.46 (2H, s), 4.45–4.34 (1H, m), 4.00–3.82 (1H, m), 3.58 (2H, q, J=7.0 Hz), 2.84 (2H, d, J=6.2 Hz), 2.78–2.58 (1H, m), 2.46–1.94 (9H, m), 1.78–1.53 (2H, m), 1.24 (3H, t, J=7.0 Hz).

EXAMPLE 2 (12)

(15α)-9-oxo-15-Hydroxy-16-(3-ethoxymethylphenyl)-17,18,19,20-tetranorprost-5Z,13E-dienoic Acid

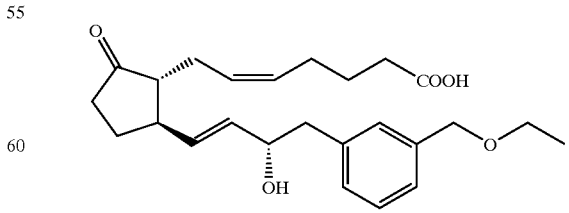

TLC: Rf 0.45 (chloroform:ethhanol=19:1); NMR (CDCl$_3$): δ 7.34–7.11 (m, 4H), 5.72 (dd, J=15.6, 6.3 Hz, 1H), 5.68–5.60 (m, 1H), 5.52–5.32 (m, 2H), 4.50 (s, 2H), 4.48–4.40 (m, 1H), 3.58 (q, J=6.9 Hz, 2H), 3.10–2.90 (m, 4H), 2.54–1.86 (m, 10H), 1.78–1.50 (m, 4H), 1.25 (t, J=6.9 Hz, 3H).

EXAMPLE 2 (13)

(11α,15α)-9-oxo-11,15-Dihydroxy-16-(3-methyl-4-hydroxyphenyl)-17,18,19,20-tetranorprost-5Z,13E-dienoic Acid

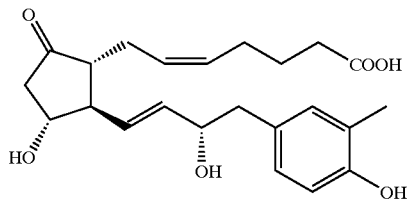

TLC: Rf 0.46 (ethyl acetate:acetic acid=19:1); NMR (CD$_3$OD): δ 6.89 (s, 1H), 6.83 (d, J=8 Hz, 1H), 6.63 (d, J=8 Hz, 1H), 5.61 (dd, J=15, 6 Hz, 1H), 5.48 (dd, J=15, 8 Hz, 1H), 5.4–5.2 (m, 2H), 4.23 (q, J=6 Hz, 1H), 4.00 (q, J=8 Hz, 1H), 2.78 (dd, J=18, 6 Hz, 1H), 2.7–2.5 (m, 2H), 2.4–2.2 (m, 4H), 2.14 (s, 3H), 2.2–2.0 (m, 5H), 1.8–1.6 (m, 2H).

EXAMPLE 2 (14)

(11α,15α)-9-oxo-11,15-dihydroxy-16-(3-methoxymethylphenyl)-17,18,19,20-tetranorprost-5Z,13E-dienoic Acid

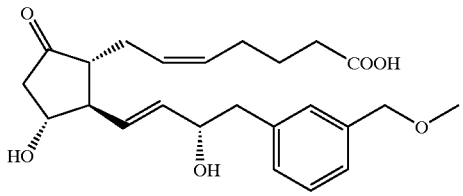

TLC: Rf 0.37 (chloroform:ethhanol=9:1); NMR (CDCl$_3$): δ 7.35–7.11 (4H, m), 5.72 (1H, dd, J=15, 5.2 Hz), 5.54 (1H, dd, J=15, 7.9 Hz), 5.41 (2H, m), 4.47 (1H, m), 4.44 (2H, s), 3.92 (1H, m), 3.43 (3H, s), 3.12 (3H, br), 2.89 (2H, d, J=6.6 Hz), 2.69 (1H, dd, J=18, 8.2 Hz), 2.44–1.97 (9H, m), 1.67 (2H, m).

EXAMPLE 2 (15)

(15α)-9-oxo-15-Hydroxy-16-(3-methoxymethylphenyl)-17,18,19,20-tetranorprost-5Z,13E-dienoic Acid

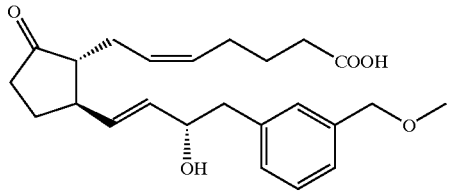

TLC: Rf 0.27 (ethyl acetate); NMR (CDCl$_3$): δ 7.35–7.10 (m, 4H), 5.90–5.54 (m, 3H), 5.48–5.30 (m, 2H), 4.44 (s, 2H), 4.43–4.33 (m, 1H), 3.40 (s, 3H), 2.95–2.74 (m, 2H), 2.58–1.84 (m, 11H), 1.78–1.42 (m, 4H).

REFERENCE EXAMPLE 14

(Z)-7-[(1R,2S,3R,5R)-5-Chloro-2-hydroxymethyl-3-(2-tetrahydropyranyloxy)cyclopentan-1-yl]-5-heptenoic Acid Methyl Ester

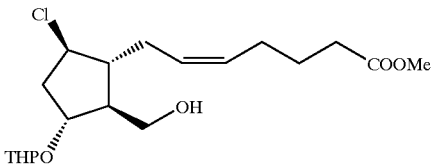

To a solution of methyl (Z)-7-[(1R,2S,3R,5R)-5-hydroxy-2-(1-methyl-1-methoxy)ethoxymethyl-3-(2-tetrahydropyranyloxy)cyclopentan-1-yl]-5-heptenoate (50.0 g) and triethylamine (48.8 ml) in methylene chloride (250 ml) was added mesyl chloride (13.6 ml) in methylene chloride (50 ml) at 0° C. dropwise and the mixture was stirred for 1 hour at the same condition. To this solution was added water (200 ml) and the mixture was extracted with ethyl acetate twice. The organic layer was washed with water and a saturated aqueous solution of sodium chloride, dried over anhydrous magnesium sulfate and concentrated to give a crude compound (mesyl compound).

To a solution of thus obtained mesyl compound in toluene (600 ml) was added tetrabutylammonium chloride (48.6 g) and potassium carbonate (48.3 g) and the mixture was stirred for 4 hours at 60° C. The mixture was allowed to cool to 20° C. and to this solution was added water (300 ml) and the mixture was extracted with ethyl acetate (600 ml+400 ml). The organic layer was washed with water and a saturated aqueous solution of sodium chloride, dried over anhydrous sulfate, concentrated to give the crude compound (chloro compound, 52 g).

To a solution of thus obtained chloro compound in tetrahydrofuran (250 ml) was added a 0.2 N hydrochloric acid (100 ml) at −5° C. dropwise over a period of 1 hour and the mixture was stirred for 3 hours at the same condition. To the mixture was added a 1 N hydrochloric acid (10 ml) dropwise and the mixture was stirred for 1 hour. To this solution was added a saturated aqueous solution of sodium bicarbonate (300 ml) and the mixture was extracted with ethyl acetate (400 ml+300 ml). The organic layer was washed with water and a saturated aqueous solution of sodium chloride, dried over anhydrous magnesium sulfate and concentrated. The residue was purified by column chromatography on silica gel (hexane:ethyl acetate=3:1) to give the title compound (16.5 g) having the following physical data.

TLC: Rf 0.41 (hexane:ethyl acetate=1:1, HPTLC); NMR (CDCl$_3$): δ 5.45–5.30 (m, 2H), 4.64–4.48 (m, 1H), 4.30–3.68 (m, 4H), 3.60 (s, 3H), 3.56–3.40 (m, 2H), 2.4–1.4 (m).

REFERENCE EXAMPLE 15

(Z)-7-[(1R,2R,3R,5R)-5-Chloro-2-formyl-3-(2-tetrahydropyranyloxy)cyclopentan-1-yl]-5-heptenoic Acid Methyl Ester

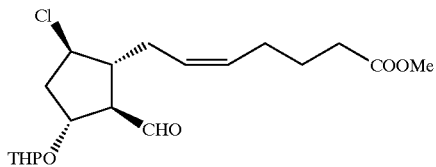

To a solution of the compound synthesized in reference example 14 (17.0 g) in dimethylsulfoxide (300 ml) was added triethylamine (30 ml). To the mixture was added sulfur trioxide-pyridine complex (21.7 g) in water bath. The mixture was stirred for 30 minutes at room temperature. To this solution was added water and the mixture was extracted with ethyl acetate. The organic layer was washed with water and a saturated aqueous solution of sodium chloride, dried over anhydrous magnesium sulfate and concentrated. The residue was purified by column chromatography on silica gel (hexane:ethyl acetate=4:1) to give the title compound (15.9 g) having the following physical data.

TLC: Rf 0.55 (hexane:ethyl acetate=2:1); NMR (CDCl$_3$): δ 9.77 and 9.74 (1H, 2d, J=2.0 Hz), 5.58–5.30 (2H, m), 4.66–4.50 (2H, m), 4.12–3.98 (1H, m), 3.90–3.72 (1H, m), 3.68 (3H, s), 3.60–3.40 (1H, m). 2.80–2.00 (8H, m), 2.33 (2H, t, J=7.5 Hz), 1.90–1.40 (8H, m).

REFERENCE EXAMPLE 16

3-[3-Methoxymethyl-4-(2-tetrahydropyranylyoxy) phenyl]-2-oxopropylphosphonic Acid Dimethyl

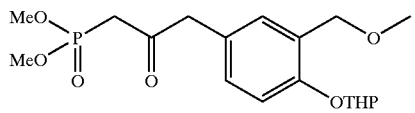

The mixture of methyl phosphonic acid dimethyl (1.2 ml) and anhydrous tetrahydrofuran (10 ml) was cooled to −70° C. and thereto was added n-butyl lithium (6.7 ml, 1.54 M solution in hexane) over a period of 1 hour with the internal temperature kept under −65° C. Thus obtained pale yellow solution was stirred for another 1 hour and thereto was added a solution of 3-methoxymethyl-4-(2-tetrahydropyranyloxy) phenylacetic acid methyl ester (1.5 g) in anhydrous tetrahydrofuran (5 ml) dropwise over a period of 35 minutes. The mixture was stirred for 3 hours and the reaction was terminated by adding acetic acid (0.66 ml) and the mixture was allowed to warm to room temperature. To the mixture was added water and separated into two layers. The aqueous layer was extracted with ethyl acetate twice and the organic layer was washed with a saturated aqueous solution of sodium chloride, dried over anhydrous sodium sulfate, concentrated to give the crude compound. The crude compound was purified by column chromatography on silica gel (hexane:ethyl acetate=1:1→ethyl acetate→ethyl acetate:methanol=20:1) to give the title compound (1.3 g) having the following physical data.

Description: pale yellow oil; TLC: Rf 0.21 (ethyl acetate); NMR (CDCl$_3$): δ 7.25–7.05 (m, 3H), 5.5–5.4 (m, 1H), 4.51 (s, 2H), 4.0–3.8 (m, 1H), 3.82 (s, 2H), 3.81 (s, 3H), 3.76 (s, 3H), 3.7–3.5 (m, 1H), 3.43 (s, 3H), 3.05 (d, J=23 Hz, 2H), 2.1–1.5 (m, 6H).

REFERENCE EXAMPLE 17

(9β,11α)-9-Chloro-11-(2-tetrahydropyranyloxy)-15-oxo-16-[3-methoxymethyl-4-(2-tetrahydropyranyloxy)phenyl]-17,18,19,20-tetranorprost-5Z,13E-dienoic Acid Methyl Ester

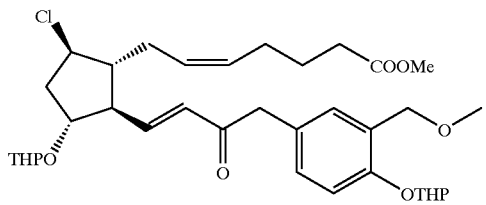

The compound synthesized in reference example 16 (233 mg) was dissolved in tetrahydrofuran (5 ml) and thereto was added sodium hydride (18 mg) at 0° C. and the mixture was stirred for 20 minutes. To this solution was added a solution of the compound synthesized in reference example 15 (150 mg) in tetrahydrofuran (1.5 ml) dropwise and the mixture was stirred for 2 hours. The reaction solution was cooled to 0° C. and thereto was added acetic acid (0.051 ml). The mixture was stirred and extracted with water and hexane, and the organic layer was washed with water and a saturated aqueous solution of sodium chloride successively, and dried over anhydrous sodium sulfate. The aqueous layer was extracted with hexane and the organic layer was washed with water and a saturated aqueous solution of sodium chloride, dried over anhydrous sodium sulfate and combined with the former organic layer and the mixture was concentrated under reduced pressure. The crude compound was purified by column chromatography on silica gel (hexane:ethyl acetate=9:1→4:1→3:1) to give the title compound (215 mg) having the following physical data.

TLC: Rf 0.43 (hexane:ethyl acetate=2:1); NMR (CDCl$_3$): δ 7.22 (s, 1H), 7.05 (s, 2H), 6.91–6.76 (m, 1H), 6.19 (t, J=15.0 Hz, 1H), 5.50–5.25 (m, 3H), 4.64–4.42 (m, 3H), 4.23–4.08 (m, 1H), 4.06–3.94 (m, 1H), 3.92–3.70 (m, 3H), 3.66 (s, 3H), 3.66–3.54 (m, 2H), 3.43 (s, 3H), 3.40–3.30 (m, 1H), 2.50–1.38 (m, 24H).

REFERENCE EXAMPLE 18

(9β,11α,15ξ)-9-Chloro-11-(2-tetrahydropyranyloxy)-15-hydroxy-16-[3-methoxymethyl-4-(2-tetrahydropyranyloxy)phenyl]-17,18,19,20-tetranorprost-5Z,13E-dienoic Acid Methyl Ester

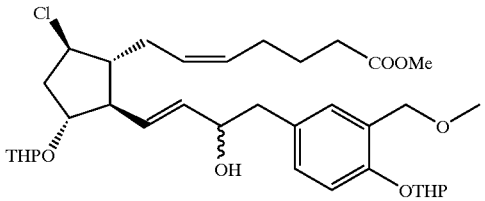

The compound synthesized in reference example 41 (210 mg) was dissolved in tetrahydrofuran (2 ml) and thereto was added (R)-2-methyl-CBS-oxazaborolidine (0.066 ml, 1.0 M solution in toluene) was added at 0° C. and thereto was added borane (1M solution in tetrahydrofuran, 0.23 ml) dropwise. The mixture was stirred for 20 minutes, to the reaction solution was added methanol (0.5 ml) and the mixture was extracted with a 1N hydrochloric acid and ethyl acetate. The organic layer was washed with a saturated aqueous solution of sodium chloride, dried over anhydrous sodium sulfate, and the mixture was combined with the former organic layer and the mixture was concentrated under reduced pressure. The crude compound was purified by column chromatography on silica gel (hexane:ethyl acetate=4:1→3:1→2:1) to give the title compound (145 mg, more polar isomer at 15-position) having the following physical data.

Description: colorless oil; TLC: Rf 0.28 (hexane:ethyl acetate=2:1); NMR (CDCl$_3$): δ 7.23 (s, 1H), 7.05 (s, 2H), 5.66–5.58 (m, 2H), 5.42–5.34 (m, 3H), 4.66–4.54 (m, 1H), 4.52 (s, 2H), 4.36–4.26 (m, 1H), 4.16–3.78 (m, 4H), 3.67 (s, 3H), 3.67–3.55 (m, 1H), 3.54–3.40 (m, 3H), 3.44 (s, 3H), 2.84–2.66 (m, 2H), 2.40–1.20 (m, 25H).

EXAMPLE 3

(9β,11α,15ξ)-9-Chloro-11,15-dihydroxy-16-(3-methoxymethyl-4-hydroxyphenyl)-17,18,19,20-tetranorprost-5Z,13E-dienoic Acid Methyl Ester

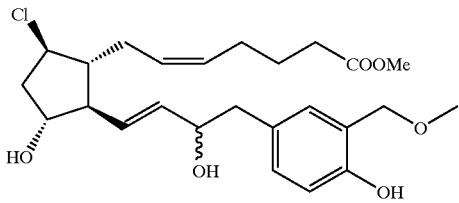

The compound synthesized in reference example 18 (142 mg) was dissolved in methanol (2 ml) and thereto was added p-toluenesulfonic acid (10 mg) and the mixture was stirred for 1 hour at room temperature. To this reaction solution was added water and a saturated aqueous solution of sodium chloride and the mixture was extracted with ethyl acetate. The organic layer was washed with a saturated aqueous solution of sodium chloride and dried over anhydrous sodium sulfate. On the other hand, the aqueous layer was extracted with ethyl acetate and the organic layer was washed with a saturated aqueous solution of sodium chloride, dried over anhydrous sodium sulfate and combined with the former organic layer and the mixture was concentrated under reduced pressure. The crude compound was purified by column chromatography on silica gel (hexane:ethyl acetate=1:1→1:2) to give the title compound (97 mg) having the following physical data.

Description: colorless oil; TLC: Rf 0.51 (hexane:ethyl acetate=1:3); NMR (CDCl$_3$): δ 7.34 (s, 1H), 7.04 (dd, J=2.4, 8.4 Hz, 1H), 6.87 (d, J=2.4 Hz, 1H), 6.82 (d, J=8.4 Hz, 1H), 5.62 (dd, J=5.7, 15.3 Hz, 1H), 5.56–5.32 (m, 3H), 4.62 (s, 2H), 4.36–4.25 (m, 1H), 4.33–3.96 (m, 2H), 3.67 (s, 3H), 3.45 (s, 3H), 2.78 (dd, J=5.4, 13.5 Hz, 1H), 2.70 (dd, J=7.5, 13.5 Hz, 1H), 2.37–1.90 (m, 12H), 1.75–1.63 (m, 2H).

EXAMPLE 4

(9β,11α,15ξ)-9-Chloro-11,15-dihydroxy-16-(3-methoxymethyl-4-hydroxyphenyl)-17,18,19,20-tetranorprost-5Z,13E-dienoic Acid

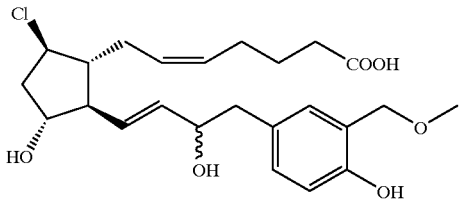

The compound synthesized in example 3 (81 mg) was dissolved in methanol (2 ml) and thereto was added a 2N aqueous solution of sodium hydroxide (1 ml) and the mixture was stirred for 2 hours at room temperature. To this reaction solution was added a 1 N hydrochloric acid (2.2 ml) and thereto was added water and ethyl acetate, the organic layer was washed with water and a saturated aqueous solution of sodium chloride, dried over anhydrous sodium sulfate. On the other hand, the aqueous layer was extracted with ethyl acetate and the organic layer was washed with water and a aqueous solution of sodium chloride, dried over anhydrous sodium sulfate and combined with the former organic layer and the mixture was concentrated under reduced pressure. The crude compound was purified by column chromatography on silica gel (chloroform:methanol=20:1→10:1) to give the title compound (73 mg) having the following physical data.

Description: colorless oil; more polar: TLC: Rf 0.57 (chloroform=methanol=9:1); NMR (CDCl$_3$): δ 7.02 (dd, J=1.8, 8.4 Hz, 1H), 6.87 (d, J=1.8 Hz, 1H), 6.80 (d, J=8.4 Hz, 1H), 5.58 (dd, J=6.0, 15.6 Hz, 1H), 5.53–5.35 (m, 3H), 4.60 (s, 2H) 4.34–4.24 (m, 1H), 4.10–3.96 (m, 2H), 3.44 (s, 3H), 2.80–2.66 (m, 2H), 2.40–1.85 (m, 10H), 1.77–1.60 (m, 2H).

EXAMPLE 4 (1)~4 (12)

By the same procedures as described in reference example 14~18 and example 3 and 4, the title compounds having the following physical data were obtained.

EXAMPLE 4 (1)

(9β,11α,15ξ)-9-Chloro-11,15-dihydroxy-16-[3-(2-ethoxyethyl)-4-hydroxyphenyl]-17,18,19,20-tetranorprost-5Z,13E-dienoic Acid

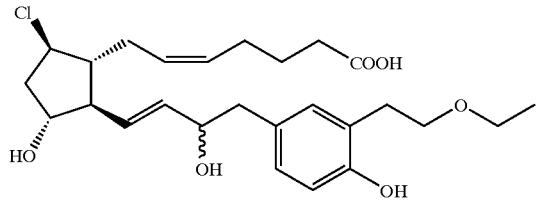

more polar: TLC: Rf 0.43 (chloroform:ethhanol=9:1); NMR (CDCl$_3$): δ 8.60–8.00 (br, 1H), 6.97 (dd, J=2.1, 8.1 Hz, 1H), 6.90–6.82 (m, 2H), 5.61 (dd, J=6.0, 16.2 Hz, 1H), 5.55–5.35 (m, 3H), 4.35–4.25 (m, 1H), 4.20–3.98 (m, 2H), 3.72 (t, J=4.8 Hz, 2H), 3.56 (q, J=7.2 Hz, 2H), 2.85 (t, J=5.4 Hz, 2H), 2.77 (dd, J=5.4, 13.2 Hz, 1H), 2.69 (dd, J=7.8, 13.2 Hz, 1H), 2.40–1.85 (m, 10H), 1.80–1.60 (m, 2H), 1.24 (t, J=7.2 Hz, 3H).

EXAMPLE 4 (2)

(9β,11α,15ξ)-9-Chloro-11,15-dihydroxy-16-(3-ethyl-4-hydroxyphenyl)-17,18,19,20-tetranorprost-5Z,13E-dienoic Acid

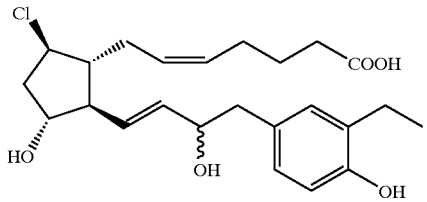

more polar: TLC: Rf 0.36 (chloroform=methanol=9:1); NMR (CDCl$_3$): δ 6.96 (d, J=2.2 Hz, 1H), 6.88 (dd, J=8.0, 2.2 Hz, 1H), 6.68 (d, J=8.0 Hz, 1H), 5.62 (dd, J=15, 5.4 Hz, 1H), 5.59–5.35 (m, 3H), 4.37 (m, 1H), 4.17–3.95 (m, 2H), 2.78 (m, 2H), 2.61 (q, J=7.5 Hz, 2H), 2.45 (br, 4H), 2.42–1.86 (m, 10H), 1.71 (m, 2H), 1.22 (t, J=7.5 Hz, 3H).

EXAMPLE 4 (3)

(9β,11α,15ξ)-9-Chloro-11,15-dihydroxy-16-(3-hydroxymethylphenyl)-17,18,19,20-tetranorprost-5Z,13E-dienoic Acid

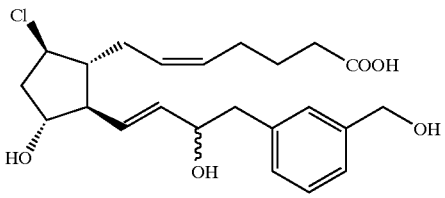

less polar: TLC: Rf 0.26 (chloroform:ethhanol 9:1); NMR (CDCl$_3$+CD$_3$OD): δ 7.3–7.1 (m, 4H), 5.56 (dd, J=15, 7 Hz, 1H), 5.5–5.4 (m, 2H), 5.29 (dd, J=15, 8 Hz, 1H), 4.62 (s, 2H), 4.29 (q, J=7 Hz, 1H), 4.05–3.95 (m, 1H), 3.84 (q, J=8 Hz, 1H), 2.94 (dd, J=13, 6 Hz, 1H), 2.79 (dd, J=13, 7 Hz, 1H), 2.7–2.2 (br), 2.4–1.8 (m, 10H), 1.8–1.6 (m, 2H).

more polar: TLC: Rf 0.24 (chloroform=methanol=9:1); NMR (CDCl$_3$+CD$_3$OD): δ 7.3–7.1 (m, 4H), 5.59 (dd, J=15, 6 Hz, 1H), 5.5–5.35 (m, 3H), 4.62 (s, 2H), 4.34 (q, J=6 Hz, 1H), 4.05–3.95 (m, 2H), 2.85 (d, J=6 Hz, 2H), 2.8–2.3 (br), 2.4–1.8 (m, 10H), 1.8–1.6 (m, 2H).

EXAMPLE 4 (4)

(9β,11α,15ξ)-9-Chloro-11,15-dihydroxy-16-[3-(2-isopropyloxyethyl)phenyl]-17,18,19,20-tetranorprost-5Z,13E-dienoic Acid

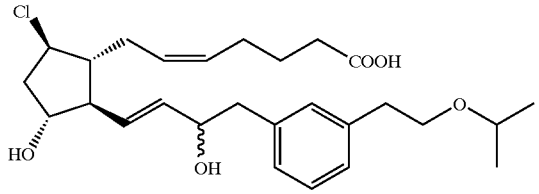

more polar: TLC: Rf 0.44 (chloroform:ethhanol=10:1); NMR (CDCl$_3$): δ 7.28–7.01 (m, 4H), 5.62 (dd, J=15.3, 5.7 Hz, 1H), 5.58–5.36 (m, 3H), 4.43–4.30 (m, 1H), 4.10–3.98 (m, 2H), 3.70–3.52 (m, 3H), 3.50–3.00 (br, 3), 2.92–2.74 (m, 4H), 2.43–1.84 (m, 10H), 1.80–1.60 (m, 2H), 1.15 (d, J=6.0 Hz, 6H).

EXAMPLE 4 (5)

(9β,11α,15ξ)-9-Chloro-11,15-dihydroxy-16-(3-isopropyloxymethylphenyl)-17,18,19,20-tetranorprost-5Z,13E-dienoic Acid

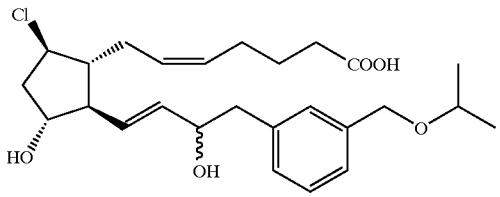

more polar: TLC: Rf 0.34 (chloroform=methanol=10:1); NMR (CDCl$_3$): δ 7.35–7.08 (m, 4H), 5.65 (dd, J=15.6, 5.2 Hz, 1H), 5.59–5.35 (m, 3H), 4.48 (s, 2H), 4.47–4.37 (m, 1H), 4.12–3.92 (m, 2H), 3.73 (sep, J=5.8 Hz, 1H), 2.91 (dd, J=13.4, 5.6 Hz, 1H), 2.81 (dd, J=13.4, 7.0 Hz, 1H), 2.74–1.82 (m, 13H), 1.82–1.54 (m, 2H), 1.23 (d, J=5.8 Hz, 6H).

EXAMPLE 4 (6)

(9β,11α,15ξ)-9-Chloro-11,15-dihydroxy-16-(3-methoxymethyl-5-methoxyphenyl)-17,18,19,20-tetranorprost-5Z,13E-dienoic Acid

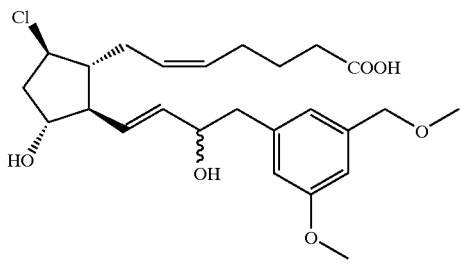

more polar: TLC: Rf 0.37 (chloroform:ethhanol=9:1); NMR (CDCl$_3$): δ 6.79 (s, 1H), 6.74 (s, 1H), 6.70 (s, 1H), 5.64 (dd, J=5.7, 15.6 Hz, 1H), 5.56–5.38 (m, 3H), 4.41 (s, 2H), 4.48–4.36 (m, 1H), 4.10–3.98 (m, 2H), 3.80 (s, 3H), 3.41 (s, 3H), 2.92–2.76 (m, 2H), 2.40–1.86 (m, 10H), 1.80–1.60 (m, 2H).

EXAMPLE 4 (7)

(9β,11α,15ξ)-9-Chloro-11,15-dihydroxy-16-[3-(2-methoxyethyl)phenyl]-17,18,19,20-tetranorprost-5Z,13E-dienoic Acid

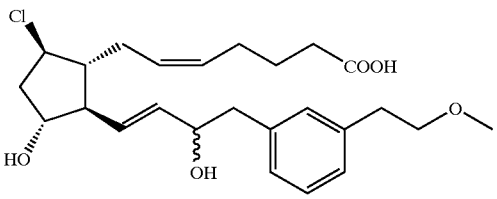

more polar: TLC: Rf 0.31 (chloroform:ethhanol=10:1); NMR (CDCl$_3$): δ 7.28–7.00 (m, 4H), 5.61 (dd, J=15.4, 5.8 Hz, 1H), 5.56–5.32 (m, 3H), 4.44–4.28 (m, 1H), 4.28–4.12 (br, 3H), 4.12–3.92 (m, 2H), 3.62 (t, J=7.0 Hz, 2H), 3.35 (s, 3H), 2.94–2.68 (m, 4H), 2.45–1.82 (m, 10H), 1.82–1.56 (m, 2H),

EXAMPLE 4 (8)

(9β,11α,15ξ)-9-Chloro-11,15-dihydroxy-16-(3-propyl-4-hydroxyphenyl)-17,18,19,20-tetranorprost-5Z,13E-dienoic Acid

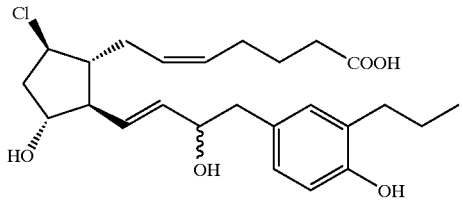

more polar: TLC: Rf 0.29 (chloroform:ethhanol 9:1); NMR (CDCl$_3$): δ 6.95 (d, J=2.1 Hz, 1H), 6.89 (dd, J=2.1, 8.4 Hz, 1H), 6.69 (d, J=8.4 Hz, 1H), 5.70–5.38 (m, 4H), 4.42–4.30 (m, 1H), 4.17–4.00 (m, 2H), 2.86–2.68 (m, 2H), 2.55 (t, J=7.5 Hz, 2H), 2.40–1.85 (m, 10H), 1.85–1.50 (m, 4H), 0.97 (t, J=7.2 Hz, 3H).

EXAMPLE 4 (9)

(9β,11α,15ξ)-9-Chloro-11,15-dihydroxy-16-[3-(2-propyloxyethyl)phenyl]-17,18,19,20-tetranorprost-5Z,13E-dienoic Acid

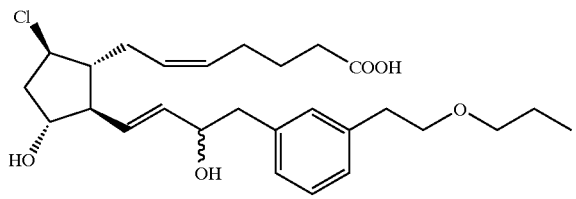

more polar: TLC: Rf 0.45 (chloroform:ethhanol=10:1); NMR (CDCl$_3$): δ 7.30–7.00 (m, 4H), 5.63 (dd, J=15.4, 5.4 Hz, 1H), 5.57–5.35 (m, 3H), 4.45–4.30 (m, 1H), 4.13–3.96 (m, 2H), 3.96–3.00 (br, 3H), 3.64 (t, J=7.0 Hz, 2H), 3.41 (t, J=6.8 Hz, 2H), 2.94–2.70 (m, 4H), 2.40–1.82 (m, 10H), 1.82–1.56 (m, 2H). 4H), 0.89 (t, J=7.3 Hz, 3H).

EXAMPLE 4 (10)

(9β,11α,15ξ)-9-Chloro-11,15-dihydroxy-16-(3-propyloxymethylphenyl)-17,18,19,20-tetranorprost-5Z,13E-dienoic Acid

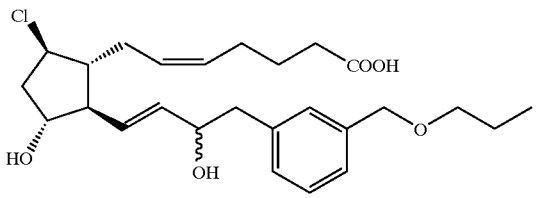

more polar: TLC: Rf 0.55 (chloroform:methanol=9:1); NMR (CDCl$_3$): δ 7.34–7.06 (m, 4H), 5.61 (dd, J=16, 5.7 Hz, 1H), 5.55–5.34 (m, 3H), 4.47 (s, 2H), 4.38 (m, 1H), 4.00 (m, 2H), 3.90 (br, 3H), 3.47 (t, J=6.8 Hz, 2H), 2.85 (m, 2H), 2.34 (t, J=6.7 Hz, 2H), 2.29–1.81 (m, 8H), 1.78–1.54 (m, 4H), 0.94 (t, J=7.4 Hz, 3H).

EXAMPLE 4 (11)

(9β,11α,15ξ)-9-Fluoro-11,15-dihydroxy-16-(3-ethoxymethylphenyl)-17,18,19,20-tetranorprost-5Z, 13E-dienoic Acid

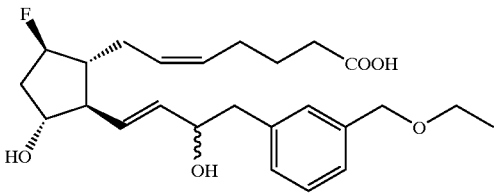

more polar: TLC: Rf 0.55 (chloroform=methanol=9:1); NMR (CDCl$_3$): δ 7.3–7.1 (m, 4H), 5.66 (dd, J=15, 6 Hz, 1H), 5.55–5.35 (m, 3H), 4.9–4.65 (m, 1H), 4.48 (s, 2H), 4.44 (q, J=6 Hz, 1H), 3.98 (q, J=9 Hz, 1H), 3.8–2.4 (br, 3H), 3.58 (q, J=7 Hz, 2H), 2.91 (dd, J=14, 6 Hz, 1H), 2.83 (dd, J=14, 6 Hz, 1H), 2.4–1.8 (m, 12H).

EXAMPLE 4 (12)

(9β,11α,15ξ)-9-Fluoro-11,15-dihydroxy-16-(3-propyloxymethylphenyl)-17,18,19,20-tetranorprost-5Z,13E-dienoic Acid

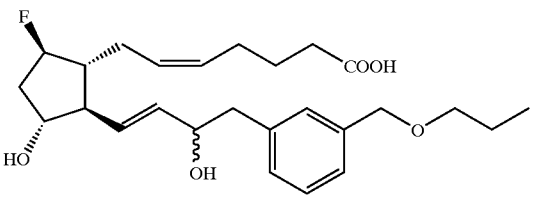

more polar: TLC: Rf 0.67 (chloroform:ethhanol=9:1); NMR (CDCl$_3$): δ 7.36–7.08 (m, 4H), 5.65 (dd, J=15, 5.4 Hz, 1H), 5.57–5.33 (m, 3H), 4.78 (m, 1H), 4.48 (s, 2H), 4.43 (m, 1H), 3.98 (m, 1H), 3.51 (br, 3H), 3.47 (t, J=6.8 Hz, 2H), 2.87 (m, 2H), 2.40–1.54 (m, 14H), 0.94 (t, J=7.5 Hz, 3H).

REFERENCE EXAMPLE 19

(9α,11α)-9-Acetyloxy-11-(2-tetrahydropyranyloxy)-15-oxo-16-(3-methoxymethylphenyl)-17,18,19,20-tetranorprost-1,3E-enoic Acid Methyl Ester

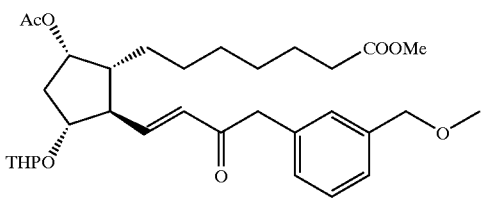

Under atmosphere of argon, to a solution of 3-(3-methoxymethylphenyl)-2-oxopropylphosphonic acid dimethyl (172 mg) in anhydrous tetrahydrofuran (10 ml) was added sodium hydride (62.5%, 22 mg) and the obtained white suspension was stirred for 45 minutes. Thereto was added a solution of methyl 7-[(1R,2R,3R,5S)-5-acetyloxy-2-formyl-3-(2-tetrahydropyranyloxy)cyclopentan-1-yl] heptanoate (200 mg) in anhydrous tetrahydrofuran (6 ml) and the mixture was stirred for 20 hours. The reaction was quenched by adding acetic acid at 0° C. and the mixture was poured into water. The reaction mixture was extracted with ethyl acetate and the organic layer was washed with a saturated aqueous solution of sodium chloride, dried over anhydrous sodium sulfate and concentrated. The residue was purified by column chromatography on silica gel (hexane:ethyl acetate=3:1→2:1) to give the title compound having the following physical data (209 mg).

Description: yellow oil; TLC: Rf 0.29 (hexane:ethyl acetate=2:1); NMR (CDCl$_3$): δ 7.40–7.10 (m, 4H), 6.78 (m, 1H), 6.25 (m, 1H), 5.11 (m, 1H), 4.47 (m, 1H), 4.44 (s, 2H), 4.20–3.20 (m, 3H), 3.84 (s, 2H), 3.66 (s, 3H), 3.39 (s, 3H), 2.77–2.32 (m, 2H), 2.29 (t, J=7.6 Hz, 2H), 2.05 (s, 3H), 1.89–1.02 (m, 18H).

REFERENCE EXAMPLE 20

(9α,11α,15α)-9-Acetyloxy-11-(2-tetrahydropyranyloxy)-15-hydroxy-16-(3-methoxymethylphenyl)-17,18,19,20-tetranorprost-13E-enoic Acid Methyl Ester

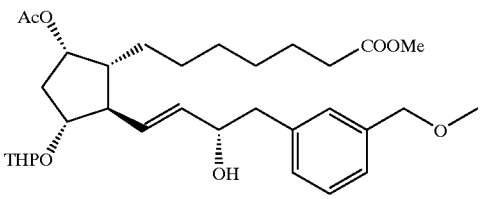

Under atmosphere of argon, to a solution of the compound synthesized in reference example 19 (205 mg) in anhydrous tetrahydrofuran (1.9 ml) was added (R)-2-methyl-CBS-oxazaborolidine (1M solution in toluene, 73 μl+25 μl). To the reaction solution was added borohydride (1.0M solution in tetrahydrofuran, 220 μl+70 μl) over a period of 2 minutes and the mixture was stirred for 45 minutes. The reaction was quenched by adding methanol at 0° C. and the reaction mixture was extracted with ethyl acetate, and the organic layer was washed with a saturated aqueous solution of sodium chloride, dried over anhydrous sodium sulfate and the solvent was evaporated. The residue was purified by column chromatography on silica gel (hexane:ethyl acetate= 3:2→1:2) to give the title compound (164 mg, more polar isomer at 15-position) having the following physical data.

Description: colorless oil; TLC: Rf 0.43 (hexane:ethyl acetate 1:1); NMR (CDCl$_3$): δ 7.38–7.09 (m, 4H), 5.80–5.44 (m, 2H), 5.09 (m, 1H), 4.61 (m, 1H), 4.44 (s, 2H), 4.37 (m, 1H), 4.04–3.72 (m, 2H), 3.66 (s, 3H), 3.43 (m, 1H), 3.40 (s, 3H), 2.83 (m, 2H), 2.57–2.33 (m, 2H), 2.29 (t, J=7.5 Hz, 2H), 2.05 (s, 3H), 1.98–1.02 (m, 18H).

REFERENCE EXAMPLE 21

(9α,11α15α)-9-Hydroxy-11,15-bis(2-tetrahydropyranyloxy)-16-(3-methoxymethylphenyl)-17,18,19,20-tetranorprost-13E-enoic Acid

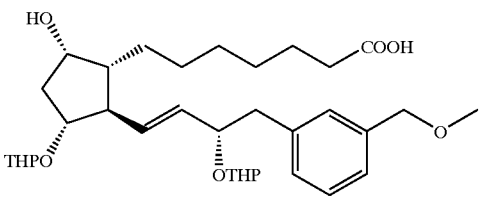

Under atmosphere of argon, to a solution of the compound synthesized in reference example 20 (173 mg) in anhydrous methylene chloride (2 ml) was added dihydropyran (42 ml) and pyridinium p-tosylate (7.8 mg) and the mixture was stirred overnight. The reaction mixture was extracted with ethyl acetate and the organic layer was washed with a saturated aqueous solution of sodium chloride, dried over anhydrous sodium sulfate and the solvent was evaporated to give the crude compound. The crude residue was dissolved in methanol (4 ml) and to the solution was added a 2N aqueous solution of sodium hydroxide (2 ml) and the mixture was stirred for 2 hours. The reaction solution was acidified by adding a 1 N aqueous solution of ammonium chloride at 0° C. and the mixture was extracted with ethyl acetate. The organic layer was washed with water twice and a saturated aqueous solution of sodium chloride, dried over anhydrous sodium sulfate and the solvent was evaporated to give the crude compound (199 mg). The crude compound was used in the next reaction without further purification.

Description: pale yellow oil; TLC: Rf 0.30 (hexane:ethyl acetate=1:3).

EXAMPLE 5

(11α,15α)-9-oxo-11,15-Dihydroxy-16-(3-methoxymethylphenyl)-17,18,19,20-tetranorprost-13E-enoic Acid

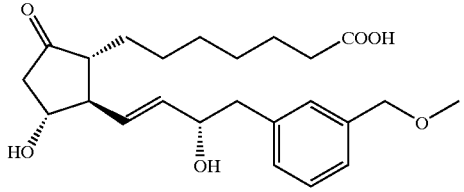

Under atmosphere of argon, to a solution of the compound synthesized in reference example 21 (199 mg) in acetone (1.5 ml) was added Jones reagent at −30° C. until the starting material disappeared. To the mixture was added isopropanol and the mixture was warmed to −15° C. and thereto was added diethyl ether and water. The reaction mixture was extracted with diethyl ether and the organic layer was washed with water twice and a saturated aqueous solution of sodium chloride, dried over anhydrous sodium sulfate and the solvent was evaporated to give the crude compound. The crude compound was dissolved in a mixture of acetic acid-tetrahydrofuran-water (2 ml+1 ml+0.5 ml). The reaction solution was stirred for 2 hours at 50° C. The reaction solution was extracted with ethyl acetate. The organic layer was washed with a saturated aqueous solution of sodium chloride, dried over anhydrous sodium sulfate and the solvent was evaporated under reduced pressure. The residue was purified by column chromatography on silica gel (hexane:ethyl acetate=1:2+1% acetic acid→1:4+1% acetic acid) to give the title compound (80 mg) having the following physical data.

Description: pale yellow oil; more polar: TLC: Rf 0.48 (chloroform=methanol=9:1); NMR (CDCl$_3$): δ 7.33–7.10 (m, 4H), 5.73 (dd, J=15, 6.3 Hz, 1H), 5.53 (dd, J=15, 8.6 Hz, 1H), 4.49–4.37 (m, 3H), 3.94 (m, 1H), 3.42 (s, 3H), 3.38 (br, 3H), 2.89 (dd, J=14, 5.6 Hz, 1H), 2.82 (dd, J=14, 7.2 Hz, 1H), 2.69 (ddd, J=19, 7.7, 1.1 Hz, 1H), 2.32 (t, J=7.8 Hz, 2H), 2.31 (m, 1H), 2.20 (dd, J=19, 9.8 Hz, 1H), 1.97 (m, 1H), 1.67–1.20 (m, 10H).

EXAMPLE 5 (1)~5 (15)

By the same procedures as described in reference example 19~21 and example 5, the title compounds having the following physical data were obtained.

EXAMPLE 5 (1)

(11α,15ξ)-9-oxo-11,15-Dihydroxy-16-[3-(2-isopropyloxyethyl)phenyl]-17,18,19,20-tetranorprost-13E-enoic Acid

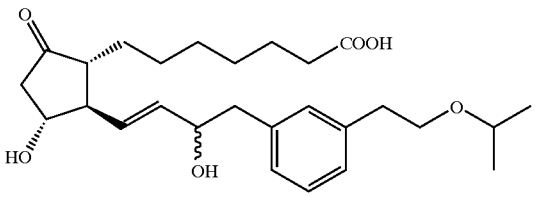

more polar: TLC: Rf 0.60 (ethyl acetate:acetic acid=20:1); NMR (CDCl$_3$): δ 7.22 (t, J=8 Hz, 1H), 7.1–7.0 (m, 3H), 5.73 (dd, J=15, 6 Hz, 1H), 5.54 (dd, J=15, 8 Hz, 1H), 4.37 (q, J=6 Hz, 1H), 3.96 (q, J=9 Hz, 1H), 3.7–3.55 (m, 3H), 2.9–2.6 (m, 5H), 2.4–2.3 (m, 3H), 2.21 (dd, J=18, 7 Hz, 1H), 2.0–19 (m, 1H), 1.7–1.2 (m, 10H), 1.15 (d, J=6 Hz, 6H).

EXAMPLE 5 (2)

(11α,15ξ)-9-oxo-11,15-Dihydroxy-16-(3-isopropyloxymethylphenyl)-17,18,19,20-tetranorprost-13E-enoic Acid

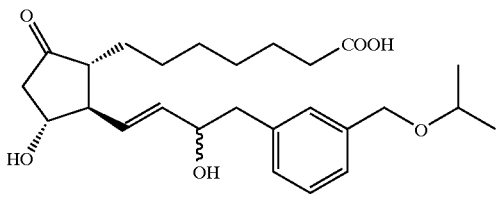

more polar: TLC: Rf 0.59 (ethyl acetate:acetic acid=20:1); NMR (CDCl$_3$): δ 7.3–7.1 (m, 4H), 5.74 (dd, J=15, 6 Hz, 1H), 5.52 (dd, J=15, 8 Hz, 1H), 4.48 (s, 2H), 4.43 (q, J=6 Hz, 1H), 3.92 (q, J=9 Hz, 1H), 3.74 (pent, J=6 Hz, 1H), 2.90 (dd, J=14, 5 Hz, 1H), 2.82 (dd, J=14, 7 Hz, 1H), 2.69 (dd, J=18, 7 Hz, 1H), 2.4–2.3 (m, 1H), 2.31 (t, J=8 Hz, 2H), 2.20 (dd, J=18, 10 Hz, 1H), 2.0–1.9 (m, 1H), 1.7–1.2 (m, 10H), 1.24 (d, J=6 Hz, 3H), 1.23 (d, J=6 Hz, 3H).

EXAMPLE 5 (3)

(11α,15ξ)-9-oxo-11,15-Dihydroxy-16-(3-methoxymethyl-5-methoxyphenyl)-17,18,19,20-tetranorprost-13E-enoic Acid

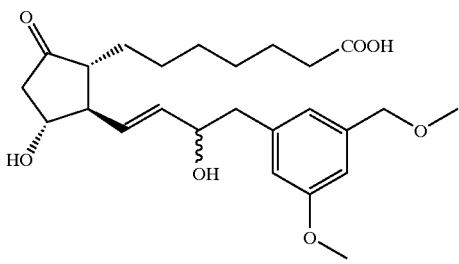

more polar: TLC: Rf 0.48 (chloroform:ethhanol 9:1); NMR (CDCl$_3$): δ 6.81 (m, 1H), 6.72 (m, 2H), 5.73 (dd, J=15, 6.0 Hz, 1H), 5.54 (dd, J=15, 8.5 Hz, 1H), 4.41 (s, 2H), 4.40 (m, 1H), 3.96 (m, 1H), 3.80 (s, 3H), 3.43 (br, 3H), 3.41 (s, 3H), 2.82 (m, 2H), 2.71 (dd, J=18, 7.2 Hz, 1H), 2.44–2.12 (m, 4H), 1.96 (m, 1H), 1.74–1.18 (m, 10H).

EXAMPLE 5 (4)

(11α,15ξ)-9-oxo-11,15-Dihydroxy-16-[3-(2-propyloxyethyl)phenyl]-17,18,19,20-tetranorprost-13E-enoic Acid

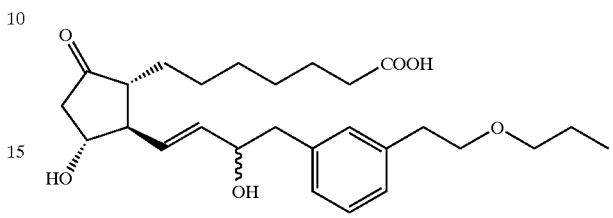

more polar: TLC: Rf 0.51 (chloroform:ethhanol=9:1); NMR (CDCl$_3$): δ 7.31–7.00 (m, 4H), 5.75 (dd, J=15,5.9 Hz, 1H), 5.57 (dd, J=15, 8.6 Hz, 1H), 4.42 (m, 1H), 3.98 (m, 1H), 3.67 (t, J=7.4 Hz, 2H), 3.42 (t, J=6.8 Hz, 2H), 2.96–2.79 (m, 4H), 2.71 (dd, J=18, 7.4 Hz, 1H), 2.38 (br, 3H), 2.37–2.12 (m, 4H), 1.98 (m, 1H), 1.71–1.13 (m, 12H), 0.89 (t, J=7.3 Hz, 3H).

EXAMPLE 5 (5)

(11α,15ξ)-9-oxo-11,15-Dihydroxy-16-[3-(2-isopropyloxyethyl)phenyl]-17,18,19,20-tetranorprost-5Z,13E-dienoic Acid

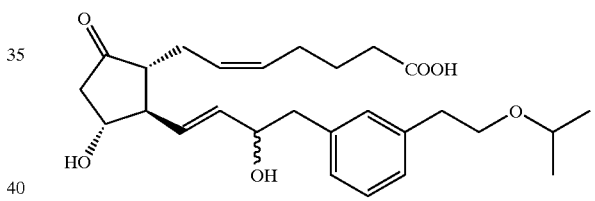

more polar: TLC: Rf 0.60 (ethyl acetate:acetic acid=20:1); NMR (CDCl$_3$): δ 7.23 (t, J=8 Hz, 1H), 7.1–7.0 (m, 3H), 5.72 (dd, J=15, 6 Hz, 1H), 5.56 (dd, J=15, 8 Hz, 1H), 5.5–5.3 (m, 2H), 4.42 (q, J=6 Hz, 1H), 3.96 (q, J=9 Hz, 1H), 3.7–3.55 (m, 3H), 2.9–2.6 (m, 5H), 2.4–2.1 (m, 9H), 1.8–1.6 (m, 2H), 1.16 (d, J=6 Hz, 6H).

EXAMPLE 5 (6)

(11α,15ξ)-9-oxo-11,15-Dihydroxy-16-(3-isopropyloxymethylphenyl)-17,18,19,20-tetranorprost-5Z,13E-dienoic Acid

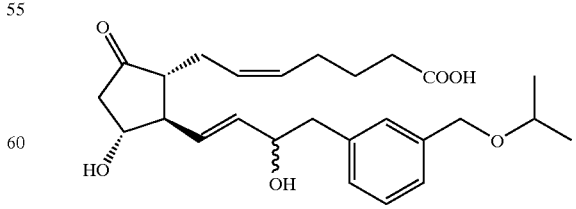

more polar: TLC: Rf 0.59 (ethyl acetate:acetic acid=20:1); NMR (CDCl$_3$): δ 7.3–7.1 (m, 4H), 5.72 (dd, J=15, 6 Hz, 1H), 5.52 (dd, J=15, 8 Hz, 1H), 5.5–5.3 (m, 2H), 4.48 (s, 2H), 4.5–4.4 (m, 1H), 3.90 (q, J=9 Hz, 1H), 3.74 (pent, J=6 Hz, 1H), 2.95–2.8 (m, 2H), 2.68 (dd, J=18, 8 Hz, 1H), 2.4–2.25 (m, 4H), 2.25–1.9 (m, 5H), 1.75–1.55 (m, 2H), 1.24 (d, J=6 Hz, 3H), 1.23 (d, J=6 Hz, 3H).

EXAMPLE 5 (7)

(11α,15ξ)-9-oxo-11,15-Dihydroxy-16-(3-methoxymethyl-5-methoxyphenyl)-17,18,19,20-tetranorprost-5Z,13E-dienoic Acid

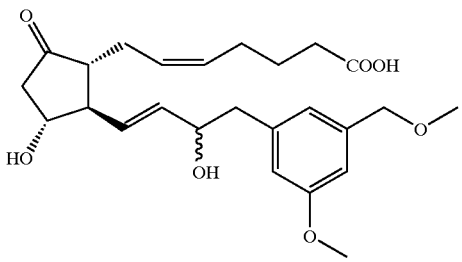

more polar: TLC: Rf 0.48 (chloroform:ethhanol=9:1); NMR (CDCl₃): δ 6.81 (m, 1H), 6.72 (m, 2H), 5.71 (dd, J=15, 5.4 Hz, 1H), 5.55 (dd, J=15, 7.9 Hz, 1H), 5.40 (m, 2H), 4.44 (m, 1H), 4.41 (s, 2H), 3.96 (m, 1H), 3.80 (s, 3H), 3.42 (s, 3H), 3.38 (br, 3H), 2.84 (m, 2H), 2.70 (dd, J=19, 7.3 Hz, 1H), 2.45–1.98 (m, 9H), 1.66 (m, 2H).

EXAMPLE 5 (8)

(11α,15ξ)-9-oxo-11,15-Dihydroxy-16-[3-(2-propyloxyethyl)phenyl]-17,18,19,20-tetranorprost-5Z,13E-dienoic Acid

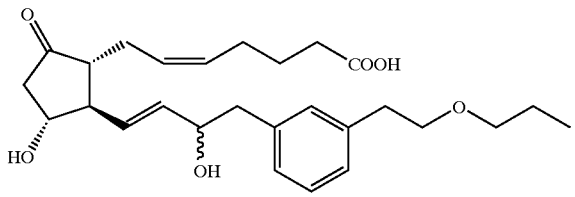

more polar: TLC: Rf 0.49 (chloroform:ethhanol=9:1); NMR (CDCl₃): δ 7.31–7.00 (m, 4H), 5.71 (dd, J=16, 5.6 Hz, 1H), 5.56 (dd, J=16, 7.9 Hz, 1H), 5.39 (m, 2H), 4.42 (m, 1H), 3.97 (m, 1H), 3.95 (br, 3H), 3.66 (t, J=7.1 Hz, 2H), 3.41 (t, J=6.8 Hz, 2H), 2.94–2.78 (m, 4H), 2.70 (dd, J=19, 7.2 Hz, 1H), 2.46–1.95 (m, 9H), 1.79–1.47 (m, 4H), 0.89 (t, J=7.4 Hz, 3H).

EXAMPLE 5 (9)

(11α,15ξ)-9-oxo-11,15-Dihydroxy-16-(3-propyl-4-hydroxyphenyl)-17,18,19,20-tetranorprost-13E-enoic Acid

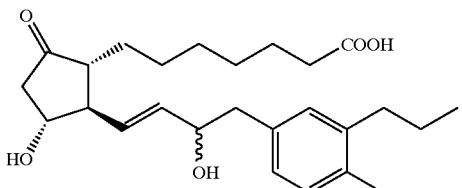

more polar: TLC: Rf 0.59 (ethyl acetate:acetic acid=20:1); NMR (CD₃OD): δ 6.88 (d, J=2.0 Hz, 1H), 6.82 (dd, J=8.2, 2.0 Hz, 1H), 6.63 (d, J=8.2 Hz, 1H), 5.60 (dd, J=15.4, 6.6 Hz, 1H), 5.47 (dd, J=15.4, 6.6 Hz, 1H), 4.24 (m, 1H), 3.98 (m, 1H), 2.82 (m, 1H), 2.72–2.42 (m, 4H), 2.40–2.20 (m, 3H), .19–1.86 (m, 2H), 1.70–1.08 (m, 12H), 0.93 (t, J=7.4 Hz, 3H).

EXAMPLE 5 (10)

(11α,15ξ)-9-oxo-11,15-Dihydroxy-16-(3-propyl-4-hydroxyphenyl)-17,18,19,20-tetranorprost-5Z,13E-dienoic Acid

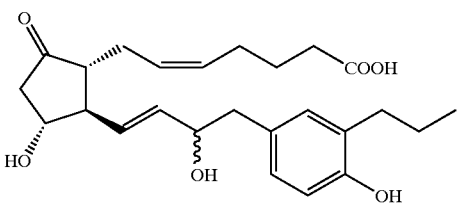

more polar: TLC: Rf 0.60 (ethyl acetate:acetic acid 20:1); NMR (CD₃OD): δ 6.89 (d, J=2.2 Hz, 1H), 6.84 (dd, J=8.2, 2.2 Hz, 1H), 6.64 (d, J=8.2 Hz, 1H), 5.70–5.16 (m, 4H), 4.24 (m, 1H), 4.00 (m, 1H), 2.80 (m, 1H), 2.72–1.92 (m, 13H), 1.73–1.45 (m, 4H), 0.93 (t, J=7.4 Hz, 3H).

EXAMPLE 5 (11)

(11α,15ξ)-9-oxo-11,15-Dihydroxy-16-(3-propyloxymethylphenyl)-17,18,19,20-tetranorprost-13E-enoic Acid

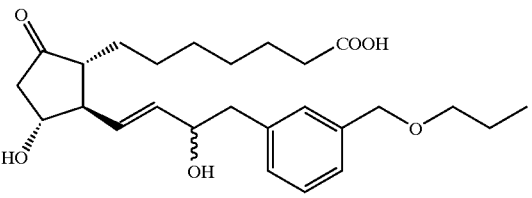

more polar: TLC: Rf 0.56 (ethyl acetate:acetic acid=20:1); NMR (CDCl₃): δ 7.38–7.07 (m, 4H), 5.75 (dd, J=15.4, 6.2 Hz, 1H), 5.51 (dd, J=15.4, 8.8 Hz, 1H), 4.48 (s, 2H), 4.40 (m, 1H), 3.94 (m, 1H), 3.48 (t, J=6.8 Hz, 2H), 2.97–2.60 (m, 3H), 2.41–1.88 (m, 5H), 1.75–1.15 (m, 12H), 0.94 (t, J=7.4 Hz, 3H).

EXAMPLE 5 (12)

(11α,15α)-9-oxo-11,15-Dihydroxy-16-(3-ethoxymethylphenyl)-1,6-(1,4-phenylene)-2,3,4,5,17,18,19,20-octanorprost-13E-enoic Acid

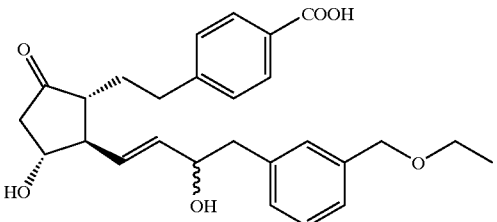

more polar: TLC: Rf 0.31 (chloroform:ethhanol 9:1); NMR (CDCl₃): δ 7.98 (d, J=8 Hz, 2H), 7.3–7.1 (m, 6H), 5.72 (dd, J=15, 6 Hz, 1H), 5.43 (dd, J=15, 9 Hz, 1H), 4.45 (s, 2H), 4.40 (q, J=6 Hz, 1H), 3.91 (q, J=8 Hz, 1H), 3.57 (q, J=7 Hz, 2H), 2.9–2.6 (m, 5H), 2.4–2.3 (m, 1H), 2.23 (dd, J=18, 9 Hz, 1H), 2.0–1.9 (m, 2H), 1.8–1.7 (m, 1H), 1.26 (t, J=7 Hz, 3H).

EXAMPLE 5 (13)

(11α,15ξ)-9-oxo-11,15-Dihydroxy-16-[3-(2-methoxyethyl)phenyl]-17,18,19,20-tetranorprost-13E-enoic Acid

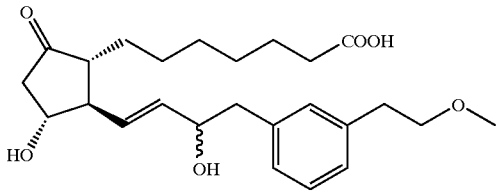

more polar: TLC: Rf 0.55 (ethyl acetate:acetic acid=20:1); NMR (CDCl$_3$): δ 7.28–7.14 (m, 1H), 7.15–6.98 (m, 3H), 5.73 (dd, J=15.4, 6.4 Hz, 1H), 5.53 (dd, J=15.4, 8.0 Hz, 1H), 4.36 (m, 1H), 3.95 (m, 1H), 3.63 (t, J=6.8 Hz, 2H), 3.36 (s, 3H), 2.94–2.60 (m, 5H), 2.42–1.84 (m, 5H), 1.74–1.18 (m, 10H).

EXAMPLE 5 (14)

(11α,15ξ)-9-oxo-11,15-Dihydroxy-16-[3-(2-methoxyethyl)phenyl]-17,18,19,20-tetranorprost-5Z,13E-dienoic Acid

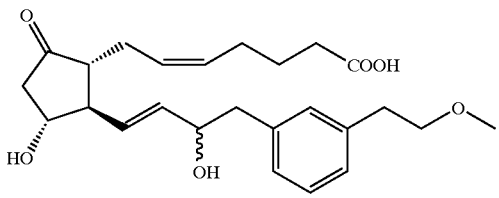

more polar: TLC: Rf 0.52 (ethyl acetate:acetic acid=20:1); NMR (CDCl$_3$): δ 7.31–7.18 (m, 1H), 7.14–7.00 (m, 3H), 5.72 (dd, J=15.0, 5.6 Hz, 1H), 5.56 (dd, J=15.0, 7.4 Hz, 1H), 5.48–5.26 (m, 2H), 4.43 (m, 1H), 3.97 (m, 1H), 3.65 (t, J=6.6 Hz, 2H), 3.35 (s, 3H), 2.98–2.60 (m, 5H), 2.46–1.90 (m, 9H), 1.80–1.45 (m, 2H).

EXAMPLE 5 (15)

(11α,15ξ)-9-oxo-11,15-Dihydroxy-16-(3-propyloxymethylphenyl)-17,18,19,20-tetranorprost-5Z,13E-dienoic Acid

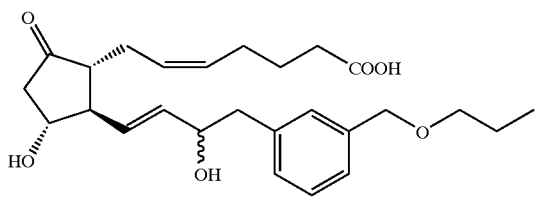

more polar: TLC: Rf 0.56 (ethyl acetate:acetic acid=20:1); NMR (CDCl$_3$): δ 7.38–7.08 (m, 4H), 5.73 (dd, J=15.4, 6.2 Hz, 1H), 5.53 (dd, J=15.4, 8.0 Hz, 1H), 5.50–5.27 (m, 2H), 4.59–4.37 (m, 3H), 3.92 (m, 1H), 3.49 (t, J=6.8 Hz, 2H), 3.38–1.87 (m, 12H), 1.84–1.52 (m, 4H), 0.94 (t, J=7.4 Hz, 3H),

REFERENCE EXAMPLE 22

(11α,15α)-9-Butanoyloxy-11,15-bis(t-butyldimethylsilyloxy)-16-(3-methoxymethylphenyl)-17,18,19,20-tetranorprost-8,13E-dienoic Acid 2-(t-Butyldimethylsilyloxy)ethyl Ester

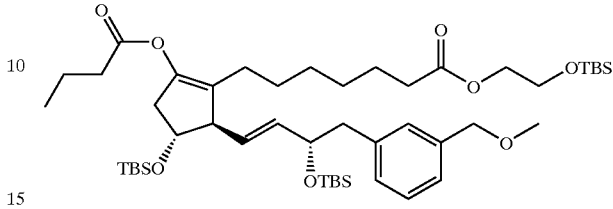

Under atmosphere of argon to a solution of (3S)-1-iodo-4-(3-methoxymethylphenyl)-3-t-butyldimethylsilyloxy-1E-butene (186 mg) in anhydrous diethyl ether (2.0 ml) was added t-butyl lithium (1.64 M solution in pentane, 0.52 ml) dropwise at −78° C. and the mixture was stirred for 45 minutes at the same condition. Thereto was added lithium 2-thienylcyano cuprate (0.25 M solution in tetrahydrofuran, 2.1 ml) dropwise and the obtained yellow sepia solution was stirred for 15 minutes. Thereto was added a solution of 2-[6-(2-t-butyldimethylsilyloxyethoxy)carbonylhexyl]-4α-t-butyldimethylsilyloxy-2-cyclopenten-1-one (155 mg) in anhydrous diethyl ether (2.0 ml) dropwise slowly and the obtained dark yellow solution was allowed to warm over a period of 40 minutes to −20° C. Thereto was added lactic anhydride (0.16 ml) and the mixture was stirred for 30 minutes at the same condition. The reaction was terminated by adding a mixture of a saturated aqueous solution of ammonium chloride and a 28% aqueous solution of ammonia (9:1), and the mixture was allowed to warm to room temperature. The reaction mixture was extracted with ethyl acetate and the organic layer was washed with a mixture of a saturated aqueous solution of ammonium chloride and a 28% ammonia water (9:1), and then with a saturated aqueous solution of sodium chloride, dried over anhydrous sodium sulfate and the solvent was evaporated. The residue was purified by column chromatography on silica gel (hexane:ethyl acetate=20:1) to give the title compound (185 mg) having the following physical data.

Description: pale yellow oil; TLC: Rf 0.51 (hexane:ethyl acetate=9:1); NMR (CDCl$_3$): δ 7.3–7.1 (m, 4H), 5.60 (dd, J=15, 5 Hz, 1H), 5.42 (dd, J=15, 9 Hz, 1H), 4.42 (s, 2H), 4.3–4.2 (m, 1H), 4.12 (dd, J=6, 5 Hz, 2H), 4.1–4.0 (m, 1H), 3.80 (dd, J=6, 5 Hz, 2H), 3.37 (s, 3H), 3.0–2.95 (m, 1H), 2.9–2.7 (m, 3H), 2.37 (t, J=8 Hz, 2H), 2.29 (t, J=8 Hz, 2H), 2.1–1.9 (m, 1H), 1.8–1.5 (m, 4H), 1.4–1.1 (m, 8H), 0.98 (t, J=7 Hz, 3H), 0.89 (s, 9H), 0.87 (s, 9H), 0.81 (s, 9H), 0.06 (s, 6H), 0.03 (s, 6H).

EXAMPLE 6

(11α,15α)-9-Butanoyloxy-11,15-dihydroxy-16-(3-methoxymethylphenyl)-17,18,19,20-tetranorprost-8,13E-dienoic Acid 2-Hydroxyethyl Ester

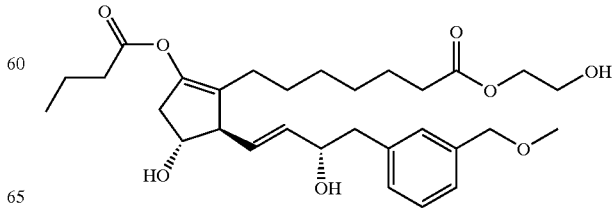

To a solution of the compound synthesized in reference example 22 (180 mg) in acetonitrile (2 ml) was added pyridine (0.2 ml) and hydrofluoric acid-pyridine complex (0.4 ml) at 0° C. and the mixture was stirred for 2 hours at room temperature. To a mixture of ethyl acetate and a saturated aqueous solution of sodium bicarbonate under vigorously stirring, was added the reaction mixture slowly. The mixture was separated into two layers and the organic layer was washed with water and a saturated aqueous solution of sodium chloride, dried over anhydrous sodium sulfate and the solvent was evaporated under reduced pressure. The residue was purified by column chromatography on silica gel (hexane:ethyl acetate=2:1→ethyl acetate) to give the title compound (79 mg) having the following physical data.

Description: colorless oil; TLC: Rf 0.48 (ethyl acetate); NMR (CDCl$_3$): δ 7.3–7.1 (m, 4H), 5.67 (dd, J=15, 6 Hz, 1H), 5.45 (dd, J=15, 9 Hz, 1H), 4.43 (s, 2H), 4.38 (q, J=6 Hz, 1H), 4.2–4.15 (m, 2H), 4.1–4.0 (m, 1H), 3.8–3.75 (m, 2H), 3.39 (s, 3H), 3.1–3.0 (m, 1H), 2.9–2.75 (m, 3H), 2.6–2.4 (br, 1H), 2.38 (t, J=8 Hz, 2H), 2.34 (t, J=7 Hz, 2H), 2.4–2.2 (m, 2H), 2.1–1.9 (m, 1H), 1.9–1.8 (br, 1H), 1.8–1.5 (m, 4H), 1.4–1.2 (m, 8H), 0.97 (t, J=7 Hz, 3H).

EXAMPLE 6 (1)~6 (4)

By the same procedures as described in reference example 22 and example 6, the title compounds having the following physical data were obtained.

EXAMPLE 6 (1)

(11α,15α)-9-Butanoyloxy-11,15-dihydroxy-16-(3-methoxymethylphenyl)-17,18,19,20-tetranorprost-8, 13E-dienoic Acid Methyl Ester

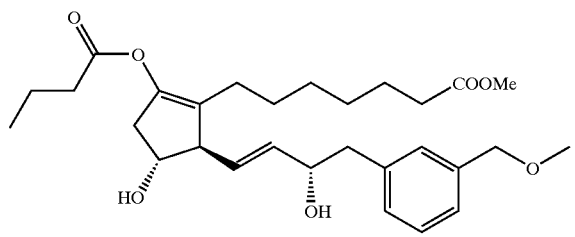

TLC: Rf 0.18 (ethyl acetate:hexane=2:1); NMR (CDCl$_3$): δ 7.3–7.1 (m, 4H), 5.67 (dd, J=15, 6 Hz, 1H), 5.45 (ddd, J=15, 9, 1 Hz, 1H), 4.43 (s, 2H), 4.45–4.35 (m, 1H), 4.1–4.0 (m, 1H), 3.68 (s, 3H), 3.42 (s, 3H), 3.1–3.0 (m, 1H), 2.9–2.8 (m, 3H), 2.45–2.35 (m, 1H), 2.39 (t, J=7 Hz, 2H), 2.29 (t, J=7 Hz, 2H), 2.3–2.2 (br, 1H), 2.1–1.95 (m, 1H), 1.8–1.5 (m, 7H), 1.4–1.2 (m, 6H), 1.00 (t, J=7 Hz, 3H).

EXAMPLE 6 (2)

(11α,15α)-9-Butanoyloxy-11,15-dihydroxy-16-(3-methyl-4-hydroxyphenyl)-17,18,19,20-tetranorprost-8,13E-dienoic Acid Methyl Ester

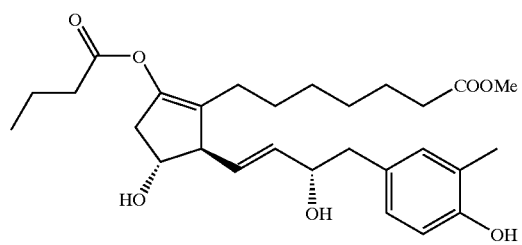

TLC: Rf 0.20 (ethyl acetate:hexane=2:1); NMR (CDCl$_3$): δ 6.94 (d, J=2 Hz, 1H), 6.87 (dd, J=8, 2 Hz, 1H), 6.70 (d, J=8 Hz, 1H), 5.62 (dd, J=15, 7 Hz, 1H), 5.43 (dd, J=15, 9 Hz, 1H), 5.29 (s, 1H), 4.39 (q, J=6 Hz, 1H), 4.1–4.0 (m, 1H), 3.68 (s, 3H), 3.1–3.0 (m, 1H), 2.9–2.8 (m, 1H), 2.74 (d, J=7 Hz, 2H), 2.45–2.35 (m, 1H), 2.39 (t, J=7 Hz, 2H), 2.31 (t, J=7 Hz, 2H), 2.23 (s, 3H), 2.1–2.0 (m, 1H), 2.0–1.9 (m, 1H), 1.8–1.5 (m, 6H), 1.4–1.1 (m, 6H), 1.00 (t, J=7 Hz, 3H).

EXAMPLE 6 (3)

(11α,15α)-9-(3-Carboxypropanoyloxy)-11,15-dihydroxy-16-(3-methoxymethylphenyl)-17,18,19, 20-tetranorprost-8,13E-dienoic Acid Methyl Ester

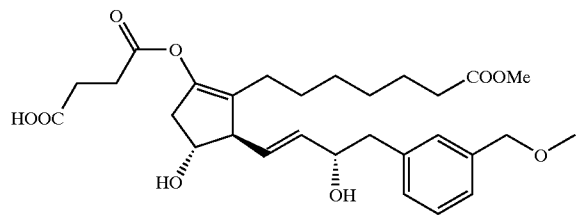

TLC: Rf 0.47 (ethyl acetate:acetic acid=50:1); NMR (CDCl$_3$): δ 7.3–7.1 (m, 4H), 5.65 (dd, J=15, 6 Hz, 1H), 5.44 (dd, J=15, 9 Hz, 1H), 4.44 (s, 2H), 4.38 (q, J=6 Hz, 1H), 4.01 (dt, J=7, 4 Hz, 1H), 3.68 (s, 3H), 3.40 (s, 3H), 3.1–3.0 (m, 1H), 2.9–2.6 (m, 7H), 2.45–2.4 (m, 1H), 2.4–2.3 (m, 3H), 2.1–2.0 (m, 1H), 1.75–1.55 (m, 4H), 1.4–1.2 (m, 6H).

EXAMPLE 6 (4)

(11α,15α)-9-Acetyloxy-11,15-dihydroxy-16-(3-methoxymethylphenyl)-17,18,19,20-tetranorprost-8, 13E-dienoic Acid Methyl Ester

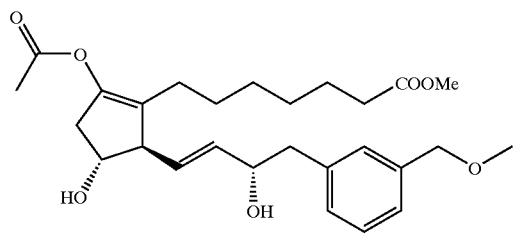

TLC: Rf 0.26 (ethyl acetate:hexane=2:1); NMR (CDCl$_3$): δ 7.3–7.1 (m, 4H), 5.66 (dd, J=15, 6 Hz, 1H), 5.43 (dd, J=15, 9 Hz, 1H), 4.42 (s, 2H), 4.45–4.3 (m, 1H), 4.1–3.95 (m, 1H), 3.65 (s, 3H), 3.40 (s, 3H), 3.1–3.0 (m, 1H), 2.9–2.7 (m, 3H), 2.5–2.3 (m, 2H), 2.30 (t, J=7 Hz, 2H), 2.15 (s, 3H), 2.1–1.9 (m, 1H), 1.9–1.5 (m, 4H), 1.4–1.1 (m, 6H).

REFERENCE EXAMPLE 23

(9β,11α,15α)-9-Hydroxy-11,15-bis(t-butyldimethylsilyloxy)-16-(3-methoxymethylphenyl)-17,18,19,20-tetranorprost-13E-enoic Acid Methyl Ester

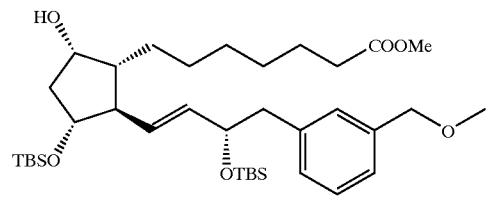

(11α,15α)-9-oxo-11,15-bis(t-Butyldimethylsilyloxy)-16-(3-methoxymethylphenyl)-17,18,19,20-tetranorprost-13E- enoic acid methyl ester (278 mg, synthesized in reference example 13) was dissolved in anhydrous THF (8 ml) and the mixture was cooled to −78° C. Thereto was added lithium tri-sec-butylborohydride (1.0M solution in THF (L-selectride®), 0.46 ml) and the mixture was stirred for 1 hour. To the mixture was added a 31% aqueous solution of hydrogen peroxide (1.6 ml) and diluted with ethyl acetate. The organic layer was washed with a 1 N hydrochloric acid, a saturated aqueous solution of sodium bicarbonate and a saturated aqueous solution of sodium chloride successively, dried over anhydrous sodium sulfate and concentrated. The residue was purified by flash column chromatography on silica gel (hexane:ethyl acetate 20:1→10:1→4:1) to give the title compound (173.7 mg) having the following physical data.

Description: colorless oil; TLC: Rf 0.46 (hexane:ethyl acetate=4:1); NMR (CDCl$_3$): δ 7.30–7.03 (m, 4H), 5.48 (dd, J=15.4 Hz, 5.6 Hz, 1H), 5.34 (dd, J=15.4 Hz, 8.6 Hz, 1H), 4.42 (s, 2H), 4.29–3.94 (m, 3H), 3.65 (s, 3H), 3.37 (s, 3H), 2.73 (d, J=6.6 Hz, 2H), 2.29 (t, J=7.5 Hz, 2H), 2.24–2.12 (m, 1H), 1.86–1.10 (m, 14H), 0.86 (s, 9H), 0.81 (s, 9H), 0.04 (s, 6H), −0.12 (s, 3H), −0.23 (s, 3H).

REFERENCE EXAMPLE 24

(9α,11α,15α)-9-Tosyloxy-11,15-bis(t-butyldimethylsilyloxy)-16-(3-methoxymethylphenyl)-17,18,19,20-tetranorprost-13E-enoic Acid Methyl Ester

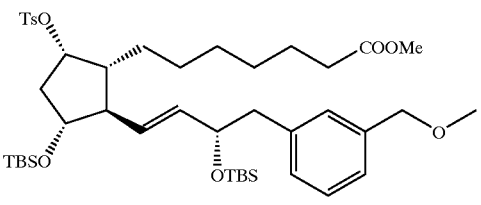

The compound synthesized in reference example 23 (173.7 mg) was dissolved in pyridine (3 ml) and the mixture was cooled to 0° C. Thereto was added tosyl chloride (500 mg) and the mixture was allowed to warm to room temperature. After stirring for 15 hours, thereto was added tosyl chloride (500 mg) and the mixture was stirred for 5.5 hours at room temperature, cooled to 0° C. and thereto was added water to terminate the reaction. The reaction solution was diluted with ether and the organic layer was washed with water and a saturated aqueous solution of sodium chloride, dried over anhydrous sodium sulfate, concentrated. The solvent was separated as azeotropic mixture with toluene to give the crude compound of title compound (217.5 mg) having the following physical data.

Description: pale yellow oil; TLC: Rf 0.62 (benzene:ethyl acetate=10:1).

EXAMPLE 7

(9β,11α,15α)-9-Chloro-11,15-dihydroxy-16-(3-methoxymethylphenyl)-17,18,19,20-tetranorprost-13E-enoic Acid Methyl Ester

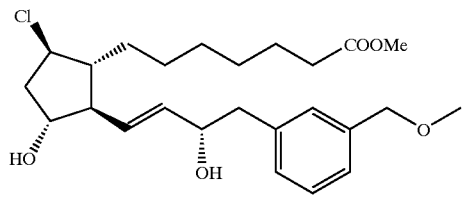

The compound synthesized in reference example 24 (217.5 mg) was dissolved in anhydrous toluene (8 ml) and to the mixture was added tetrabutylammonium chloride (730 mg) and the mixture was warmed to 55° C. After 1 hour, the mixture was diluted with ether and the organic layer was washed with water and a saturated aqueous solution of sodium chloride, dried over anhydrous sodium sulfate and concentrated. The residue was dissolved in acetonitrile (2 ml) and to the mixture was added pyridine (0.25 ml) and the mixture was cooled to 0° C. Hereto was added hydrofluoric acid-pyridine (0.5 ml) and after 5 minutes the mixture was allowed to warm to room temperature. After 1.5 hours, the mixture was diluted with ethyl acetate and the organic layer was washed with water, a saturated aqueous solution of sodium bicarbonate and a saturated aqueous solution of sodium chloride successively, dried over anhydrous sodium sulfate and concentrated. The residue was purified by column chromatography on silica gel (hexane:ethyl acetate= 1:2) and Lobar column (toluene: isopropyl alcohol =20:1) to give the title compound (55.6 mg) having the following physical data.

Description: colorless oil; TLC: Rf 0.42 (hexane:ethyl acetate=1:2); NMR (CDCl$_3$): δ 7.32–7.06 (m, 4H), 5.56 (dd, J=15.0 Hz, 6.2 Hz, 1H), 5.42 (dd, J=15.0 Hz, 7.6 Hz, 1H), 4.41 (s, 2H), 4.36–4.20 (m, 1H), 4.08–3.90 (m, 2H), 3.65 (s, 3H), 3.63–3.42 (br, 1H), 3.39 (s, 3H), 2.92–2.68 (m, 3H), 2.30 (t, J=7.5 Hz, 2H), 2.15–1.20 (m, 14H).

EXAMPLE 7 (1)

(9β,11α,15α)-9-Chloro-11,15-dihydroxy-16-(3-ethoxymethylphenyl)-17,18,19,20-tetranorprost-5Z,13E-dienoic Acid Methyl Ester

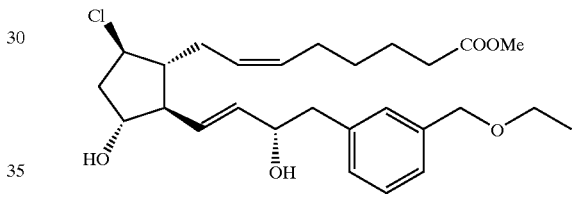

By the same procedures as described in reference example 13, 23, 24 and example 7, the title compound having the following physical data was obtained.

TLC: Rf 0.27 (hexane:ethyl acetate=1:2); NMR (CDCl$_3$): δ 7.32–7.05 (4H, m), 5.57 (1H, dd, J=15.3 Hz, 6.5 Hz), 5.51–5.26 (3H, m), 4.45 (2H, s), 4.36–4.22 (1H, m), 4.06–3.90 (2H, m), 3.66 (3H, s), 3.55 (2H, q, J=7.0 Hz), 3.02–2.68 (4H, m), 2.38–1.82 (10H, m), 1.78–1.58 (2H, m), 1.24 (3H, t, J=7.0 Hz).

EXAMPLE 8

(9β,11α,15α)-9-Chloro-11,15-dihydroxy-16-(3-methoxymethylphenyl)-17,18,19,20-tetranorprost-13E-enoic Acid

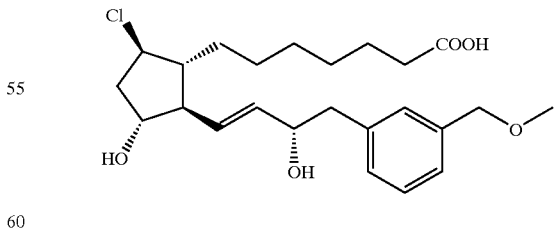

The compound synthesized in example 7 (50.0 mg) was dissolved in methanol (2 ml) and thereto was added a 2N aqueous solution of sodium hydroxide (1 ml). After 1 hour, the solution was acidified with a 1 N hydrochloric acid and the mixture was extracted with ethyl acetate. The organic layer was washed with a saturated aqueous solution of sodium chloride, dried over anhydrous sodium sulfate, concentrated and the residue was purified by column chromatography on silica gel (ethyl acetate→ethyl acetate:acetic acid=50:1) to give the title compound (47.5 mg) having the following physical data.

Description: pale yellow oil; TLC: Rf 0.55 (ethyl acetate:acetic acid=50:1); NMR (CDCl₃): δ 7.34–7.09 (m, 4H), 5.62 (dd, J=15.4 Hz, 5.8 Hz, 1H), 5.47 (dd, J=15.4 Hz, 7.6 Hz, 1H), 4.44 (s, 2H), 4.43–4.32 (m, 1H), 4.12–3.90 (m, 2H), 3.41 (s, 3H), 2.95–2.73 (m, 2H), 2.32 (t, J=6.9 Hz, 2H), 2.28–1.77 (m, 4H), 1.72–1.52 (m, 2H), 1.52–1.16 (m, 11H).

EXAMPLE 8 (1)~8 (9)

By the same procedures as described in reference example 13, 23, 24 and example 7 and 8, the title compound having the following physical data were obtained.

EXAMPLE 8 (1)

(9β,11α,15α)-9-Chloro-11,15-dihydroxy-16-[3-(2-ethoxyethyl)phenyl]-17,18,19,20-tetranorprost-13E-enoic Acid

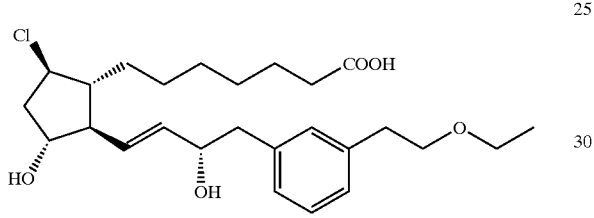

TLC: Rf 0.34 (ethyl acetate); NMR (CDCl₃): δ 7.26–7.00 (m, 4H), 5.62 (dd, J=15.4, 6.0 Hz, 1H), 5.49 (dd, J=15.4, 7.4 Hz, 1H), 4.70–4.22 (m, 2H), 4.20–3.80 (m, 4H), 3.64 (t, J=7.1 Hz, 2H), 3.51 (q, J=7.0 Hz, 2H), 2.94–2.68 (m, 4H), 2.32 (t, J=7.3 Hz, 2H), 2.28–1.78 (m, 4H), 1.78–1.25 (m, 10H), 1.19 (t, J=7.0 Hz, 3H).

EXAMPLE 8 (2)

(9β,11α,15α)-9-chloro-11,15-dihydroxy-16-(3-methyl-4-hydroxyphenyl)-17,18,19,20-tetranorprost-13E-enoic Acid

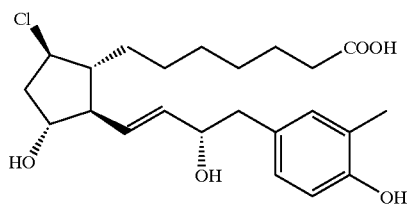

TLC: Rf 0.25 (chloroform:ethhanol=9:1); NMR (CD₃OD): δ 6.87 (d, J=2 Hz, 1H), 6.80 (dd, J=8, 2 Hz, 1H), 6.62 (d, J=8 Hz, 1H), 5.49 (dd, J=15, 6 Hz, 1H), 5.40 (dd, J=15, 8 Hz, 1H), 4.19 (q, J=6 Hz, 1H), 3.98 (q, J=7 Hz, 1H), 3.95 (q, J=7 Hz, 1H), 2.78 (dd, J=13, 6 Hz, 1H), 2.58 (dd, J=13, 7 Hz, 1H), 2.27 (t, J=8 Hz, 2H), 2.15 (s, 3H), 2.2–2.1 (m, 2H), 2.0–1.9 (m, 1H), 1.8–1.7 (m, 1H), 1.65–1.5 (m, 2H), 1.4–1.2 (m, 8H).

EXAMPLE 8 (3)

(9β,11α,15α)-9-Chloro-11,15-dihydroxy-16-(3-methoxymethylphenyl)-1,6-(1,4-phenylene)-2,3,4,5,17,18,19,20-octanorprost-13E-enoic Acid

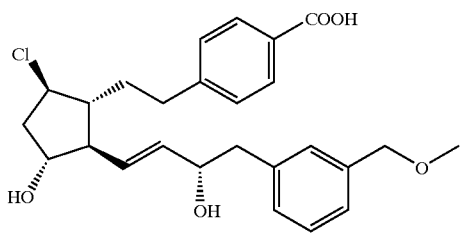

TLC: Rf 0.47 (chloroform:ethhanol 9:1); NMR (CDCl₃): δ 8.01 (d, J=8.4 Hz, 2H), 7.30–7.08 (m, 6H), 5.62 (dd, J=15, 6.4 Hz, 1H), 5.45 (dd, J=15, 8.0 Hz, 1H), 4.40 (s, 2H), 4.38 (m, 1H), 4.03 (m, 2H), 3.83 (br, 3H), 3.40 (s, 3H), 2.95–2.64 (m, 4H), 2.35–1.66 (m, 6H).

EXAMPLE 8 (4)

(9β,11α,15α)-9-Chloro-11,15-dihydroxy-16-[3-(2-fluoroethyl)phenyl]-17,18,19,20-tetranorprost-5Z,13E-dienoic Acid

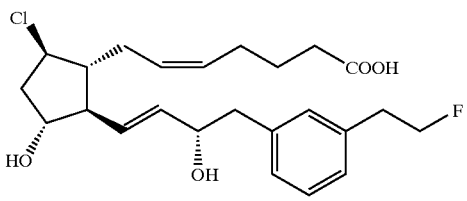

TLC: Rf 0.45 (chloroform:ethhanol=9:1); NMR (CDCl₃): δ 7.25 (1H, m), 7.10 (3H, m), 5.62 (1H, dd, J=15,5.4 Hz), 5.51 (1H, dd, J=15, 7.0 Hz), 5.44 (2H, m), 4.63 (2H, dt, J=47, 6.4 Hz), 4.37 (1H, m), 4.22 (3H, br), 4.03 (2H, m), 2.98 (2H, dt, J=24, 6.4 Hz), 2.82 (2H, m), 2.35 (2H, t, J=6.9 Hz), 2.30–1.87 (8H, m), 1.68 (2H, m).

EXAMPLE 8 (5)

(9β,11α,15α)-9-Chloro-11,15-dihydroxy-16-[3-(2-ethoxyethyl)phenyl]-17,18,19,20-tetranorprost-5Z,13E-dienoic Acid

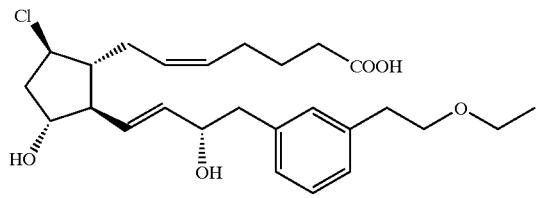

TLC: Rf 0.54 (chloroform:ethhanol=9:1); NMR (CDCl₃): δ 7.23 (m, 1H), 7.06 (m, 3H), 5.62 (dd, J=15, 5.6 Hz, 1H), 5.57–5.36 (m, 3H), 4.38 (m, 1H), 4.03 (m, 2H), 3.80 (br, 3H), 3.65 (t, J=7.2 Hz, 2H), 3.52 (q, J=7.0 Hz, 2H), 2.87 (t, J=7.2 Hz, 2H), 2.81 (m, 2H), 2.34 (t, J=6.8 Hz, 2H), 2.29–1.87 (m, 8H), 1.68 (m, 2H), 1.20 (t, J=7.0 Hz, 3H).

EXAMPLE 8 (6)

(9β,11α,15α)-9-Chloro-11,15-dihydroxy-16-(3-ethoxymethylphenyl)-17,18,19,20-tetranorprost-5Z,13E-dienoic Acid

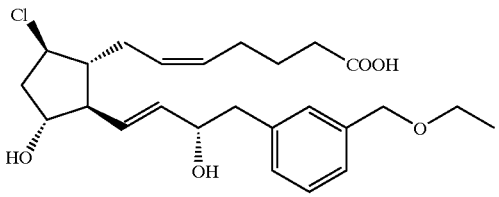

TLC: Rf 0.63 (ethyl acetate:acetic acid=50:1); NMR (CDCl₃): δ 7.33–7.06 (4H, m), 6.00–5.20 (7H, m), 4.46 (2H, s), 4.40–4.26 (1H, m), 4.07–3.90 (2H, m), 3.56 (2H, q, J=7.0 Hz), 2.81 (2H, d, J=6.2 Hz), 1.80 (10H, m), 1.78–1.58 (2H, m), 1.24 (3H, t, J=7.0 Hz).

EXAMPLE 8 (7)

(9β, ,11α,15α)-9-Chloro-11,15-dihydroxy-16-(3-methyl-4-hydroxyphenyl)-17,18,19,20-tetranorprost-5Z,13E-dienoic Acid

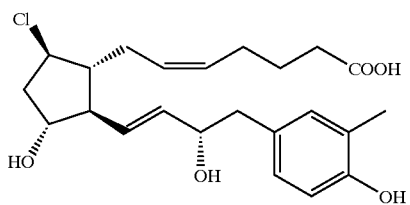

TLC: Rf 0.29 (chloroform:methanol=9:1); NMR (CD₃OD): δ 6.87 (s, 1H), 6.81 (d, J=8 Hz, 1H), 6.62 (d, J=8 Hz, 1H), 5.50 (dd, J=15, 6 Hz, 1H), 5.5–5.3 (m, 3H), 4.18 (q, J=6 Hz, 1H), 4.05–3.9 (m, 2H), 2.77 (dd, J=14, 6 Hz, 1H), 2.57 (dd, J=14, 8 Hz, 1H), 2.29 (t, J=7 Hz, 2H), 2.12 (s, 3H), 2.2–1.9 (m, 7H), 1.9–1.7 (m, 1H), 1.75–1.55 (m, 2H).

EXAMPLE 8 (8)

(9β,11α,15α)-9-Chloro-11,15-dihydroxy-16-(3-methoxymethylphenyl)-17,18,19,20-tetranorprost-5Z,13E-dienoic Acid

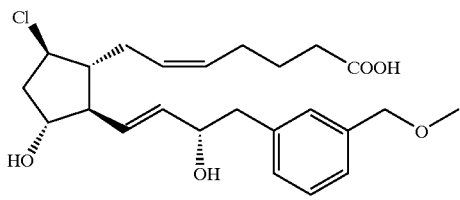

TLC: Rf 0.42 (chloroform:ethhanol=9:1); NMR (CDCl₃): δ 7.33–7.08 (4H, m), 5.60 (1H, dd, J=15, 5.8 Hz), 5.45 (3H, m), 4.50 (3H, br), 4.43 (2H, s), 4.37 (1H, m), 3.99 (2H, m), 3.40 (3H, s), 2.84 (2H, d J=6.6 Hz), 2.34 (2H, t, J=7.0 Hz), 2.28–1.84 (8H, m), 1.68 (2H, m).

EXAMPLE 8 (9)

(9β,11α,15α)-9-Fluoro-11,15-dihydroxy-16-(3-methoxymethylphenyl)-17,18,19,20-tetranorprost-5Z,13E-dienoic Acid

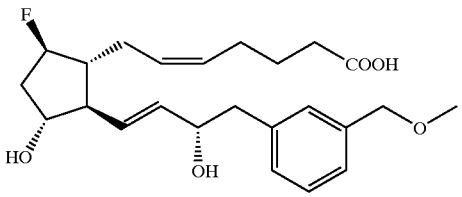

TLC: Rf 0.45 (chloroform:ethhanol=9:1); NMR (CDCl₃): δ 7.36–7.08 (m, 4H), 5.63 (dd, J=15, 5.8 Hz, 1H), 5.57–5.31 (m, 3H), 4.77 (m, 1H), 4.43 (s, 2H), 4.42 (m, 1H), 4.11 (br, 3H), 3.98 (m, 1H), 3.41 (s, 3H), 2.86 (m, 2H), 2.40–1.54 (m, 12H).

EXAMPLE 9

(11α,15α)-9-oxo-11,15-Dihydroxy-16-(3-methoxymethylphenyl)-17,18,19,20-tetranorprost-2E,13E-dienoic Acid Methyl Ester

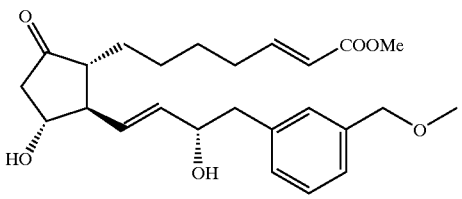

By the same procedures as described in reference example 13 and example 1 using the compound synthesized in reference example 12, the title compound having the following physical data was obtained.

TLC: Rf 0.26 (ethyl acetate); NMR (CDCl₃): δ 7.3–7.1 (m, 4H), 6.93 (dt, J=16, 7 Hz, 1H), 5.80 (d, J=16 Hz, 1H), 5.73 (dd, J=15, 6 Hz, 1H), 5.50 (dd, J=15, 8 Hz, 1H), 4.5–4.35 (m, 3H), 3.92 (q, J=8 Hz, 1H), 3.72 (s, 3H), 3.41 (s, 3H), 2.91 (dd, J=14, 7 Hz, 1H), 2.83 (dd, J=14, 9 Hz, 1H), 2.69 (dd, J=18, 8 Hz, 1H), 2.4–2.1 (m, 5H), 2.0–1.9 (m, 1H), 2.1–1.7 (br), 1.6–1.2 (m, 6H).

EXAMPLE 10

(11α,15α)-9-oxo-11,15-Dihydroxy-16-(3-methoxymethylphenyl)-17,18,19,20-tetranorprost-2E, 13E-dienoic Acid

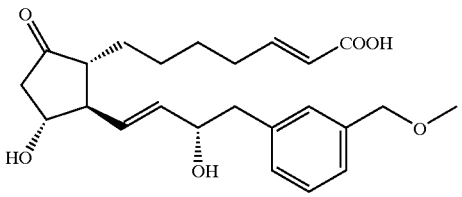

By the same procedure as described in example 2 using the compound synthesized in example 9, the title compound having the following physical data was obtained.

TLC: Rf 0.24 (chloroform=methanol=9:1); NMR (CDCl₃): δ 7.3–7.1 (m, 4H), 7.00 (dt, J=16,7 Hz, 1H), 5.80

(d, J=16 Hz, 1H), 5.72 (dd, J=15,6 Hz, 1H), 5.51 (dd, J=15,9 Hz, 1H), 5.0–3.4 (br), 4.43 (s, 2H), 4.39 (q, J=6 Hz, 1H), 3.93 (brq, 1H), 3.42 (s, 3H), 2.95–2.8 (m, 2H), 2.69 (dd, J=19, 7 Hz, 1H), 2.4–2.1 (m, 4H), 2.0–1.9 (m, 1H), 1.7–1.5 (m, 1H), 1.5–1.2 (m, 5H).

EXAMPLE 11~11 (1)

By the same procedures as described in reference example 19~21 and example 5, the compounds having the following physical data were obtained.

EXAMPLE 11

(11α,15α)-9-oxo-11,15-Dihydroxy-16-(3-methoxymethylphenyl)-16-methyl-17,18,19,20-tetranorprost-5Z,13E-dienoic Acid

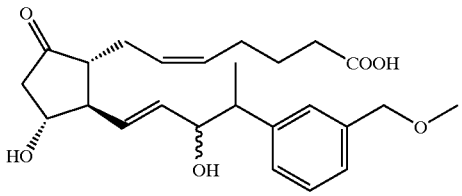

(The compound is a diastereomeric mixture at 16-position.) more polar:

TLC: Rf 0.48 (chloroform:methanol=9:1); NMR (CDCl$_3$): δ 7.3–7.1 (m, 4H), 5.70 and 5.57 (dd, J=15,6 Hz 1H), 5.6–5.3 (m, 3H), 4.5–4.35 (m, 2H), 4.32 and 4.26 (t, J=6 Hz, 1H), 3.93 and 3.70 (brq, 1H), 3.42 (s, 3H), 3.4–2.3 (br), 3.0–2.8 (m, 2H), 2.70 and 2.63 (dd, J=19,8 Hz, 1H), 2.4–1.9 (m, 9H), 1.8–1.6 (m, 2H), 1.38 and 1.29 (d, J=7 Hz, 3H).

EXAMPLE 11 (1)

(11α,15ξ)-9-oxo-11,15-Dihydroxy-16-(3-methyl-4-hydroxyphenyl)-16-methyl-17,18,19,20-tetranorprost-5Z,13E-dienoic Acid

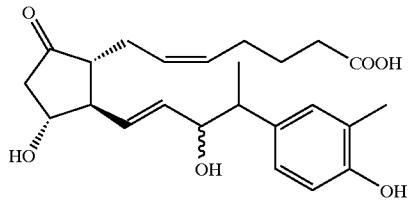

(The compound is a diastereomeric mixture at 16-position.) more polar:

TLC: Rf 0.31 (chloroform:ethhanol=9:1); NMR (CDCl$_3$): δ 6.95–6.75 (m, 2H), 6.69 and 6.63 (d, J=8 Hz, 1H), 5.65–5.1 (m 4H), 4.15–3.9 (m, 2H), 3.2–2.6 (br), 2.8–2.55 (m, 2H), 2.4–1.9 (m, 12H) 1.7–1.55 (m, 2H), 1.27 and 1.15 (d, J=7 Hz, 3H).

FORMULATION EXAMPLE 1

(9β,11α,15ξ)-9-chloro-11,15-dihydroxy-16-(3-methoxymethyl-4-hydroxyphenyl)-17,18,19,20-tetranorprost-5Z,13E-dienoic acid (3 mg) in ethanol
stearic acid . . . 100 mg
silicon dioxide . . . 20 mg
talc . . . 10 mg
calcium cellulose glycolate . . . 200 mg
microcrystalline cellulose . . . 5000 mg
were admixed in a conventional method, dried, added microcrystalline cellulose to sum 10 g, mixed until homogeneous and punched out in a conventional method, to obtain 100 tablets each containing 30 μg of active ingredient.

FORMULATION EXAMPLE 2

A clathrate (6 mg) of (11α,15α)-9-oxo-11,15-dihydroxy-16-(3-methoxymethylphenyl)-17,18,19,20-tetranorprost-13E-enoic acid (0.5 mg) in α-cyclodextrin was dissolved in distilled water for injection (300 ml) and the solution was sterilized in a conventional method, placed 3 ml portions into 5 ml ampoules to obtain 100 ampoules each containing 5 μg of the active ingredient.

What is claimed is:

1. An ω-substituted phenyl-prostaglandin E derivative of formula (I)

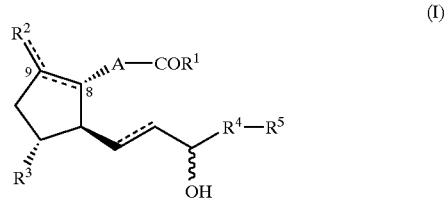

(wherein

A is C2~8 alkylene, C2~8 alkenylene, C1~4 alkylene-phenylene or C2~4 alkenylene-phenylene, $R^1$ is hydroxy, C1~6 alkyloxy, C1~6 alkyloxy-C1~6 alkyloxy, HO—C1~6 alkyloxy or a formula of $NR^6R^7$ (wherein $R^6$ and $R^7$ are each independently hydrogen atom or C1~4 alkyl), $R^2$ is oxo, halogen or a group of formula $R^8$—COO— (wherein $R^8$ is hydrogen, C1~4 alkyl, phenyl or phenyl(C1~4 alkyl), C1~4 alkyloxy, HOOC—C1~4 alkyl, C1~4 alkyloxy-carbonyl-C1~4 alkyl, HOOC—C2~4 alkenyl or C1~4 alkyloxy-carbonyl-C2~4 alkenyl), $R^3$ is hydrogen or hydroxy, $R^4$ is C1~4 alkylene, $R^5$ is phenyl substituted by the following groups:
  i) 1~3 groups selected from
    C1~4 alkyloxy-C1~4 alkyl,
    C2~4 alkenyloxy-C1~4 alkyl,
    C2~4 alkynyloxy-C1~4 alkyl,
    C3~7 cycloalkyloxy-C1~4 alkyl,
    C3~7 cycloalkyl(C1~4 alkyloxy)-C1~4 alkyl,
    phenyloxy-C1~4 alkyl,
    phenyl-C1~4 alkyloxy-C1~4 alkyl,
    C1~4 alkylthio-C1~4 alkyl,
    C2~4 alkenylthio-C1~4 alkyl;
    C2~4 alkynylthio-C1~4 alkyl;
    C3~7 cycloalkylthio-C1~4 alkyl,
    C3~7 cycloalkyl(C1~4 alkylthio)-C1~4 alkyl,
    phenylthio-C1~4 alkyl and
    phenyl-C1~4 alkylthio-C1~4 alkyl,
  ii) C1~4 alkyloxy-C1~4 alkyl and C1~4 alkyl,
    C1~4 alkyloxy-C1~4 alkyl and C1~4 alkyloxy,
    C1~4 alkyloxy-C1~4 alkyl and hydroxy,
    C1~4 alkyloxy-C1~4 alkyl and halogen,
    C1~4 alkylthio-C1~4 alkyl and C1~4 alkyl,
    C1~4 alkylthio-C1~4 alkyl and C1~4 alkyloxy, C1~4 alkylthio-C1~4 alkyl and hydroxy or
C1~4 alkylthio-C1~4 alkyl and halogen
iii) mono halo-C1~4 alkyl or hydroxy-C1~4 alkyl, or
iv) C1~4 alkyl and hydroxy; and
wherein ═is a bond or a double bond,
and when $R^2$ is $R^8$—COO—, $R^8$ is C1~6 alkyloxy, C1~6 alkyloxy-C1~6 alkyloxy or HO—C1~6 alkyloxy and the bond in the 8–9 position is a double bond),
a non-toxic salt thereof or a cyclodextrin clathrate thereof.

2. A compound according to claim 1, wherein $R^1$ is hydroxy.

3. A compound according to claim 1, wherein $R^1$ is C1~6 alkyloxy, C1~6 alkyloxy-C1~6 alkyloxy or HO—C1~6 alkyloxy.

4. A compound according to claim 1, wherein $R^1$ is $NR^6R^7$ (wherein $R^6$ and $R^7$ have the same meanings as described in claim 1).

5. A compound according to claim 1, wherein $R^2$ is oxo.

6. A compound according to claim 1, wherein $R^2$ is halogen.

7. A compound according to claim 1, wherein $R^2$ is $R^8$—COO—

(wherein $R^8$ has the same meaning as described in claim 1).

8. A compound according to claim 1, wherein $R^5$ is phenyl substituted by
i) 1~3 of
C1~4 alkyloxy-C1~4 alkyl,
C2~4 alkenyloxy-C1~4 alkyl,
C2~4 alkynyloxy-C1~4 alkyl,
C3~7 cycloalkyloxy-C1~4 alkyl,
C3~7 cycloalkyl(C1~4 alkyloxy)-C1~4 alkyl,
phenyloxy-C1~4 alkyl,
phenyl-C 1~4 alkyloxy-C1~4 alkyl,
C1~4 alkylthio-C1~4 alkyl,
C2~4 alkenylthio-C1~4 alkyl,
C2~4 alkynylthio-C1~4 alkyl,
C3~7 cycloalkylthio-C1~4 alkyl,
C3~7 cycloalkyl(C1~4 alkylthio)-C1~4 alkyl,
phenylthio-C1~4 alkyl or
phenyl-C1~4 alkylthio-C1~4 alkyl.

9. A compound according to claim 1, wherein $R^5$ is
ii) phenyl substituted by
C1~4 alkyloxy-C1~4 alkyl and C1~4 alkyl,
C1~4 alkyloxy-C1~4 alkyl and C1~4 alkyloxy,
C1~4 alkyloxy-C1~4 alkyl and hydroxy,
C1~4 alkyloxy-C1~4 alkyl and halogen,
C1~4 alkylthio-C1~4 alkyl and C1~4 alkyl,
C1~4 alkylthio-C1~4 alkyl and C1~4 alkyloxy,
C1~4 alkylthio-C1~4 alkyl and hydroxy, or
C1~4 alkylthio-C1~4 alkyl and halogen.

10. A compound according to claim 1, wherein $R^5$ is
iii) phenyl substituted by halo-C1~4 alkyl or hydroxy-C1~4 alkyl.

11. A compound according to claim 1, wherein $R^5$ is
iv) phenyl substituted by C1~4 alkyl and hydroxy.

12. A compound according to claim 1, wherein A is C2~8 alkylene or C2~8 alkenylene.

13. A compound according to claim 1, wherein A is C1~4 alkylene-phenylene or C2~4 alkenylene-phenylene.

14. A compound according to claim 1, which is
(1) (11α,15α)-9-oxo-11,15-dihydroxy-16-(3-methoxymethylphenyl)-17,18,19,20-tetranorprost-13E-enoic acid,
(2) (11α,15α, )-9-oxo-11,15-dihydroxy-16-(3-ethoxymethylphenyl)-17,18,19,20-tetranorprost-5Z,13E-dienoic acid,
(3) (11α,15α)-9-oxo-11,15-dihydroxy-16-[3-(2-ethoxyethyl)phenyl]-17,18,19,20-tetranorprost-13E-enoic acid,
(4) (11α,15α)-9-oxo-11,15-dihydroxy-16-(3-ethoxymethylphenyl)-17,18,19,20-tetranorprost-13E-enoic acid,
(5) (11α,15α)-9-oxo-11,15-dihydroxy-16-[3-(2-ethoxyethyl)phenyl]-17,18,19,20-tetranorprost-5Z,13E-dienoic acid,
(6) (15α)-9-oxo-15-hydroxy-16-(3-ethoxymethylphenyl)-17,18,19,20-tetranorprost-5Z,13E-dienoic acid,
(7) (11α,15α)-9-oxo-11,15-dihydroxy-16-(3-methoxymethylphenyl)-17,18,19,20-tetranorprost-5Z,13E-dienoic acid,
(8) (15α)-9-oxo-15-hydroxy-16-(3-methoxymethylphenyl)-17,18,19,20-tetranorprost-5Z,13E-dienoic acid,
(9) (11α,15ξ)-9-oxo-11,15-dihydroxy-16-[3-(2-isopropyloxyethyl)phenyl]-17,18,19,20-tetranorprost-13E-enoic acid,
(10) (11α,15ξ)-9-oxo-11,15-dihydroxy-16-(3-isopropyloxymethylphenyl)-17,18,19,20-tetranorprost-13E-enoic acid,
(11) (11α,15ξ)-9-oxo-11,15-dihydroxy-16-[3-(2-propyloxyethyl)phenyl]-17,18,19,20-tetranorprost-13E-enoic acid,
(12) (11α,15ξ)-9-oxo-11,15-dihydroxy-16-[3-(2-isopropyloxyethyl)phenyl]-17,18,19,20-tetranorprost-5Z,13E-dienoic acid,
(13) (11α,15ξ)-9-oxo-11,15-dihydroxy-16-(3-isopropyloxymethylphenyl)-17,18,19,20-tetranorprost-5Z,13E-dienoic acid,
(14) (11α,15ξ)-9-oxo-11,15-dihydroxy-16-[3-(2-propyloxyethyl)phenyl]-17,18,19,20-tetranorprost-5Z,13E-dienoic acid,
(15) (11α,15ξ)-9-oxo-11,15-dihydroxy-16-(3-propyloxymethylphenyl)-17,18,19,20-tetranorprost-13E-enoic acid,
(16) (11α,15ξ)-9-oxo-11,15-dihydroxy-16-[3-(2-methoxyethyl) phenyl]-17,18,19,20-tetranorprost-13E-enoic acid,
(17) (11α,15ξ)-9-oxo-11,15-dihydroxy-16-[3-(2-methoxyethyl)phenyl]-17,18,19,20-tetranorprost-5Z,13E-dienoic acid,
(18) (11α,15ξ)-9-oxo-11,15-dihydroxy-16-(3-propyloxymethylphenyl)-17,18,19,20-tetranorprost-5Z,13E-dienoic acid,
(19) (11α,15α)-9-oxo-11,15-dihydroxy-16-(3-methoxymethylphenyl)-17,18,19,20-tetranorprost-2E,13E-dienoic acid,
(20) (11α,15ξ)-9-oxo-11,15-dihydroxy-16-(3-methoxymethylphenyl)-16-methyl-17,18,19,20-tetranorprost-5Z,13E-dienoic acid,
(21) (11α,15α)-9-oxo-11,15-dihydroxy-16-(3-methyl-4-hydroxyphenyl)-16-methyl-17,18,19,20-tetranorprost-5Z,13E-dienoic acid,
(22) (11α,15α)-9-oxo-11,15-dihydroxy-16-[3-(2-ethoxyethyl)phenyl]-1,6-(1,4-phenylene)-2,3,4,5,17,18,19,20-octanorprost-13E-enoic acid,
(23) (11α,15α)-9-oxo-11,15-dihydroxy-16-(3-methoxymethylphenyl)-1,6-(1,4-phenylene)-2,3,4,5,17,18,19,20-octanorprost-13E-enoic acid or
(24) (11α,15α)-9-oxo-11,15-dihydroxy-16-(3-ethoxymethylphenyl)-1,6-(1,4-phenylene)-2,3,4,5,17,18,19,20-octanorprost-13E-enoic acid, or a methyl ester thereof.

15. A compound according to claim 1, which is
(1) (11α,15ξ)-9-oxo-11,15-dihydroxy-16-(3-methoxymethyl-5-methoxyphenyl)-17,18,19,20-tetranorprost-13E-enoic acid or (2) (11α,15ξ)-9-oxo-11,15-dihydroxy-16-(3-methoxymethyl-5-methoxyphenyl)-17,18,19,20-tetranorprost-5Z,13E-dienoic acid, or a methyl ester thereof.

16. A compound according to claim 1, which is (1) (11α,15α)-9-oxo-11,15-dihydroxy-16-[3-(2-fluoroethyl)phenyl]-17,18,19,20-tetranorprost-13E-enoic acid, (2) (11α,15α)-9-oxo-11,15-dihydroxy-16-[3-(2-fluoroethyl)phenyl]-17,18,19,20-tetranorprost-5Z,13E-dienoic acid or (3) (11α,15α)-9-oxo-11,15-dihydroxy-16-[3-(2-fluoroethyl)phenyl]-1,6-(1,4-phenylene)-2,3,4,5,17,18,19,20-octanorprost-13E-enoic acid, or a methyl ester thereof.

17. A compound according to claim 1, which is (1) (11α,15α)-9-oxo-11,15-dihydroxy-16-(3-methyl-4-hydroxyphenyl)-17,18,19,20-tetranorprost-13E-enoic acid, (2) (11α,15α)-9-oxo-11,15-dihydroxy-16-(3-methyl-4-hydroxyphenyl)-17,18,19,20-tetranorprost-5Z,13E-dienoic acid, (3) (11α,15α)-9-oxo-11,15-dihydroxy-16-(3-propyl-4-hydroxyphenyl)-17,18,19,20-tetranorprost-13E-enoic acid, (4) (11α,15α)-9-oxo-11,15-dihydroxy-16-(3-propyl-4-hydroxyphenyl)-17,18,19,20-tetranorprost-5Z,13E-dienoic acid or (5) (11α,15α)-9-oxo-11,15-dihydroxy-16-(3-methyl-4-hydroxyphenyl)-1,6-(1,4-phenylene)-2,3,4,5,17,18,19,20-octanorprost-13E-enoic acid, or a methyl ester thereof.

18. A compound according to claim 1, which is (1) (9β,11α,15ξ)-9-chloro-11,15-dihydroxy-16-[3-(2-isopropyloxyethyl)phenyl]-17,18,19,20-tetranorprost-5Z,13E-dienoic acid, (2) (9β,11α,15ξ)-9-chloro-11,15-dihydroxy-16-(3-isopropyloxymethylphenyl)-17,18,19,20-tetranorprost-5Z,13E-dienoic acid, (3) (9β,11α,15ξ)-9-chloro-11,15-dihydroxy-16-[3-(2-methoxyethyl)phenyl]-17,18,19,20-tetranorprost-5Z,13E-dienoic acid, (4) (9β,11α,15ξ)-9-chloro-11,15-dihydroxy-16-[3-(2-propyloxyethyl)phenyl]-17,18,19,20-tetranorprost-5Z,13E-dienoic acid, (5) (9β, 11α,15ξ)-9-chloro-11,15-dihydroxy-16-(3-propyloxymethylphenyl)-17,18,19,20-tetranorprost-5Z,13E-dienoic acid, (6) (9β,11α,15ξ)-9-fluoro-11,15-dihydroxy-16-(3-ethoxymethylphenyl)-17,18,19,20-tetranorprost-5Z,13E-dienoic acid, (7) (9β,11α,15ξ)-9-fluoro-11,15-dihydroxy-16-(3-propyloxymethylphenyl)-17,18,19,20-tetranorprost-5Z,13E-dienoic acid, (8) (9β,11α,15α)-9-chloro-11,15-dihydroxy-16-(3-methoxymethylphenyl)-17,18,19,20-tetranorprost-13E-enoic acid, (9) (9β,11α,15α)-9-chloro-11,15-dihydroxy-16-(3-ethoxymethylphenyl)-17,18,19,20-tetranorprost-5Z,13E-dienoic acid,

(10) (9β,11α,15α)-9-chloro-11,15-dihydroxy-16-[3-(2-ethoxyethyl)phenyl]-17,18,19,20-tetranorprost-13E-enoic acid,

(11) (9β,11α,15α)-9-chloro-11,15-dihydroxy-16-[3-(2-ethoxyethyl)phenyl]-17,18,19,20-tetranorprost-5Z,13E-dienoic acid,

(12) (9β,11α,15α)-9-chloro-11,15-dihydroxy-16-(3-methoxymethylphenyl)-17,18,19,20-tetranorprost-5Z,13E-dienoic acid,

(13) (9α,11α,15α)-9-fluoro-11,15-dihydroxy-16-(3-methoxymethyl phenyl)-17,18,19,20-tetranorprost-5Z,13E-dienoic acid or

(14) (9β,11α,15α)-9-chloro-11,15-dihydroxy-16-(3-methoxymethyl phenyl)-1,6-(1,4-phenylene)-2,3,4,5,17,18,19,20-octanorprost-13E-enoic acid, or a methyl ester thereof.

19. A compound according to claim 1, which is (1) (9α,11α,15ξ)-9-chloro-11,15-dihydroxy-16-(3-methoxymethyl-4-hydroxyphenyl)-17,18,19,20-tetranorprost-5Z,13E-dienoic acid, (2) (9α,11α,15ξ)-9-chloro-11,15-dihydroxy-16-[3-(2-ethoxyethyl)-4-hydroxyphenyl]-17,18,19,20-tetranorprost-5Z,13E-dienoic acid or (3) (9α,11α,15ξ)-9-chloro-11,15-dihydroxy-16-(3-methoxymethyl-5-methoxyphenyl)-17,18,19,20-tetranorprost-5Z,13E-dienoic acid, or a methyl ester thereof.

20. A compound according to claim 1, which is (1) (9β,11α,15ξ)-9-chloro-11,15-dihydroxy-16-(3-hydroxymethylphenyl)-17,18,19,20-tetranorprost-5Z,13E-dienoic acid or (2) (9β,11α,15α)-9-chloro-11,15-dihydroxy-16-[3-(2-fluoroethyl)phenyl]-17,18,19,20-tetranorprost-5Z,13E-dienoic acid, or a methyl ester thereof.

21. A compound according to claim 1, which is (1) (9β,11α,15ξ)-9-chloro-11,15-dihydroxy-16-(3-ethyl-4-hydroxyphenyl)-17,18,19,20-tetranorprost-5Z,13E-dienoic acid, (2) (9β,11α,15ξ)-9-chloro-11,15-dihydroxy-16-(3-propyl-4-hydroxyphenyl)-17,18,19,20-tetranorprost-5Z,13E-dienoic acid, (3) (9β,11α,15α)-9-chloro-11,15-dihydroxy-16-(3-methyl-4-hydroxyphenyl)-17,18,19,20-tetranorprost-13E-enoic acid or (4) (9β,11α,15α)-9-chloro-11,15-dihydroxy-16-(3-methyl-4-hydroxyphenyl)-17,18,19,20-tetranorprost-5Z,13E-dienoic acid, or a methyl ester thereof.

22. A compound according to claim 1, which is (1) (11α,15α)-9-butanoyloxy-11,15-dihydroxy-16-(3-methoxymethylphenyl)-17,18,19,20-tetranorprost-8,13E-dienoic acid 2-hydroxyethyl ester or (2) (11α,15α)-9-butanoyloxy-11,15-dihydroxy-16-(3-methoxymethyl phenyl)-17,18,19,20-tetranorprost-8,13E-dienoic acid, (3) (11α,15α)-9-(3-carboxypropanoyloxy)-11,15-dihydroxy-16-(3-methoxymethylphenyl)-17,18,19,20-tetranorprost-8,13E-dienoic acid, (4) (11α,15α)-9-acetyloxy-11,15-dihydroxy-16-(3-methoxymethylphenyl)-17,18,19,20-tetranorprost-8,13E-dienoic acid or (5) (11α,15α)-9-butanoyloxy-11,15-dihydroxy-16-(3-methyl-4-hydroxyphenyl)-17,18,19,20-tetranorprost-8,13E-dienoic acid, or a methyl ester thereof.

23. A medicament comprising an ω-substituted phenyl-prostaglandin E derivative of formula (I) described in claim 1, a non-toxic salt thereof or a cyclodextrin clathrate thereof as active ingredient.

24. A compound according to claim 1, which is (11α,15α)-9-oxo-11,15-dihydroxy-16-(3-methoxymethylphenyl)-17,18,19,20-tetranorprost-13E-enoic acid.

* * * * *